(12) United States Patent
Grenon et al.

(10) Patent No.: US 8,888,286 B2
(45) Date of Patent: Nov. 18, 2014

(54) FULL-EYE ILLUMINATION OCULAR SURFACE IMAGING OF AN OCULAR TEAR FILM FOR DETERMINING TEAR FILM THICKNESS AND/OR PROVIDING OCULAR TOPOGRAPHY

(71) Applicant: TearScience, Inc., Morrisville, NC (US)

(72) Inventors: Stephen M. Grenon, Durham, NC (US); Donald R. Korb, Boston, MA (US)

(73) Assignee: TearScience, Inc., Morrisville, NC (US)

( * ) Notice: Subject to any disclaimer, the term of this patent is extended or adjusted under 35 U.S.C. 154(b) by 0 days.

(21) Appl. No.: 14/137,105

(22) Filed: Dec. 20, 2013

(65) Prior Publication Data
US 2014/0104574 A1   Apr. 17, 2014

Related U.S. Application Data

(63) Continuation-in-part of application No. 12/798,325, filed on Apr. 1, 2010, now Pat. No. 8,545,017, and a (Continued)

(51) Int. Cl.
| | | |
|---|---|---|
| A61B 3/14 | (2006.01) | |
| A61B 3/10 | (2006.01) | |
| A61B 3/02 | (2006.01) | |
| A61B 5/05 | (2006.01) | |
| A61B 3/00 | (2006.01) | |
| A61B 3/107 | (2006.01) | |
| G06T 7/00 | (2006.01) | |

(52) U.S. Cl.
CPC ............... *A61B 3/0025* (2013.01); *A61B 3/14* (2013.01); *A61B 3/0058* (2013.01); *A61B 3/1005* (2013.01); *A61B 3/107* (2013.01); *A61B 3/101* (2013.01); *G06T 7/0012* (2013.01); *G06T 2207/30041* (2013.01); *G06T 2207/10016* (2013.01); *G06T 2207/10144* (2013.01); *G06T 2207/20224* (2013.01)
USPC ........... 351/206; 351/210; 351/221; 351/222; 600/425

(58) Field of Classification Search
USPC ......... 351/206, 200, 205, 209, 210, 221–223, 351/245, 246, 212, 208, 160 R, 159; 600/247, 356, 346, 476, 425
See application file for complete search history.

(56) References Cited

U.S. PATENT DOCUMENTS

| | | |
|---|---|---|
| 3,941,901 A | 3/1976 | Harsch |
| 3,971,952 A | 7/1976 | Inbar et al. |

(Continued)

FOREIGN PATENT DOCUMENTS

| | | |
|---|---|---|
| DE | 3108878 A1 | 9/1982 |
| EP | 0943288 A1 | 9/1999 |

(Continued)

OTHER PUBLICATIONS

Fogt, Nick, et al., "Interferometric Measurement of Tear Film Thickness by use of Spectral Oscillations" J. Opt. Soc. Am. A., vol. 15, No. 1, Jan. 1998, 8 pages (pp. 268-275).

(Continued)

*Primary Examiner* — Dawayne A Pinkney
(74) *Attorney, Agent, or Firm* — Withrow & Terranova PLLC

(57) ABSTRACT

Ocular surface interferometry (OSI) devices, systems, and methods are disclosed for measuring a tear film layer thickness (TFLT) of the ocular tear film, including the lipid layer thickness (LLT) and/or the aqueous layer thickness (ALT). The TFLT can be used to diagnose dry eye syndrome (DES). Certain embodiments also include ocular topography devices, systems and methods for deducing corneal shape by capturing an image of a target reflecting from the surface of the cornea. The image of the target contains topography information that is reviewable by a clinician to diagnose the health of the patient's eye by detecting corneal aberrations and/or abnormalities in corneal shape. Certain embodiments also include a combination of the OSI and ocular topography devices, systems and methods to provide imaging that can be used to yield a combined diagnosis of the patient's tear film and corneal shape.

27 Claims, 48 Drawing Sheets
(24 of 48 Drawing Sheet(s) Filed in Color)

Related U.S. Application Data continuation-in-part of application No. 12/798,275, filed on Apr. 1, 2010, now Pat. No. 8,746,883.

(60) Provisional application No. 61/745,213, filed on Dec. 21, 2012, provisional application No. 61/211,596, filed on Apr. 1, 2009.

(56) References Cited

U.S. PATENT DOCUMENTS

| | | | |
|---|---|---|---|
| 4,122,348 A | 10/1978 | Bruck | |
| 4,533,223 A | 8/1985 | Duparchy | |
| 4,597,648 A | 7/1986 | Feldon et al. | |
| 4,705,037 A | 11/1987 | Peyman et al. | |
| 4,747,683 A | 5/1988 | Doane | |
| 4,842,401 A | 6/1989 | Maurice | |
| 4,885,352 A | 12/1989 | Erickson | |
| 4,938,584 A | 7/1990 | Suematsu et al. | |
| 5,110,200 A | 5/1992 | Snook | |
| D330,769 S | 11/1992 | Blaha et al. | |
| 5,258,791 A | 11/1993 | Penney et al. | |
| 5,268,305 A | 12/1993 | Ribi et al. | |
| 5,427,915 A | 6/1995 | Ribi et al. | |
| 5,475,452 A | 12/1995 | Kuhn et al. | |
| 5,491,097 A | 2/1996 | Ribi et al. | |
| 5,494,829 A | 2/1996 | Sandstrom et al. | |
| 5,571,568 A | 11/1996 | Ribi et al. | |
| 5,621,523 A | 4/1997 | Oobayashi et al. | |
| 5,622,872 A | 4/1997 | Ribi | |
| 5,625,428 A | 4/1997 | Isogai | |
| 5,626,134 A | 5/1997 | Zuckerman | |
| 5,642,137 A | 6/1997 | Kitazumi | |
| 5,647,032 A | 7/1997 | Jutamulia | |
| 5,712,721 A | 1/1998 | Large | |
| 5,719,659 A | 2/1998 | Suzuki | |
| D394,505 S | 5/1998 | Hayashi | |
| 5,760,950 A | 6/1998 | Maly et al. | |
| 5,886,767 A | 3/1999 | Snook | |
| 5,988,815 A | 11/1999 | Maus et al. | |
| 6,059,773 A | 5/2000 | Maloney et al. | |
| 6,127,183 A | 10/2000 | Ivarsson et al. | |
| 6,198,540 B1 | 3/2001 | Ueda et al. | |
| 6,213,605 B1 | 4/2001 | D'Souza et al. | |
| 6,236,459 B1 | 5/2001 | Negahdaripour | |
| 6,299,305 B1 | 10/2001 | Miwa | |
| 6,394,603 B2 | 5/2002 | Miwa et al. | |
| 6,447,119 B1 | 9/2002 | Stewart et al. | |
| 6,450,641 B2 | 9/2002 | D'Souza et al. | |
| D465,850 S | 11/2002 | Takizawa | |
| D472,637 S | 4/2003 | Cooper et al. | |
| 6,659,613 B2 | 12/2003 | Applegate et al. | |
| 6,685,320 B2 | 2/2004 | Hirohara et al. | |
| 6,736,507 B2 | 5/2004 | Kudryashov et al. | |
| 6,964,814 B2 | 11/2005 | Fujii et al. | |
| 7,073,906 B1 | 7/2006 | Portney | |
| 7,121,666 B2 | 10/2006 | Tseng et al. | |
| 7,144,111 B1 | 12/2006 | Ross, III et al. | |
| D552,736 S | 10/2007 | Yamaoka | |
| 7,431,458 B2 | 10/2008 | Jongsma et al. | |
| D582,556 S | 12/2008 | Yamaoka | |
| 7,611,245 B2 | 11/2009 | Carbonari | |
| D607,562 S | 1/2010 | Heine et al. | |
| 7,654,669 B2 | 2/2010 | Suzuki | |
| 7,688,453 B2 | 3/2010 | Williby et al. | |
| 7,758,190 B2 | 7/2010 | Korb et al. | |
| 7,771,353 B2 | 8/2010 | Luce | |
| 7,982,881 B2 | 7/2011 | Fercher et al. | |
| 7,988,294 B2 | 8/2011 | Korb et al. | |
| 8,092,023 B2 | 1/2012 | Korb et al. | |
| 8,192,026 B2 | 6/2012 | Gravely et al. | |
| 8,215,774 B2 | 7/2012 | Korb et al. | |
| 8,249,695 B2 | 8/2012 | Grenon et al. | |
| 8,255,039 B2 | 8/2012 | Gravely et al. | |
| 8,545,017 B2 | 10/2013 | Korb et al. | |
| 8,585,204 B2 | 11/2013 | Gravely et al. | |
| 8,591,033 B2 | 11/2013 | Korb et al. | |
| 8,602,557 B2 | 12/2013 | Huth et al. | |
| 8,617,229 B2 | 12/2013 | Korb et al. | |
| 8,641,194 B2 | 2/2014 | Primeau et al. | |
| 2001/0055095 A1 | 12/2001 | D'Souza et al. | |
| 2002/0180929 A1 | 12/2002 | Tseng et al. | |
| 2003/0056281 A1 | 3/2003 | Hasegawa | |
| 2004/0212781 A1 | 10/2004 | Mihashi et al. | |
| 2005/0096431 A1 | 5/2005 | Fujii et al. | |
| 2005/0119737 A1 | 6/2005 | Bene et al. | |
| 2005/0159657 A1 | 7/2005 | Cappo et al. | |
| 2006/0055956 A1 | 3/2006 | Takahashi et al. | |
| 2006/0103724 A1 | 5/2006 | Jongsma et al. | |
| 2006/0109423 A1 | 5/2006 | Wang | |
| 2006/0140454 A1 | 6/2006 | Northcott et al. | |
| 2006/0159722 A1 | 7/2006 | Braithwaite et al. | |
| 2006/0270802 A1 | 11/2006 | Washizu et al. | |
| 2008/0002202 A1 | 1/2008 | Hall et al. | |
| 2008/0161741 A1 | 7/2008 | Bene et al. | |
| 2008/0273171 A1 | 11/2008 | Huth et al. | |
| 2008/0285043 A1 | 11/2008 | Fercher et al. | |
| 2008/0287808 A1 | 11/2008 | Tearney et al. | |
| 2008/0309855 A1 | 12/2008 | Yan et al. | |
| 2008/0316499 A1 | 12/2008 | Korb et al. | |
| 2008/0319323 A1 | 12/2008 | Gravely et al. | |
| 2009/0161090 A1 | 6/2009 | Campbell et al. | |
| 2009/0201465 A1 | 8/2009 | Huth | |
| 2009/0225276 A1 | 9/2009 | Suzuki | |
| 2009/0275929 A1 | 11/2009 | Zickler | |
| 2010/0026323 A1 | 2/2010 | Tiefenthaler | |
| 2010/0102211 A1 | 4/2010 | Murooka et al. | |
| 2010/0253907 A1 | 10/2010 | Korb et al. | |
| 2010/0259721 A1 | 10/2010 | Korb et al. | |
| 2010/0315591 A1 | 12/2010 | Gratton et al. | |
| 2011/0007321 A1 | 1/2011 | Everett et al. | |
| 2011/0043661 A1 | 2/2011 | Podoleanu | |
| 2011/0053283 A1 | 3/2011 | Hood et al. | |
| 2011/0096292 A1 | 4/2011 | Saito | |
| 2011/0181836 A1 | 7/2011 | Rowe | |
| 2011/0206291 A1 | 8/2011 | Kashani et al. | |
| 2011/0237999 A1 | 9/2011 | Muller et al. | |
| 2011/0273550 A1 | 11/2011 | Amano et al. | |
| 2011/0292395 A1 | 12/2011 | Fercher et al. | |
| 2013/0010257 A1 | 1/2013 | Primeau et al. | |
| 2013/0141698 A1 | 6/2013 | Huth et al. | |
| 2013/0293842 A1 | 11/2013 | Grenon et al. | |
| 2013/0308095 A1 | 11/2013 | Korb et al. | |
| 2014/0118699 A1 | 5/2014 | Huth et al. | |

FOREIGN PATENT DOCUMENTS

| | | |
|---|---|---|
| EP | 1900320 A1 | 3/2008 |
| EP | 2189108 A1 | 5/2010 |
| EP | 2695570 A1 | 2/2014 |
| EP | 1900320 B1 | 4/2014 |
| GB | 2407378 B | 9/2006 |
| JP | 6269412 A | 9/1994 |
| JP | 7002647 A | 1/1995 |
| JP | 7136120 A | 5/1995 |
| JP | 07313464 A | 12/1995 |
| JP | 07313465 A | 12/1995 |
| JP | 8052112 A | 2/1996 |
| JP | 8098811 A | 4/1996 |
| JP | 2001309889 A | 11/2001 |
| JP | 2005211173 A | 8/2005 |
| JP | 2005211633 A | 8/2005 |
| JP | 2005230328 A | 9/2005 |
| JP | 2007068928 A | 3/2007 |
| JP | 2007209370 A | 8/2007 |
| JP | 2007523382 A | 8/2007 |
| JP | 2008246004 A | 10/2008 |
| JP | 2009134276 A | 6/2009 |
| KR | 101259056 B1 | 4/2013 |
| WO | 0026614 A1 | 5/2000 |
| WO | 2005044099 A1 | 5/2005 |
| WO | 2007004348 A1 | 1/2007 |
| WO | 2008137863 A2 | 11/2008 |
| WO | 2008156883 A | 12/2008 |
| WO | 2012137545 A1 | 10/2012 |

(56) References Cited

FOREIGN PATENT DOCUMENTS

| WO | 2013082356 | A2 | 6/2013 |
|---|---|---|---|
| WO | 2013082356 | A3 | 6/2013 |
| WO | 2013166352 | A2 | 11/2013 |
| WO | 2013166477 | A2 | 11/2013 |
| WO | 2014018640 | A1 | 1/2014 |

OTHER PUBLICATIONS

Foulks, G.N. et al., "Meibomian Gland Dysfunction: a Clinical Scheme for Description, Diagnosis, Classification, and Grading," The Ocular Surface, vol. 1, No. 3, Jul. 2003, pp. 107-126.
Foulks, G.N., "The Correlation Between the Tear Film Lipid Layer and Dry Eye Disease," Survey of Ophthalmology, vol. 52, No. 4, Jul.-Aug. 2007, pp. 369-374.
Foulks, G., "Ocular surface cell biology—from the light to the dark side," Ocular Surface, vol. 10, No. 4, Oct. 2012, 1 page.
Garcia, Julius, "Research Report; Tear Film Measurement" Report No. 09354231-1; Aug. 2006, 46 pages.
Garcia-Resua, C., et al., "Clinical Evaluation of the Tears Lipid Layer in a Young University Population" Rev. Esp. Contact, vol. 12, 2005, 6 pages.
Garncarz, B.E. et al., "Corneal Topography Measurement by Means of Radial Shearing Interference II—Experiment Results," Optik, vol. 113, No. 1, 2002, pp. 46-50.
Goto, E. et al., "Differentiation of Lipid Tear Deficiency Dry Eye by Kinetic Analysis of Tear Interference Images," Archives of Ophthalmology, vol. 121, No. 2 Feb. 2003, pp. 173-180.
Goto, E. et al., "Successful Tear Lipid Layer Treatment for Refractory Dry Eye in Office Workers by Low-Dose Lipid Application on the Full-Length Eyelid Margin," American Journal of Ophthalmology, vol. 142, No. 2, Aug. 2006, pp. 264-270.
Goto, E. et al., "Tear Evaporation Dynamics in Normal Subjects and Subjects with Obstructive Meibomian Gland Dysfunction," Investigative Ophthalmology abnd Visual Science, vol. 44, 2003, pp. 533-539.
Goto, E., et al. "Treatment of Non-Inflamed Obstructive Meibomian Gland Dysfunction by an Infrared Warm Compression Device" British Journal of Ophthalmology, BJO Online, http://www.bmjjournals.com/cgi/reprintform, vol. 26, 2002, 6 pages (pp. 1402-1407).
Goto, Eiki, et al. "Computer-Synthesis of an Interference Color Chart of Human Tear Lipid Layer, by a Colorimetric Approach" Investigative Ophthalmology & Visual Science, vol. 44, No. 11, Nov. 2003, 5 pages (pp. 4693-4697).
Goto, Eiki, et al., "Kinetic Analysis of Tear Interference Images in Aqueous Tear Deficiency Dry Eye Before and After Punctual Occlusion" Investigative Ophthalmology & Visual Science, vol. 44, No. 5, May 2003, 9 pages (pp. 1897-1905).
Goto, Eiki, M.D., "Quantification of Tear Interference Image; Tear Fluid Surface Nanotechnology" Cornea, vol. 23, Suppl. 1, Nov. 2004, 5 pages (pp. S20-S24).
Gravely, Ben, "Observations from TFA3" Aug. 2006, 4 pages.
Greiner, Jack V., et al., "Effect of Meibomian Gland Occlusion on Tear Film Lipid Layer Thickness" Lacrimal Gland, Tear Film, and Dry Eye Syndromes 2, Plenum Press, New York, 1998, 4 pages (pp. 345-348).
Greiner, Jack V., et al., "Meibomian Gland Phospholipids" Current Eye Research, Oxford University Press, 1995, 5 pages (pp. 371-375).
Greiner, Jack V., et al., "Volume of the Human and Rabbit Meibomian Gland System" Lacrimal Gland, Tear Film, and Dry Eye Syndromes 2, Plenum Pres, New York, 1998, 5 pages (pp. 339-343).
Guillon, J.P. et al., "Preocular Tear Film Characteristics of Nonwearers and Soft Contact Lens Wearers," Optometry and Vision Science, vol. 74, No. 5, 1997, pp. 273-279.
Guillon, J.P., "Tear Film Photography and Contact Lens Wear," Journal of the British Contact Lens Association, 1982, pp. 84-87.
Guillon, J.P., "The Tear Film Structure of the Contact Lens Wearer," Dept. of Optometry and Visual Science, City University, London, 1987, 398 pages.
Guillon, Jean-Pierre, "Non-Invasive Tearscope Plus Routine for Contact Lens Fitting," Contact Lens and Anterior Eye, (Supplement) 21, 1998, pp. S31-S40.
Guillon, Jean-Pierre, "Use of the Tearscope Plus and Attachments in the Routine Examination of the Marginal Dry Eye Contact Lens Patient," Lacrimal Gland, Tear Film, and Dry Eye Syndrome 2, 1998, pp. 859-867.
Hamilton, Dr. Roy C., "Ocular Explosion; a Dreaded Complication of Ophthalmic Regional Anaesthesia" Ophthalmic Anaesthesia News, Issue 4, Apr. 2001, 43 pages.
Hayreh, Sohan Singh, et al., "Parapapillary Chorioretinal Atrophy in Chronic High-Pressure Experimental Glaucoma in Rhesus Monkeys" Investigative Ophthalmology & Visual Science, vol. 39, No. 12, Nov. 1998, 8 pages (pp. 2296-1303).
Hellmuth, T. et al., "Non-Contact Measurement of the Optical Imaging Quality of an Eye," Proc. SPIE—Int. Soc. Opt. Eng. vol. 4431, 2001, pp. 52-58.
Hickson, Ian, "The Eye" Ian Hickson's Description of the Eye, http://academia.hixie.ch/bath/eye/home.html, 1998, 11 pages.
Author Unknown, Honan Balloon Intraocular Pressure Reducer with Valve—Complete, Ambler Surgical, Ambler Product No. HBC-120, Nov. 19, 2007, http://www.amblersurgical.com/store/product.cfm/pID:2456_5961E, 1 page.
Hosaka, Eri et al., "Interferometry in the Evaluation of Precorneal Tear Film Thickness in Dry Eye," American Journal of Opthalmology, vol. 151, No. 1, Jan. 2011, pp. 18-23.
International Search Report and Written Opinion for PCT/US2013/038116 mailed Sep. 12, 2013, 13 pages.
International Search Report and Written Opinion for PCT/US2013/038149 mailed Sep. 12, 2013, 18 pages.
International Search Report and Written Opinion for PCT/US2013/039395 mailed Oct. 11, 2013, 11 pages.
Ishida, Reiko et al., "Tear Film with 'Orgahexa Eyemasks' in Patients with Meibomian Gland Dysfunction," Optometry and Visions Science, vol. 85, No. 8, Aug. 2008, pp. E684-E691.
Iskander, D. Robert, PhD., et al., "Applications of High-Speed Videokeratoscopy" Clinical and Experimental Optometry, vol. 88, vol. 4, Jul. 2005, 9 pages (pp. 223-231).
Isreb, M.A. et al., "Correlation of Lipid Layer Thickness Measurements with Fluorescein Tear Film Breakup Time and Schirmer's Test," Eye, vol. 17, 2003, pp. 79-83.
Kaisheva, M et al., "Thin Liquid Films from Water-Based Dispersions of Cellulose Acethophthalate in the Presence of Pilocarpine Hydrochloride," J. Dispersion Sci. Technol., 1997.
Khamene, Ali, et al., "A Spectral-Discrimination Method for Tear-Film Lipid-Layer Thickness Estimation from Fringe Pattern Images" IEEE Transactions on Biomedical Engineering, vol. 47, No. 2, Jan. 2000, 10 pages (pp. 249-258).
Kilp, H. et al., "Tear Film Observation by Reflecting Microscopy and Differential Interference Contrast Microscopy," The Dry Eye Institute, Inc., 1986, pp. 564-569.
Kimball, S., et al., "Evidence for the major contribution of evaporation to tear film thinning between blinks," Investigative Ophthalmology and Visual Science, vol. 51, No. 12, Dec. 2010, http://www.iovs.org/content/51/12/6294.full.pdf+html, pp. 6294-6297.
King-Smith, P. Ewen et al., "The Thickness of the Human Precorneal Tear Film: Evidence from Reflection Spectra," Investigative Ophthalmology & Visual Science, Oct. 2000, vol. 41, No. 11, pp. 3348-3359.
King-Smith, P. Ewen, et al., "Application of a novel interferometric method to investigate the relation between lipid layer thickness and tear film thinning," Investigative Ophthalmology and Visual Science, vol. 51, No. 5, May 2010, http://www.iovs.org/content/51/5/2418.full.pdf+html, pp. 2418-2423.
King-Smith, P. Ewen, et al., "Evaporation from the Human Tear Film Studied by Interferometry" Lacrimal Gland, Tear Film, and Dry Eye Syndromes 3, Kluwer Academic/Plenum Publishers, 2002, 5 pages (pp. 425-429).
King-Smith, P. Ewen, et al., "Interferometric Imaging of the Full Thickness of the Precorneal Tear Film" J. Opt. Soc. Am. A, vol. 23, No. 9, Sep. 2006, 8 pages (pp. 2097-2104).
King-Smith, P. Ewen, et al., "Three Interferometric Methods for Measuring the Thickness of Layers of the Tear Film" Optometry and Vision Science, vol. 76, No. 1, Jan. 1999, 14 pages (pp. 19-32).

(56) References Cited

OTHER PUBLICATIONS

King-Smith, P.E. et al., "Can the Mucus Layer of the Tear Film be Demonstrated by Interferometry?," IOVS, vol. 45, Supp. 2, Apr. 2004, E-Abstract 3882. 2 pages.

King-Smith, P.E. et al., "Human Tear Film Breakup Studied by a New Imaging Interferometer: Preliminary Observations," IOVS, vol. 46, Supp. S, 2005, E-Abstract 4400, 2 pages.

Kojima, Takashi et al.., "A New Noninvasive Tear Stability Analysis System for the Assessment of Dry Eyes," Investigative Ophthalmology & Visual Science, May 2004, vol. 45, No. 5, pp. 1369-1374.

Korb, D. et al., "Lipid Layer Thickness Changes Following the Instillation of Two Novel Lubricant Eye Drops," IOVS, vol. 46, Supp. S, 2005, E-Abstract 2036, 2 pages.

Korb, Donald R. et al., "Meibomian Gland Diagnostic Expressibility: Correlation With Dry Eye Symptoms and Gland Location," Cornea, vol. 27, No. 10, Dec. 2008, pp. 1142-1147.

Korb, Donald R. et al., "Effect of Periocular Humidity on the Tear Film Lipid Layer," Cornea, vol. 15, No. 2, 1996, pp. 129-134.

Patel, S. et al., "Corneal Sensitivity and Some Properties of the Tear Film After Laser In Situ Keratomileusis," Journal of Refractive Surgery, Vo. 17, No. 1, 2001, pp. 17-24.

Patel, Sudi, PhD, FCOptom, Faao, et al., "Tear Meniscus Height, Lower Punctum Lacrimale, and Tear Lipid Layer in Normal Aging" Optometry and Vision Science, vol. 83, No. 10, Oct. 2006, 9 pages (pp. 732-739).

Paugh, J.R. et al., "White Light Tear Film Interferometry in Dry Eye Sub-Types," IOVS, vol. 45, Supp. 1, Apr. 2004, E-Abstract 93, 2 pages.

Pflugfelder, S.C. et al., "Evaluation of Subjective Assessments and Objective Diagnostic Tests for Diagnosing Tear-Film Disorders Known to Cause Ocular Irritation," Cornea, vol. 17, No. 1, 1998, pp. 38-56.

Pimenidi, M.K., et al., "Meibomian Gland Disfunction in Computer Vision Syndrome (abstract)," Annals of Ophthalmology (Vestn Oftalmol.) (Russia), Nov.-Dec. 2010, 126(6), http://www.medlit.ru/medeng/vof/vof10e0649.htm, 3 pages.

Primeau et al., "Interferometer for measuring the dynamic surface topography of a human tear film," Design and Quality for Biomedical Technologies V, vol. 8215, Feb. 2012, 11 pages.

Prydal, J.I. et al., "In Vivo Confocal Microscopy of the Cornea and Tear Film," Scanning, vol. 17, 1995, pp. 133-135.

Prydal, J.I. et al., "Study of Precorneal Tear Film Thickness and Structure by Interferometry and Confocal Microscopy," Investigative Ophthalmology and Visual Science, vol. 33, No. 6, May 1992, pp. 1996-2005.

Prydal, Jeremy I. et al., "Study of Human Precorneal Tear Film Thickness and Structure Using Laser Interferometry," Investigative Ophthalmology & Visual Science, vol. 33, No. 6, May 1992, pp. 2006-2011.

Remeseiro et al., "Automatic classification of the interferential tear film lipid layer using colour texture analysis," Computer Methods and Programs in Biomedicine, vol. 111, No. 1, Elsevier Ireland Ltd., Jul. 2013, pp. 93-103.

Rolando, M. et al., "The Dynamic Lipid Interference Pattern (DLIP) Test in Normal and Dry Eyes," IOVS, vol. 46, Supp. S, 2005, E-Abstract 4422, 2 pages.

Rolando, Maurizio et al., "New Test to Quantify Lipid Layer Behavior in Healthy Subjects and Patients with Keratoconjunctivitis Sicca," Cornea, vol. 27, No. 8, Sep. 2008, pp. 866-870.

Scaffidi, R.C. et al., "Lipid Layer Thickness and Dry Eye Symptoms," IOVS, vol. 46, Supp. S, 2005, E-Abstract 4444, 2 pages.

Schaumberg, D.A. et al., "Development and Validation of a Short Global Dry Eye Symptom Index," The Ocular Surface, vol. 5, No. 1, Jan. 2007, pp. 50-57.

Shiel, William C., Jr., MD, FACP, FACR, "Sjogren's Syndrome" MedicineNet.com, http:www.medicinenet.com, Sep. 2006, 3 pages.

Sullivan, David A., et al., "Androgen Influence on the Meibomian Gland" Investigative Ophthalmology & Visual Science, vol. 41, No. 12, Nov. 2000, 11 pages (pp. 3732-3742).

Sullivan, David A., et al., "Androgen Regulation of the Meibomian Gland" Lacrimal Gland, Tear Film, and Dry Eye Syndromes 2, Plenum Press, New York, 1998, 5 pages (pp. 327-331).

Szczesna-Iskander, D. et al., "Future Directions in Non-Invasive Measurements of Tear Film Surface Kinetics," Optometry and Vision Science, vol. 89, No. 5, May 2012 pp. 749-759.

Szczesna, D. et al., "Numerical Analysis of Interferograms of Tear Film Build-Up Time," Ophthalmic and Physiological Optics, vol. 29, No. 3, May 2009, pp. 211-218.

Szczesna, D., et al., "Predicting dry eye using noninvasive techniques of tear film surface assessment," Investigative Ophthalmology and Visual Science, vol. 52, No. 2, Feb. 2011, http://www.iovs.org/content/52/2/751.full.pdf+html, pp. 751-756.

Szczesna, D.H. et al., "Interferometric Measurements of the Tear Film Irregularities on the Human Cornea," Proceedings of the SPIE, vol. 5959, 2005, 10 pages.

Szczesna, Dorota H., et al., "Assessing Tear Film on Soft Contact Lenses With Lateral Shearing Interferometry," Eye & Contact Lens: Science & Clinical Practices, vol. 37, Issue 6, Nov. 2011, pp. 342-347.

Szczesna, Dorota H., et al., "Lateral Shearing Interferometry for Analysis of Tear Film Surface Kinetics," Optom. Vis. Sci., vol. 87, No. 7, Jul. 2010, pp. 513-517.

Szczesna, Dorota H., et al., "Robust estimation of tear film surface quality in lateral shearing interferometry," Journal of Biomedical Optics, vol. 14, No. 6, Nov./Dec. 2009, 4 pages.

Thai, Lee Choon, BSc, MCOptom, et al., "Contact Lens Drying and Visual Performance: The Vision Cycle with Contact Lenses" Optometry and Vision Science, vol. 79, No. 6, Jun. 2002, 8 pages (pp. 381-388).

Thai, Lee Choon, BSc, MCOptom, et al., "Effect of Contact Lens Materials on Tear Physiology" Optometry and Vision Science, vol. 81, No. 3, Mar. 2004, 11 pages (pp. 194-204).

Tomlinson, Alan, et al., "Reliability of Measurements of Tear Physiology" Lacrimal Gland, Tear Film, and Dry Eye Syndromes 3, Kluwer Academic/Plenum Publishers, 2002, 9 pages (pp. 1097-1105).

Tomlinson, Alan, et al., "Tear Film Osmolarity: Determination of a Referent for Dry Eye Diagnosis" Investigative Ophthalmology & Visual Science, vol. 47, No. 10, Oct. 2006, 7 pages (pp. 4309-4315).

Tseng, S.C. et al., "Changes of Lipid Tear Film in Dry Eye Patients and Normal Subjects Following One Drop of a New Emulsion Eye Drop Using Kinetic Analysis of Tear Interference Images," ARVO, vol. 44, 2003, E-Abstract 2457, 2 pages.

Uchida, A. et al., "Nonivasive Interference Tear Meniscometry in Dry Eye Patients with Sjogren Syndrome," Am. J. Ophthalmol., vol. 144, No. 2, Aug. 2007, pp. 232-237.

van Veen, R. L. P., et al., "Determination of VIS—NIR Absorption Coefficients of Mammalian Fat, with Time- and Spatially Resolved Diffuse Reflectance and Transmission Spectroscopy" Circa 2004, 3 pages.

Veres, A., et al., "Imaging lid-parallel conjunctival folds with OCT and comparing its grading with the slit lamp classification in dry eye patients and normal subjets," Investigative Ophthalmology and Visual Science, vol. 52, No. 6, May 2011, http://www.iovs.org/content/52/6/2945.full.pdf+html, pp. 2945-2951.

Wang, Jianhua et al., "Relationships between Central Tear Film Thickness and Tear Menisci of the Upper and Lower Eyelids" Investigative Ophthalmology & Visual Science, vol. 47, No. 10, Oct. 2006, 7 pages (pp. 4349-4355).

Wu, Dijia et al., "Sign Ambiguity Resolution for Phase Demodulation in Interferometry with Application to Prelens Tear Film Analysis," 2010 IEEE Computer Society Conference on Computer Visions and Pattern Recognition, CVPR 2010, 2010, pp. 2807-2814.

Wu, Dijia et al., "Texture Based Prelens Tear Film Segmentation in Interferometry Images," Machine Vision and Applications, vol. 21, No. 3, Apr. 2010, pp. 253-259.

Yokoi, N, et al., "Development of Automated Rheological Analysis for Tear Film Lipid Layer Spread Using the Cross-Correlation Method" Association for Research in Vision and Ophthalmology, 2007, 1 page.

(56) References Cited

OTHER PUBLICATIONS

Yokoi et al., "A Newly Developed Video-Meibography System Featuring a Newly Designed Probe," Japan Journal of Ophthalmology, vol. 51, Jan. 2007, pp. 53-56.
Yokoi, N. et al., "Assessment of Meibomian Gland Function in Dry Eye Using Meibometry," Arch. Ophthalmol., No. 117, Jun. 1999, pp. 723-729.
Yokoi, N. et al., "Correlation of Tear Lipid Layer Interference Patterns with the Diagnosis and Severity of Dry Eye," Amercian Journal of Ophthalmology, vol. 122, Dec. 1996, pp. 818-824.
Yokoi, N. et al., "New Instruments for Dry Eye Diagnosis," Seminars in Opthalmology, vol. 20, 2004, pp. 63-70.
Yokoi, Norihiko, et al., "Non-Invasive Methods of Assessing the Tear Film" Experimental Eye Research, vol. 78, Elsevier Ltd., 2003, 9 pages (pp. 399-407).
Young, G. et al., "Characteristics of the Pre-Lens Tear Films During Hydrogel Contact Lens Wear," Ophthal. Physiol. Opt., vol. 11, Jan. 1991, pp. 53-58.
Oculus, "Oculus Keratograph 5M Der Revolutionar," Oculus, 2 pages.
Bon, "Meibographie: mit der Phoenix Analyse-Software," bon Optic Vertriebsgesellschaft mbH, Nov. 2011, 4 pages.
Yokoi, N. et al., "Relationship between tear volume and tear meniscus curvature," Arch. Ophthalmology, vol. 122, Sep. 2004 ,pp. 1265-1269.
Notice of Allowance for U.S. Appl. No. 11/820,664 mailed May 27, 2010, 10 pages.
Notice of Allowance for U.S. Appl. No. 11/820,664 mailed Mar. 25, 2010, 10 pages.
Final Office Action for U.S. Appl. No. 11/820,664 mailed Dec. 29, 2009, 7 pages.
Non-final Office Action for U.S. Appl. No. 11/820,664 mailed Jun. 5, 2009, 9 pages.
Notice of Allowance for U.S. Appl. No. 12/633,057 mailed Jun. 9, 2011, 8 pages.
Final Office Action for U.S. Appl. No. 12/633,057 mailed Apr. 6, 2011, 6 pages.
Non-final Office Action for U.S. Appl. No. 12/633,057 mailed Aug. 19, 2010, 8 pages.
Notice of Allowance for U.S. Appl. No. 11/900,314 mailed Jan. 25, 2012, 7 pages.
Non-final Office Action for U.S. Appl. No. 11/900,314 Aug. 22, 2011, 26 pages.
Non-final Office Action for U.S. Appl. No. 12/798,325 mailed Jan. 27, 2012, 15 pages.
Non-final Office Action for U.S. Appl. No. 12/798,325 mailed Aug. 30, 2012, 16 pages.
Notice of Allowance for U.S. Appl. No. 12/798,325 mailed Feb. 15, 2013, 9 pages.
Notice of Allowance for U.S. Appl. No. 12/798,325 mailed May 29, 2013, 10 pages.
Notice of Allowance for U.S. Appl. No. 29/329,613 mailed Feb. 4, 2010, 7 pages.
Notice of Allowance for U.S. Appl. No. 29/329,613 mailed Nov. 13, 2009, 7 pages.
Non-Final Rejection mailed Apr. 20, 2012, for U.S. Appl. No. 12/798,275, 15 pages.
Final Office Action for U.S. Appl. No. 12/798,275 mailed Nov. 20, 2012, 16 pages.
Reply to Final Office Action for U.S. Appl. No. 12/798,275 filed Jan. 29, 2013, 6 pages.
Advisory Action for U.S. Appl. No. 12/798,275 mailed Feb. 5, 2013, 9 pages.
Non-final Office Action for U.S. Appl. No. 12/798,275 mailed Jul. 30, 2013, 15 pages.
Notice of Allowance for U.S. Appl. No. 12/798,326 mailed Aug. 29, 2011, 9 pages.
Non-final Office Action for U.S. Appl. No. 12/798,326 mailed Jun. 28, 2011, 19 pages.
Non-final Office Action for U.S. Appl. No. 12/798,326 mailed Mar. 29, 2011, 23 pages.
Notice of Allowance for U.S. Appl. No. 12/798,324 mailed Apr. 2, 2012, 9 pages.
Non-final Office Action for U.S. Appl. No. 12/798,324 mailed Dec. 15, 2011, 27 pages.
Non-final Office Action for U.S. Appl. No. 13/455,628 mailed Aug. 29, 2012, 18 pages.
Final Office Action for U.S. Appl. No. 13/455,628 mailed May 10, 2013, 9 pages.
Notice of Allowance for U.S. Appl. No. 13/455,628 mailed Jul. 12, 2013, 8 pages.
Translation of Notice of Rejection for Japanese patent application 2010-513285 mailed Nov. 6, 2012, 4 pages.
Non-final Office Action for U.S. Appl. No. 13/195,353 mailed May 3, 2013, 5 pages.
Notice of Allowance for U.S. Appl. No. 13/195,353 mailed Jul. 26, 2013, 9 pages.
Fagehi, Raied et al., "Contact Lens In Vitro Wettability by Interferometry Measures of Drying Dynamics," Eye & Contact Lens, vol. 39, No. 6, Contact Lens Association of Ophthalmologists, Nov. 2013, pp. 365-375.
Finis et al., "Evaluation of lipid layer thickness measurement of the tear film as a diagnostic tool for Meibomian gland dysfunction," Cornea, vol. 32, No. 12, Dec. 2013, Lippincott Williams & Wilkins, 5 pages.
Lu, Hui et al., "Combination of Optical Coherence Tomography and Reflectometry Technique for Eye Measurement," Proceedings of SPIE, vol. 8567, Ophthalmic Technologies XXII, 85672C, Mar. 26, 2013, 6 pages.
Lu, Hui et al., "Tear film measurement by optical reflectometry technique," Journal of Biomedical Optics, vol. 19, No. 2, Feb. 2014, 8 pages.
Primeau et al., "Interferometer and analysis methods for the in vitro characterization of dynamic fluid layers on contact lenses," Optical Engineering, vol. 51, No. 6, SPIE, Jun. 1, 2012, 9 pages.
Sweeney, Deborah F., et al., "Tear film stability: A review," Experimental Eye Research, vol. 117, Elsevier Ltd., Dec. 2013, pp. 28-38.
Szczesna, Dorota H. et al., "Interferometric measurements of dynamic changes of tear film," Journal of Biomedical Optics, vol. 11, No. 3, May 2006, 8 pages.
International Search Report and Written Opinion for PCT/US2013/077117 mailed Mar. 18, 2014, 34 pages.
Second Office Action for Chinese patent application 201080024927.9 issued Mar. 21, 2014, 15 pages.
Translation of Notice of Rejection for Japanese patent application 2010-513285 mailed Dec. 3, 2013, 8 pages.
Translation of Notice of Rejection for Japanese patent application 2012-503707 mailed Dec. 3, 2013, 3 pages.
Notice of Allowance for U.S. Appl. No. 12/798,275 mailed Jan. 2, 2014, 8 pages.
Author Unknown, "Tomey's RT-7000 is new and improved," Instruments—New Product Gallery, Vision Care Product News (VCPN), Jul. 2008, 1 page.
Author Unknown, "Tearscope Plus: Introduction and guided tour to the benefits of the Keeler Tearscope-plus," Keeler Instruments, bon Optic, created Jan. 24, 2006, www.bon.de/download/TearscopeE.pdf, 22 pages.
Australian Patent Examination Report No. 1 for Australian patent application 2011235961, mailed Jan. 2, 2013, 3 pages.
Alonso-Caneiro, D. et al., "Context-Based Modelling of Interferometric Signals for the Assessment of Tear-Film Surface Quality," 2009 IEEE/SP 15th Workshop on Statistical Signal Processing (SSP), 2009, pp. 553-556.
An, Yang et al., "Contrast Sensitivity Measurement in Dry Eyes," Int J Ophthalmol, vol. 10, No. 3, Mar. 2010, pp. 488-491.
Arndt, G. Dickey et al., "Microwave Treatment of Prostate Cancer and Hyperplasia," NASA Tech Briefs, Jun. 2005, 1 page.
Author Unknown, "Blepharitis," The Eye Digest, The Dry Eye Research Center, University of Illinois at Chicago, 2003, 3 pages.
Author Unknown, "Introduction to the Report of the International Dry Eye WorkShop (2007)," The Ocular Surface, vol. 5, No. 2, Apr. 2007, pp. 69-70.

(56) References Cited

OTHER PUBLICATIONS

Author Unknown, "Keratoconjunctivitis Sicca" Wikipedia, http://en.wikipedia.org/wiki/keratoconjunctivitis_sicca, Nov. 2006, 4 pages.
Author Unknown, "Measurement of Intraocular Pressure" Biomedical Foundations of Ophthalmology, Intraocular Pressure, vol. 2, Chapter 7, Circa 1982, 6 pages (pp. 11-16).
Author Unknown, "Thermographic Camera" Wikipedia, http://en.wikipedia.org/wiki/thermographic_camera, Sep. 2006, 4 pages.
Bartlett, Hannah, et al. "New Perspectives on the Investigation and Treatment of Dry Eye Syndrome—Part 1" Optician, vol. 231, No. 6038, Feb. 2006, 9 pages (pp. 27-37).
Begley, Carolyn, G., et al., "Relationship Between Symptom Profile and Clinical Signs Among Dry Eye Patients" Circa 2003, 1 page.
Begley, Carolyn, G., et al., "The Relationship Between Habitual Patient-Reported Symptoms and Clinical Signs among Patients with Dry Eye of Varying Severity" Investigative Ophthalmology & Visual Science, vol. 44, No. 11, Nov. 2003, 9 pages (pp. 4753-4761).
Behrens, Ashley, MD, "Interferometry for the Detection of Dry Eye," Cataract & Refractive Surgery Today Europe, Nov./Dec. 2008. pp. 57-58.
Behrens, Ashley, MD, "Multiwave Interferometry is Creating a New Understanding of the Tear Film," Refractive Eyecare, Oct. 2009, from www.refractiveeyecare.com, 5 pages.
Berliner, M. L., M.D., "The Margins of the Eyelid" Chapter Eight, Biomicroscopy of the Eye, Slit Lamp Microscopy of the Living Eye, vol. 1, Medical Book Department of Harper & Brothers, NYC, Paul B. Hoeber, Inc., 1949, 5 pages (pp. 252-257).
Blackie, Caroline et al., "The Relationship Between Dry Eye Symptoms and Lipid Layer Thickness," Cornea, vol. 28, No. 7, Aug. 2009, pp. 789-794.
Borchman, Douglas, et al., "Temperature-Induced Conformational Changes in Human Tear Lipids Hydrocarbon Chains" Biopolymers, vol. 87, No. 2-3, Jun. 13, 2007, pp. 124-133 (10 pages).
Boyer, Kim L. et al., "Resilient Subclass Discriminant Analysis with Application to Prelens Tear Film Interferometry," Proceedings, Lecture Notes in Computer Science, vol. 6718/2011, MCPR, Cancun, Mexico, Jun. 29-Jul. 2, 2011, pp. 1-11.
Bron, A.J. et al., "Functional Aspects of the Tear Film Lipid Layer," Experimental Eye Research, vol. 78, 2004, pp. 347-360.
Bron, A.J. et al., "The Contribution of Meibomian Disease to Dry Eye," Ocul. Surf., vol. 2, 2004, pp. 149-164.
Bron, Anthony J., BSc, FRCS, FCOphth, et al., "The Ocular Appendages: Eyelids, Conjunctiva and Lacrimal Apparatus" Chapter 2, Wolff's Anatomy of the Eye and Orbit, Eighth Edition, Chapman & Hall Medical, Jan. 1997, 12 pages (pp. 30-42).
Carrington, S. D., et al., "Polarized Light Biomicroscopic Observations on the Pre-Corneal Tear Film" J. Small Anim. Pract., vol. 28, 1987, 20 pages (pp. 605-622).
Craig, J.P. et al. "Importance of the Lipid Layer in Human Tear Film Stability and Evaporation," Optometry and Visual Science, vol. 70, No. 1, 1997, pp. 8-14.
Cruz, Daniele, "Dry Eye Syndrome More Widespread than Predicted" Ocular Surgery News, U.S. Edition, May 2007, 1 page.
Cruz, Daniele, "Surgeon: Early Treatment Key to Avoiding Dry Eye Progression" Ocular Surgery News, U.S. Edition, May 2007, 1 page.
Danjo, Yukitaka, et al., "Measurement of the Precorneal Tear Film Thickness with a Non-Contact Optical Interferometry Film Thickness Measurement System" Jpn J Ophthal., vol. 38, 1994, 7 pages (pp. 260-266).
De Paiva, Cintia S., et al., "Diagnostic Approaches to Lacrimal Keratoconjunctivitis," Dry Eye and Ocular Surface Disorders, New York, NY: Marcel Dekker, 2004, pp. 269-270.
Di Pascuale, Mario A., M.D., et al., "Lipid Tear Deficiency in Persistent Dry Eye After Laser In Situ Keratomileusis and Treatment Results of New Eye-Warming Device" J Cataract Refract. Surg., vol. 31, ASCRS and ESCRS, Elsevier Inc., 2005, 9 pages (pp. 1741-1749).
Di Pascuale, Mario A., M.D., et al., "Sequential Changes of Lipid Tear Film after the Instillation of a Single Drop of a New Emulsion Eye Drop in Dry Eye Patients" American Academy of Ophthalmology, vol. 111, 2004, 9 pages (pp. 783-791).
Doane, Marshall G., "Abnormalities of the Structure of the Superficial Lipid Layer on the In Vivo Dry-Eye Tear Film" (and critique of same) Lacrimal Gland, Tear Film, and Dry Eye Syndromes, Plenum Press, New York, 1994, 11 pages (pp. 489-493).
Doane, Marshall G., "An Instrument for In Vivo Tear Film Interferometry" (and critique of same), Optometry and Vision Science, vol. 66, No. 6, 1989, 10 pages (pp. 383-388).
Doane, Marshall G., et al., "Tear Film Interferometry as a Diagnostic Tool for Evaluating Normal and Dry-Eye Tear Film" Lacrimal Gland, Tear Film, and Dry Eye Syndromes 2, Plenum Press, New York, 1998, 7 pages (pp. 397-303).
Dogru, M. et al., "New Insights into the Diagnosis and Treatment of Dry Eye," Ocular Surface, vol. 2, No. 2, 2004, pp. 59-74.
Dogru, M. et al., "Strip Meniscometry: A New and Simple Method of Tear Meniscus Evaluation," Invest. Ophthalmol. Vis. Sci., vol. 47, No. 5, May 2006, pp. 1895-1901.
Driver, Paul J., et al., "Meibomian Gland Dysfunction" Major Review, Survey of Ophthalmology, vol. 40, No. 5, Mar.-Apr. 1996, 25 pages (pp. 343-367).
Dubra, Alfredo, et al., "Double Lateral Shearing Interferometer for the Quantitative Measurement of Tear Film Topography" Applied Optics, vol. 44, No. 7, Mar. 2005, 9 pages (pp. 1191-1199).
Elizondo, A.E. et al., "Detection of Blink Related Microtrauma by Kinetic Analysis of Tear Interference Images in Patients with Steven Johnson Syndrome and Toxic Epidermal Necrolysis Syndrome," IOVS, vol. 46, Supp. S, 2005, E-Abstract 2654, 2 pages.
English translation of Japanese patent application announcement 2007-209370, 14 pages.
Eom et al., "Correlation Between Quantitative Measurements of Tear Film Lipid Layer Thickness and Meibomian Gland Loss in Patients with Obstructive Meibomian Gland Dysfunction and Normal Controls," American Journal of Ophthalmology, Jun. 2013, vol. 155, No. 6, Elsevier Inc., pp. 1104-1110.
Ernest, J. Terry, M.D. et al., "Ocular Massage Before Cataract Surgery" Tr. Am. Ophth. Soc., vol. LXXXIII, 1985, 13 pages (pp. 205-217).
European Search Report issued Jan. 20, 2012, for European Patent Application No. 11183259.8, 7 pages.
European Search Report for patent application 08732520.5 mailed Feb. 24, 2012, 8 pages.
Extended European Search Report and Written Opinion for patent application 10759411.1-1657 mailed May 14, 2013, 9 pages.
Examination Report for European patent application 11183259.8-1657 mailed May 8, 2013, 7 pages.
Fanning, Gary L., M.D., "Ocular Compression: A Review," OASIS Newsletter, Ophthalmic Anesthesia Society, Summer 2006, http://www.eyeanesthesia.org/newsletter/pdf/oasis_summer06.pdf, 7 pages.
Fenimore, C.P., et al., "Assessment of Resolution and Dynamic Range for Digital Cinema" National Institute of Standards and Technology, Gaithersburg, MD, Circa 2002, 8 pages.
Finlayson, Graham, et al., "Hue that is Invariant to Brightness and Gamma" School of Information Systems, University of East Anglia, Norwich, United Kingdom, Circa 2002, 9 pages (pp. 303-312).
First Office Action for Chinese patent application 201080024927.9 mailed May 13, 2013, 16 pages.
Korb, Donald R. et al., "Increase in Tear Film Lipid Layer Thickness Following Treatment of Meibomian Gland Dysfunction," Adv. Exp. Med. Biol., vol. 350, 1994, pp. 293-298.
Korb, Donald R. et al., "Tear Film Lipid Layer Thickness as a Function of Blinking," Cornea, vol. 13, No. 4, 1994, pp. 354-359.
Korb, Donald R. O.D., et al., "Comparison of Fluorescein Break-Up Time Measurement Reproducibility Using Standard Fluorescein Strips Versus the Dry Eye Test (DET) Method," Cornea, vol. 20(8), Philadelphia, 2001, 8 pages.
Korb, Donald R., "Alleviation of Computer-Induced Eye Discomfort Syndrome and Associated Lipid Layer Changes," Lacrimal Gland, Tear Film, and Dry Eye Syndrome 3, 2002, pp. 501-506.
Korb, Donald R., "The Tear Film—Its Role Today and in the Future," 2002, 52 pages.

(56) References Cited

OTHER PUBLICATIONS

Korb, Donald R., et al., "Human and Rabbit Lipid Layer and Interference Pattern Observations," Lacrimal Gland, Tear Film, and Dry Eye Syndromes 2, Plenum Press, New York, 1998, pp. 305-308.

Korb, Donald R., et al., "Tear Film Lipid Layer Formation: Implications for Contact Lens Wear," Review, Optometry and Vision Science, vol. 73, No. 3, 1996, pp. 189-192.

Korb, Donald R., et al., "The Effects of Anionic and Zwitterionic Phospholipids on the Tear Film Lipid Layer," Lacrimal Gland, Tear Film, and Dry Eye Syndromes 3, Kluwer Academic/Plenum Publishers, 2002, pp. 495-499.

Korb, Donald R., et al., "The Tear Film Structure, Function and Clinical Examination," British Contact Lens Association, Butterworth Heinemann, Circa 1999, pp. 154-179.

Korb, Donald R., O.D. et al., "The Phenomenon of Central Circular Clouding; the loss of corneal transparency unique to contact lens practice requiring specialized techniques for early recognition," Journal of American Optometric Association, vol. 39, No. 3, Mar. 1968, pp. 223-230.

Korb, Donald R., O.D., et al., "Lid Wiper Epitheliopathy and Dry Eye Syndrome," Eye & Contact Lens, vol. 31, No. 1, 2005, pp. 2-8.

Korb, Donald R., O.D., et al., "Meibomian Gland Dysfunction and Contact Lens Intolerance" Jnl American Optometric Association, vol. 51, No. 3, Mar. 1980, 9 pages (pp. 243-251).

Korb, Donald R., OD, et al., "A Device to Standardize and Quantify the Force Used to Diagnose Meibomian Gland Obstruction and Dysfunction" 2007, 1 page.

Korb, Donald R., OD, et al., "A New Device for the Diagnosis of Meibomian Gland Dysfunction and Obstruction" 2007, 1 page.

Korb, Donald, "Survey of Preferred tests for Diagnosis of the Tear Film and Dry Eye," Cornea, vol. 19, 2000, pp. 483-486.

Kowalik, W. et al., "Corneal Topography Measurement of the Eye by Means of Radial Shearing Interferometer," Proc. SPIE—Int. Soc. Opt. Eng. vol. 4356, 2001. pp. 375-380.

Kronemyer, Bob, "Dry Eye Experts Unveil New Treatment Guidelines, Terminology" Ocular Surgery News, U.S. Edition, May 2007, 1 page.

Leibovitch, Larry S., Ph.D., "The Shape of the Eye: Why the Eye is Round" Florida Atlantic University, Boca Raton, FL, Circa 1986, 28 pages (pp. 1-27).

Licznerski, T.J. et al., "Application of Twyman-Green Interferometer for Evaluation of In Vivio Breakup Characteristic of the Human Tear Film," Journal of Biomedical Optics, vol. 4, No. 1, Jan. 1999, pp. 176-182.

Licznerski, T.J. et al., "Interference and Model Study of the Human Tear Film," Politechnika Wroclawska, Source DAI-C 60/04, Winter 1999, p. 782 (Abstract only).

Licznerski, T.J. et al., "Novel Double Path Shearing Interferometer in Corneal Topography Measurements," Proceedings of the SPIE, vol. 5959, 2005, 6 pages.

Licznerski, Tomasz J., et al., "Analysis of Shearing Interferograms of Tear Film Using Fast Fourier Transforms" Journal of Biomedical Optics, vol. 3, No. 1, Jan. 1998, pp. 32-37.

Lopez Garcia, J.S. et al., "Measure of the Fatty Layer Thickness of Precorneal Tear Film by Interference Colours in Different Types of Dry Eye," Sociedad Espanola de Oftalmologia, vol. 78, Part 5, Jan. 2003, pp. 257-264.

Lorentz, Holly Irene, "Lipid Deposition on Hydrogel Contact Lenses" Master's Thesis, University of Waterloo, Ontario, Canada, 2006, 175 pages.

Loveridge, Ron, "Effective Management of Induced Dry Eye Syndrome with Soft CLs" www.optometry.co.uk, Apr. 2000,pp. 35-38.

Lui, Haixia, MD, et al., "Temporal Progression and Spatial Repeatability of Tear Breakup" Optometry and Vision Science, vol. 83, No. 10, Oct. 2006, pp. 723-730.

Mathers, W.D., "Assessment of the Tear Film with Tandem Scanning Confocal Microscopy," Cornea, vol. 16, No. 2, 1997, pp. 162-168.

Mathers, W.D., "Ocular Evaporation in Meibomian Gland Dysfunction and Dry Eye," Ophthalmology, vol. 100, No. 3, Mar. 1993, pp. 347-351.

Matsumoto, Yukihiro, et al., "Efficacy of a New Warm Moist Air Device on Tear Functions of Patients with Simple Meibomian Gland Dysfunction" Cornea, vol. 25, No. 6, Jul. 2006, 1 page.

McCarty, C.A. et al., "The Epidemiology of Dry Eye in Melbourne, Australia," Ophthalmology, vol. 105, No. 6, Jun. 1998, pp. 1114-1119.

McDonald, James E., "Surface Phenomena of the Tear Films," Tr. Am. Opth. Soc., vol. 66, 1968, pp. 905-939.

McGrath, Dermot, "Iris diaphragm IOLs safe and effective in treating aniridia," EuroTimes, European Society of Cataract & Refractive Surgeons, May 2007, http://www.escrs.org/PUBLICATIONS/EUROTIMES/07MAY/IRISDIAPHRAGMIOLS.PDF, p. 42.

Miano, Fausto, et al., "Interface Properties of Simplified Tear-Like Fluids in Relation to Lipid and Aqueous Layers Composition" Lacrimal Gland, Tear Film, and Dry Eye Syndromes 3, Kluwer Academic/Plenum Publishers, 2002, 13 pages (pp. 405-417).

Millar, et al., "Analysis of comparison of human meibomian lipid films and mixtures with cholestryl esters in vitro films using high resolution color microscopy," Cornea, vol. 53, No. 8, Jul. 2012, pp. 4710-4719.

Miller, David "Pressure of the Lid on the Eye" Arch. Opthalmology, vol. 78, 1967, 7 pages (pp. 382-330).

Mitra, M. et al., "Tear Film Lipid Layer Thickness and Ocular Comfort after Meibomian Therapy via Latent Heat with a Novel Device in Normal Subjects" Eye, vol. 19, 2005, 4 pages (pp. 657-660).

Mori, Asako, M.D., et al., "Efficacy and Safety of Infrared Warming of the Eyelids" Cornea, vol. 18(2), 1999, 6 pages (pp. 188-193).

Nichols, Jason J., et al., "The Impact of Hydrogel Lens Settling on the Thickness of the Tears and Contact Lens" Investigative Ophthalmology & Visual Science, vol. 45, No. 8, Aug. 2004, pp. 2549-2554.

Nichols, Jason J., et al., "The Thickness of the Post-Lens Tear Film Measured by Interferometry" Lacrimal Gland, Tear Film, and Dry Eye Syndromes 3, Kluwer Academic/Plenum Publishers, 2002, pp. 929-933.

Nichols, Jason J., et al., "Thickness of the Pre- and Post-Contact Lens Tear Film Measured In Vivo by Interferometry" Investigative Ophthalmology & Visual Science, vol. 44, No. 1, Jan. 2003, pp. 68-77.

Nichols, Jason J., OD, MS, Faao, et al., "Evaluation of Tear Film Interference Patterns and Measures of Tear Break-Up Time" Optometry and Vision Science, vol. 79, No. 6, Jun. 2002, pp. 363-369.

Nichols, Jason J., OD, MS, MPH, et al., "The Effect of Eye Closure on the Post-Lens Tear Film Thickness During Silicone Hydrogel Contact Lens Wear" Cornea, vol. 22, No. 6, 2003, pp. 539-544.

Nichols, K.K. et al., "The Lack of Association Between Signs and Symptoms in Patients with Dry Eye Disease," Cornea, vol. 23, No. 8, Nov. 2004, pp. 762-770.

Nichols, K.K. et al., "The Repeatability of Clinical Measurements of Dry Eye," Cornea, vol. 23, No. 3, Apr. 2004, pp. 272-285.

Norn, M.S., "Semiquantitative Interference Study of Fatty Layer of Precorneal Film," ACTA Ophthalmologica, vol. 57, 1979, pp. 766-774.

Corrected Notice of Acceptance for Australian patent application 2011235961 mailed Sep. 19, 2013, 2 pages.

Notice of Acceptance for Australian patent application 2011235961 mailed Sep. 11, 2013, 2 pages.

Ohashi, Yoshiki, et al., "Laboratory Findings in Tear Fluid Analysis," Clinica Chimica Acta 369, 2006, 12 pages (pp. 17-28).

Olson, Mary Catherine, B.A., et al., "Increase in Tear Film Lipid Layer Thickness Following Treatment with Warm Compresses in Patients with Meibomian Gland Dysfunction" Eye & Contact Lens, vol. 29(2), 2003, 6 pages.

Ong, B. L., et al., "Meibomian Gland Dysfunction: Some Clinical, Biochemical and Physical Observations" Ophthal. Physiol. Opt., vol. 10, Apr. 1990, 5 pages (pp. 144-148).

King-Smith, P.E. et al., "Tear film interferometry and corneal surface roughness," Investigative Ophthalmology & Visual Science, vol. 55, No. 4, Apr. 1, 2014, Association for Research in Vision and Ophthalmology Inc., pp. 2614-2618.

Qazi, Yureeda et al., "Image-guided evaluation and monitoring of treatment response in patients with dry eye disease," Graefe's Archive for Clinical and Experimental Ophthalmology, vol. 252, Issue 6, Jun. 2014, Springer Verlag, pp. 857-872.

(56) References Cited

OTHER PUBLICATIONS

Wu, Yuan et al., "Correlation between measurement of tear meniscus by anterior segment module of OCT with dry eye signs and symptoms," Chinese Journal of Experimental Ophthalmology, vol. 32, No. 6, Jun. 2014, Henan Institute of Ophthalmology, pp. 541-545.

Notice of Allowance for U.S. Appl. No. 13/870,054 mailed Jul. 17, 2014, 9 pages.

Lam, Sin Man et al., "Longitudinal changes in tear fluid lipidome brought about by eyelid-warming treatment in a cohort of meibomian gland dysfunction," Journal of Lipid Research, vol. 55, No. 9, Sep. 2014, American Society for Biochemistry and Molecular Biology, Inc., pp. 1959-1969.

Szczesna et al., "Application of interferometry for evaluation of the effect of contact lens material on tear film quality," Proceedings of SPIE, vol. 7064, Aug. 11, 2008, SPIE, 9 pages.

International Search Report and Written Opinion for PCT/US2014/036636, mailed Oct. 2, 2014, 9 pages.

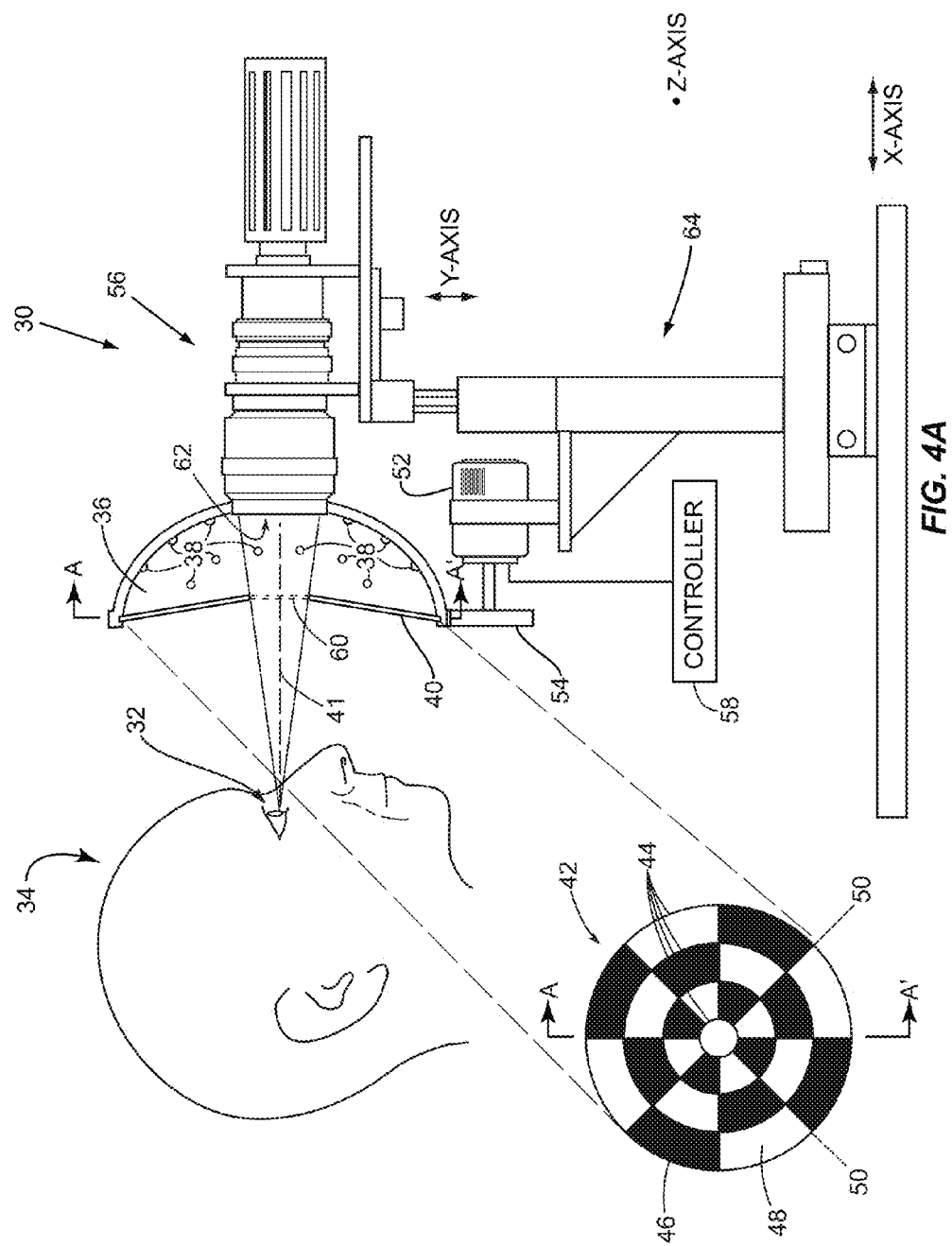

FULL-EYE ILLUMINATION OCULAR SURFACE IMAGING OF AN OCULAR TEAR FILM FOR DETERMINING TEAR FILM THICKNESS AND/OR PROVIDING OCULAR TOPOGRAPHY

PRIORITY APPLICATIONS

The present application claims priority to U.S. Provisional Patent Application No. 61/745,213 entitled "FULL-EYE ILLUMINATION OCULAR SURFACE IMAGING OF AN OCULAR TEAR FILM FOR DETERMINING TEAR FILM THICKNESS AND/OR PROVIDING OCULAR TOPOGRAPHY" filed Dec. 21, 2012, which is incorporated herein by reference in its entirety.

The present application is a continuation-in-part patent application of U.S. patent application Ser. No. 12/798,325 entitled "OCULAR SURFACE INTERFEROMETRY (OSI) METHODS FOR IMAGING, PROCESSING, AND/OR DISPLAYING AN OCULAR TEAR FILM," filed Apr. 1, 2010, which claims priority to U.S. Provisional Patent Application Ser. No. 61/211,596 entitled "OCULAR SURFACE INTERFEROMETRY (OSI) DEVICES, SYSTEMS, AND METHODS FOR MEASURING TEAR FILM LAYER THICKNESS(ES)," filed on Apr. 1, 2009, which are both incorporated herein by reference in their entireties.

The present application is also a continuation-in-part patent application of U.S. patent application Ser. No. 12/798,275 entitled "OCULAR SURFACE INTERFEROMETRY (OSI) DEVICES FOR IMAGING, PROCESSING, AND/OR DISPLAYING AN OCULAR TEAR FILM," filed Apr. 1, 2010, which claims priority to U.S. Provisional Patent Application Ser. No. 61/211,596 entitled "OCULAR SURFACE INTERFEROMETRY (OSI) DEVICES, SYSTEMS, AND METHODS FOR MEASURING TEAR FILM LAYER THICKNESS(ES)," filed on Apr. 1, 2009, which are both incorporated herein by reference in their entireties.

RELATED APPLICATIONS

The present application is related to U.S. patent application Ser. No. 11/820,664 entitled "TEAR FILM MEASUREMENT," filed on Jun. 20, 2007, now issued U.S. Pat. No. 7,758,190, which is incorporated herein by reference in its entirety.

The present application is also related to U.S. patent application Ser. No. 12/633,057 entitled "TEAR FILM MEASUREMENT," filed on Dec. 8, 2009, now issued U.S. Pat. No. 7,988,294, which is incorporated herein by reference in its entirety.

The present application is also related to U.S. patent application Ser. No. 13/195,353 entitled "TEAR FILM MEASUREMENT," filed on Aug. 1, 2012, which is incorporated herein by reference in its entirety.

The present application is also related to U.S. patent application Ser. No. 11/900,314 entitled "TEAR FILM MEASUREMENT," filed on Sep. 11, 2007, now issued U.S. Pat. No. 8,192,026, which is incorporated herein by reference in its entirety.

The present application is also related to U.S. patent application Ser. No. 13/455,628 entitled "TEAR FILM MEASUREMENT," filed on Apr. 25, 2012, which is incorporated herein by reference in its entirety.

The present application is also related to U.S. patent application Ser. No. 12/798,326 entitled "OCULAR SURFACE INTERFEROMETRY (OSI) METHODS FOR IMAGING AND MEASURING OCULAR TEAR FILM LAYER THICKNESS(ES)," filed Apr. 1, 2010, now issued U.S. Pat. No. 8,092,023, which is incorporated herein by reference in its entirety.

The present application is also related to U.S. patent application Ser. No. 12/798,324 entitled "OCULAR SURFACE INTERFEROMETRY (OSI) DEVICES AND SYSTEMS FOR IMAGING AND MEASURING OCULAR TEAR FILM LAYER THICKNESS (ES)," filed Apr. 1, 2010, now issued U.S. Pat. No. 8,215,774, which is incorporated herein by reference in its entirety.

The present application is also related to U.S. Provisional Patent Application Ser. No. 61/638,231 entitled "APPARATUSES AND METHODS OF OCULAR SURFACE INTERFEROMETRY (OSI) EMPLOYING POLARIZATION AND SUBTRACTION FOR IMAGING, PROCESSING, AND/OR DISPLAYING AN OCULAR TEAR FILM" filed Apr. 25, 2012, which is incorporated herein by reference in its entirety.

The present application is also related to U.S. Provisional Patent Application Ser. No. 61/638,260 entitled "BACKGROUND REDUCTION APPARATUSES AND METHODS OF OCULAR SURFACE INTERFEROMETRY (OSI) EMPLOYING POLARIZATION FOR IMAGING, PROCESSING, AND/OR DISPLAYING AN OCULAR TEAR FILM" filed Apr. 25, 2012, which is incorporated herein by reference in its entirety.

The present application is being filed with color versions (3 sets) of the drawings discussed and referenced in this disclosure. Color drawings more fully disclose the subject matter disclosed herein. The colors as transmitted, displayed, and/or printed are subject to individual display limitations and cannot be expected to be an accurate representation(s); these are intended for illustrative and instructional purposes.

FIELD OF THE DISCLOSURE

The technology of the disclosure relates to imaging an ocular tear film. The technology of the disclosure also relates to measuring ocular tear film layer thickness(es), including lipid layer thickness (LLT) and/or aqueous layer thickness (ALT). Imaging the ocular tear film and measuring tear film layer thickness (TFLT) may be used to diagnose "dry eye," which may be due to any number of deficiencies, including lipid deficiency and aqueous deficiency.

BACKGROUND

A mammalian eye includes a cornea and sclera. The sclera provides a structure for the eye that gives the eye a generally spherical shape. The sclera also gives the major surface portion of the eye its white color. The cornea is a transparent front part of the eye that covers an iris, a pupil, and an anterior chamber that is disposed in front of a lens. Light passes through the transparent cornea and then through the pupil to fall upon a retina that senses the passed light. Together, the retina and a brain produce vision. Clinicians are concerned with the proper function and health of the eye.

The function of the eye can be affected by aberrations to the shape of the cornea. Therefore, clinical diagnosis of vision will benefit from capturing and displaying a corneal topography image. In essence, corneal topography is a non-invasive procedure used to determine the shape and integrity of the cornea of the eye. During a corneal topography, a clinician projects a series of illuminated rings known as a Placido pattern onto the surface of the cornea. The Placido pattern is reflected back into a computerized camera system. Typically, the computerized camera system analyzes the reflected Placido pattern to generate a topographical map of the cornea. The resulting corneal topographic images are analyzed by the clinician to determine the health of the eye. For example, corneal topography is used to analyze corneas before and after vision correction surgery and for contact lens fitting, etc. It is known that a contact lens fitting that is too tight interferes with natural tear flow. Therefore, it is important to provide a precorneal tear film analysis after a contact lens fitting.

In this regard, clinical analysis of the precorneal tear film can be provided to improve eye health and provide comfortable vision. In the human eye, the precorneal tear film covering ocular surfaces is composed of three primary layers: the mucin layer, the aqueous layer, and the lipid layer. Each layer plays a role in the protection and lubrication of the eye and thus affects dryness of the eye or lack thereof. Dryness of the eye is a recognized ocular disease, which is generally referred to as "dry eye," "dry eye syndrome" (DES), or "keratoconjunctivitis sicca" (KCS). Dry eye can cause symptoms, such as itchiness, burning, and irritation, which can result in discomfort. There is a correlation between the ocular tear film layer thicknesses and dry eye disease. The various different medical conditions and damage to the eye, as well as the relationship of the aqueous and lipid layers to those conditions are reviewed in Surv Opthalmol 52:369-374, 2007 and additionally briefly discussed below.

As illustrated in FIG. 1, the precorneal tear film includes an innermost layer of the tear film in contact with a cornea 10 of an eye 12 known as the mucus layer 14. The mucus layer 14 is comprised of many mucins. The mucins serve to retain aqueous matter in the middle layer of the tear film known as the aqueous layer. Thus, the mucus layer 14 is important in that it assists in the retention of aqueous matter on the cornea 10 to provide a protective layer and lubrication, which prevents dryness of the eye 12.

A middle or aqueous layer 16 comprises the bulk of the tear film. The aqueous layer 16 is formed by secretion of aqueous matter by lacrimal glands 18 and accessory tear glands 20 surrounding the eye 12, as illustrated in FIG. 2. The aqueous matter, secreted by the lacrimal glands 18 and accessory tear glands 20, is also commonly referred to as "tears." One function of the aqueous layer 16 is to help flush out any dust, debris, or foreign objects that may get into the eye 12. Another important function of the aqueous layer 16 is to provide a protective layer and lubrication to the eye 12 to keep it moist and comfortable. Defects that cause a lack of sufficient aqueous matter in the aqueous layer 16, also known as "aqueous deficiency," are a common cause of dry eye. Contact lens wear can also contribute to dry eye. A contact lens can disrupt the natural tear film and can reduce corneal sensitivity over time, which can cause a reduction in tear production.

The outermost layer of the tear film, known as the "lipid layer" 22 and illustrated in FIG. 1, also aids to prevent dryness of the eye. The lipid layer 22 is comprised of many lipids known as "meibum" or "sebum" that are produced by meibomian glands 24 in upper and lower eyelids 26, 28, as illustrated in FIG. 3. This outermost lipid layer is very thin, typically less than 250 nanometers (nm) in thickness. The lipid layer 22 provides a protective coating over the aqueous layer 16 to limit the rate at which the aqueous layer 16 evaporates. Blinking causes the upper eyelid 26 to mall up aqueous matter and lipids as a tear film, thus forming a protective coating over the eye 12. A higher rate of evaporation of the aqueous layer 16 can cause dryness of the eye. Thus, if the lipid layer 22 is not sufficient to limit the rate of evaporation of the aqueous layer 16, dryness of the eye may result.

Notwithstanding the foregoing, it has been a long standing and vexing problem for clinicians and scientists to quantify the lipid and aqueous layers and any deficiencies of same to diagnose evaporative tear loss and/or tear deficiency dry eye conditions. Further, many promising treatments for dry eye have failed to receive approval from the United States Food and Drug Administration due to the inability to demonstrate clinical effectiveness to the satisfaction of the agency. Many clinicians diagnose dry eye based on patient symptoms alone. Questionnaires have been used in this regard. Although it seems reasonable to diagnose dry eye based on symptoms alone, symptoms of ocular discomfort represent only one aspect of "dry eyes," as defined by the National Eye Institute workshop on dry eyes. In the absence of a demonstrable diagnosis of tear deficiency or a possibility of excessive tear evaporation and damage to the exposed surface of the eye, one cannot really satisfy the requirements of dry eye diagnosis.

SUMMARY OF THE DETAILED DESCRIPTION

Full-eye illumination ocular surface imaging of ocular tear films for determining tear film thickness and/or providing ocular topography are disclosed herein. Full-eye imaging means illuminating the eye and/or ocular tear film with an elliptical or circular-shaped lighting pattern because of the generally circular shape of the cornea. Full-eye illumination does not require that the entire eye is illuminated, but rather a general elliptical or circular pattern illumination is provided to illumination a greater portion of the eye as opposed to other patterns of eye illumination, including square or rectangle pattern illumination. Providing full-eye illumination for TFLT and/or ocular topography analysis can provide certain advantages over other patterns of eye illumination. However, there is a central region for a lens viewing opening that may be missing. This opening could optionally be optically closed with the use of a beamsplitter to admit light from another location.

In this regard, certain embodiments of the detailed description include full-eye illumination ocular surface interferometry (OSI) devices, systems, and methods for imaging an ocular tear film and/or measuring a tear film layer thickness (TFLT) in a patient's ocular tear film. OSI devices, systems, and methods can be used to provide full eye illumination to measure the thickness of the lipid layer component (LLT) and/or the aqueous layer component (ALT) of the ocular tear film. "TFLT" as used herein includes LLT, ALT, or both LLT and ALT. "Measuring TFLT" as used herein includes measuring LLT, ALT, or both LLT and ALT. Imaging the ocular tear film and measuring TFLT can be used in the diagnosis of a patient's tear film, including but not limited to lipid layer and aqueous layer deficiencies. These characteristics may be the cause or contributing factor to a patient experiencing dry eye syndrome (DES).

In other embodiments of the detailed description, full-eye illumination ocular topography devices, systems and methods for deducing corneal shape by capturing a full-eye image of a target reflecting from the surface of the cornea are provided. The image of the target contains topography information that is reviewable by a clinician to diagnose the health of the patient's eye by detecting corneal aberrations and/or abnormalities in corneal shape. In cases where the ocular property is corneal shape and a corneal topography analysis is to be conducted by a clinician, the subtraction of the at least one second image from the at least one first image produces a Placido pattern. A typical Placido pattern comprises concentric circles and radials.

Moreover, certain other embodiments of the detailed description also include a combination of full-eye illumination OSI and ocular topography devices, systems and methods to provide imaging that can be used to yield a combined diagnosis of the patient's tear film and corneal shape. Because embodiments provided herein include providing an OSI device for measuring TFLT that is configured to illuminate the eye with circular shaped light patterns, the same images resulting from illumination of the eye in circular lighting patterns also provide circular topography information about the cornea that can be observed for corneal topography analysis. An exemplary benefit of a combined diagnosis would be using corneal topography imaging for fitting contact lenses, while performing a precorneal tear film analysis and TFLT measurements before, during, and/or after the fitting of the contact lenses to ensure that the contact lenses do not interfere with proper tear film production and distribution.

In this regard in one tear film imaging embodiment, an imaging apparatus is provided that includes a multi-wavelength light source that is configured to emit light to an eye. A control system is provided in the imaging apparatus, wherein the control system is configured to spatially modulate light from the multi-wavelength light source to project a first circular pattern onto the eye, such that at least one first portion of the eye receives emitted light from the multi-wavelength light source and at least one second portion of the eye does not receive the emitted light from the multi-wavelength light source. Providing the circular or elliptical illumination pattern provides a greater eye illumination, which is referred to herein as "full eye illumination" and "full eye imaging." An imaging device of the imaging apparatus receives at least one first image containing at least one first signal associated with an ocular property of the eye that comprises the emitted light reflected from the at least one first portion of the eye. Light from the multi-wavelength light source is then modulated to project a second circular pattern onto the eye, such that the at least one first portion of the eye does not receive emitted light from the multi-wavelength light source and the at least one second portion on the eye receives the emitted light from the multi-wavelength light source. The imaging device then receives at least one second image containing at least one second signal associated with the ocular property of the eye comprising the emitted light reflected from the at least one second portion of the eye. The control system then subtracts the at least one second image from the at least one first image to generate at least one resulting image containing a resultant signal that represents the ocular property of the eye. The image of the eye can be displayed to a technician or other user. The image can also be processed and analyzed to measure a TFLT in the area or region of interest of the ocular tear film.

As provided above, the subtraction of the at least one second image from the at least one first image provides at least one resulting image that is more useful in determining tear film thickness. In this regard, the first image is processed to subtract or substantially subtract out the background signal(s) superimposed upon an interference signal to reduce error before being analyzed to measure TFLT, wherein the interference signal results from optical wave interference (also referred to as light wave interference) of specularly reflected light. This is referred to as "background subtraction" in the present disclosure. The separate background signal(s) includes returned captured light that is not specularly reflected from the tear film and thus does not contain optical wave interference information (also referred to as "interference information"). For example, the background signal(s) may include stray, ambient light entering into the imaging device, scattered light from the patient's face and eye structures both outside and within the tear film as a result of ambient light and diffuse illumination by the light source, and eye structure beneath the tear film, and particularly contribution from the extended area of the source itself. The background signal(s) adds a bias (i.e., offset) error to the interference signal(s) thereby reducing interference signal strength and contrast. This error can adversely influence measurement of TFLT. Further, if the background signal(s) has a color hue different from the light of the light source, a color shift can also occur to the captured optical wave interference (also referred to as "interference") of specularly reflected light, thus introducing further error.

In one embodiment of tear film imaging, an optically "tiled" or "tiling" circular pattern illumination of the tear film is provided to provide improved background subtraction. Tiling involves spatially controlling a light source to form specific lighting patterns on the light source when illuminating a portion(s) in an area or region of interest on the tear film in a first mode to obtain specularly reflected light and background signal(s). In embodiments disclosed herein, the background signal(s) in the second image additionally includes scattered light as a result of diffuse illumination by the light source providing circular pattern illumination. Because background signal(s) due to scattered light as a result of diffuse illumination by the light source is also present in the first image, capturing a second image that includes diffuse illumination by the light source can further reduce bias (i.e., offset) error and increase interference signal strength and contrast over embodiments that do not control the light source to illuminate the tear film when the second image is captured.

In this regard, the light source is controlled in a first mode to provide a circular lighting pattern to produce specularly reflected light from a first portion(s) in the area or region of interest of the tear film while obliquely illuminating an adjacent, second portion(s) of the area or region of interest of the tear film in a circular lighting pattern. The imaging device captures a first image representing the interference of the specularly reflected light with additive background signal(s) from the first portion(s) of the area or region of interest, and background signal(s) from a second portion(s) of the area or region of interest. The background signal(s) from the second portion(s) includes scattered light as a result of diffuse reflection of the illumination by the light source, and ambient light. The light source is then alternately controlled in a second mode to reverse the lighting pattern of the first mode to capture specularly reflected light from the second portion(s) in the area or region of interest of the tear film while obliquely illuminating the first portion(s) in the area or region of interest of the tear film. The imaging device captures a second image representing the interference of the specularly reflected light and with additive background signal(s) from the second portion(s) in the area or region of interest on the tear film, and background signal(s) from the first portion(s) in the area or region of interest on the tear film. The background signal(s) from the first portion(s) includes scattered light as a result of diffuse reflection of the illumination by the light source. The first and second images are combined to subtract or substantially subtract background offset from the interference signals to produce the resulting image. Again, the resulting image can be displayed on a visual display to be analyzed by a technician and processed and analyzed to measure a TFLT.

After the interference of the specularly reflected light is captured and a resulting image containing the interference signal is produced from any method or device disclosed in this disclosure, the resulting image can also be pre-processed before being processed and analyzed to measure TFLT. Pre-processing can involve performing a variety of methods to improve the quality of the resulting signal, including but not limited to detecting and removing eye blinks or other signals in the captured images that hinder or are not related to the tear film. After pre-processing, the interference signal or representations thereof can be processed to be compared against a tear film layer interference model to measure TFLT. The interference signal can be processed and converted by the imaging device into digital red-green-blue (RGB) component values which can be compared to RGB component values in a tear film interference model to measure TFLT on an image pixel-by-pixel basis. The tear film interference model is based on modeling the lipid layer of the tear film in various thicknesses and mathematically or empirically observing and recording resulting interference interactions of specularly reflected light from the tear film model when illuminated by the light source and detected by a camera (imaging device).

Certain embodiments of the detailed description also include full-eye ocular topography devices, systems and methods for deducing corneal shape by capturing an image of a target reflecting from the surface of the cornea. The eye is illuminated with a circular or elliptical shaped illumination pattern, because of the cornea being circular shaped, to perform a topography of the cornea. The image of the target contains topography information that is reviewable by a clinician to diagnose the health of the patient's eye by detecting corneal aberrations and/or abnormalities in corneal shape. In cases where the ocular property is corneal shape and a corneal topography analysis is to be conducted by a clinician, to improve the imaging of the eye for corneal topography, at least one second image capture from full-eye illumination is subtracted from the at least one first image produces a Placido pattern. A typical Placido pattern comprises concentric circles and radials. Any of the aforementioned background subtraction techniques, including tiling, may be employed.

Moreover, certain other embodiments of the detailed description also include a combination of full-eye illumination OSI and ocular topography devices, systems and methods to provide imaging that can be used to yield a combined diagnosis of the patient's tear film and corneal shape. Because embodiments provided herein include providing an OSI device for measuring TFLT that is configured to illuminate the eye with circular shaped light patterns, the same images resulting from illumination of the eye in circular lighting patterns also provide circular topography information about the cornea that can be observed for corneal topography analysis. An exemplary benefit of a combined diagnosis would be using corneal topography imaging for fitting contact lenses, while performing a precorneal tear film analysis and TFLT measurements before, during, and/or after the fitting of the contact lenses to ensure that the contact lenses do not interfere with proper tear film production and distribution.

In this regard, certain embodiments disclosed herein include a light modulator system that is communicatively coupled to the control system to spatially modulate light from the multi-wavelength light source to alternately project the first circular pattern and the second circular pattern onto the eye to illuminate the ocular property thereby generating the first signal and the second signal of the ocular property. Moreover, in one embodiment, the light modulator system includes a disk disposed between the imaging device and eye for sequentially projecting the first circular pattern and the second circular pattern onto the eye when the disk is illuminated, and wherein the disk includes a central aperture for the imaging device to receive light reflected from the eye. In one embodiment, the disk is rotatable and is patterned with a plurality of concentric circles having alternating opaque and translucent sections with edges that form radials. The disk is rotated under the control of the control system to generate the first circular pattern and the second circular pattern. In yet another embodiment, the disk is made up of a substrate having pixels that are controllable by a controller. Instead of rotating the disk to generate the first and second circular patterns, the pixels are controllable to transition between dark and light in response to signals transmitted from the controller. It is to be understood that the controllable pixels can do more than invert the light and dark regions. A pattern of pixels can scan and/or use various pattern types to provide many more points for higher resolutions and more quantifiable topography. Ultimately, either embodiment produces images that are usable for determining ocular properties of the eye. As discussed above, one such ocular property is ocular tear film thickness.

Beyond ocular tear film measurement, embodiments of the present disclosure are also configured to generate a Placido pattern for determining another ocular property, which may be corneal shape. In this regard, embodiments disclosed herein yield a benefit of being usable for analyzing an ocular topography. For example, subtracting the at least one second image from the at least one first image generates at least one resulting image that is a Placido pattern that comprises concentric circles and radials. Irregularities such as warped radials and skewed circles captured in the Placido pattern of a resulting image(s) indicate abnormalities of the corneal surface. In order to assist a diagnosis of such abnormalities, the Placido pattern within the resulting image is viewable on a visual display. Better yet, embodiments of the present disclosure are usable to correlate aberrations of the corneal tear film with abnormalities of the corneal surface.

In this regard, the first ocular property may be a thickness of an ocular tear film and the second ocular property may be corneal shape. In operation, the embodiments of the present disclosure illuminate the ocular tear film and project a first circular pattern onto the tear film to produce specularly reflected light from the first portion(s) of the ocular tear film while non-specular illuminating second adjacent portions of the ocular tear film. A first image(s) of the eye that includes the first circular pattern and specular reflections from the tear film is captured by the imaging device. Next, the control system inverts the first circular pattern to provide a second circular pattern. A second image(s) of the eye that includes the second circular pattern with specular reflections from the tear film is captured by the imaging device. The first and second images are combined to provide a third circular pattern containing tear film thickness information and corneal topography information. It is to be understood that the first and second images can be combined to generate various other patterns useful for eye health assessment and analysis. In at least one embodiment, the third circular pattern is a Placido pattern having concentric rings and radials. In this case, the Placido pattern includes tear film thickness information between the concentric circles and radials, while the concentric circles and radials of the Placido disk contain the corneal topography information. A benefit of this embodiment providing combined functions of tear film thickness measurement and ocular topography display by using of the circular patterns to capture reflected light from the eye in concentric circles and/or radials. As such, the present embodiments provide substantial purchase cost and operational cost savings over tradition ocular instruments by integrating tear film thickness measurement and ocular topography display functions into one OSI device. It is to be understood that while circular patterns may be preferable, a rectangular grid or rectangular checkerboard pattern is also usable for full eye analysis of tear film and topography. A rectangular pattern might need to be somewhat larger than a circular pattern; however, with computerized analysis profilometry can still be performed.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawing figures incorporated in and forming a part of this specification illustrate several aspects of the disclosure, and together with the description serve to explain the principles of the disclosure. Note that drawing figures that include photographs of real eyes also include prophetic image overlays of patterns of diffuse and specularly reflected light. In particular, FIGS. 7A, 7B, 7C, 20, 21A, 21B, 22, 23, 27A, 27B, 27C, 35, 42, 43, 44, and 45 include prophetic image overlays.

FIGS. 4A and 4B are illustrations of an exemplary light source and imaging device to facilitate discussion of illumination of the tear film and capture of interference interactions of specularly reflected light from the tear film and for providing ocular topography images;

DETAILED DESCRIPTION

Figure 1:
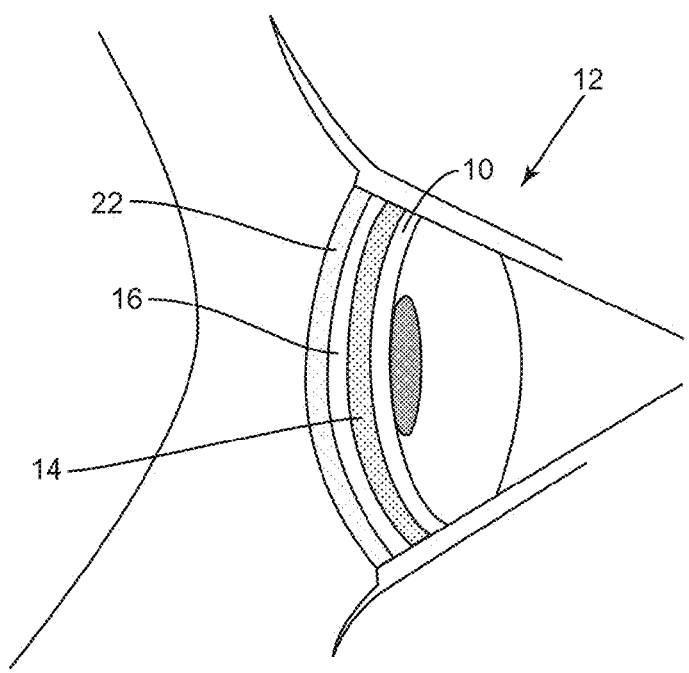
FIG. 1 is a side view of an exemplary eye showing the three layers of the tear film in exaggerated form.
Figure 2:
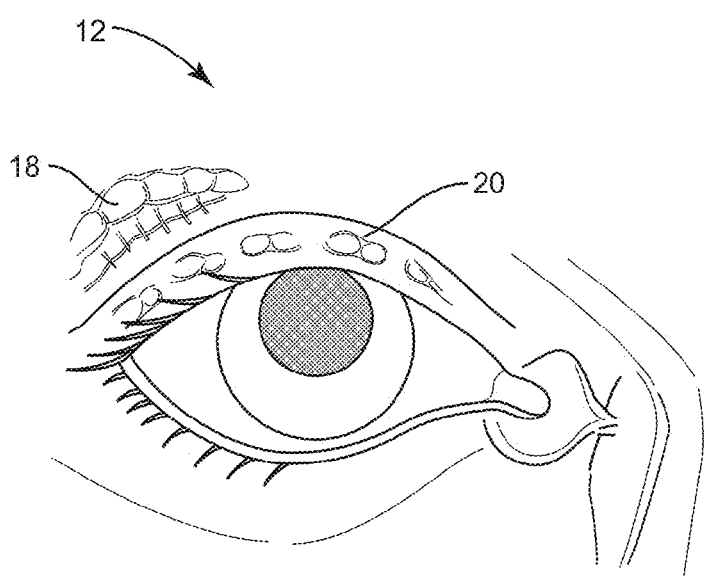
FIG. 2 is a front view of an exemplary eye showing the lacrimal and accessory tear glands that produce aqueous in the eye.
Figure 3:
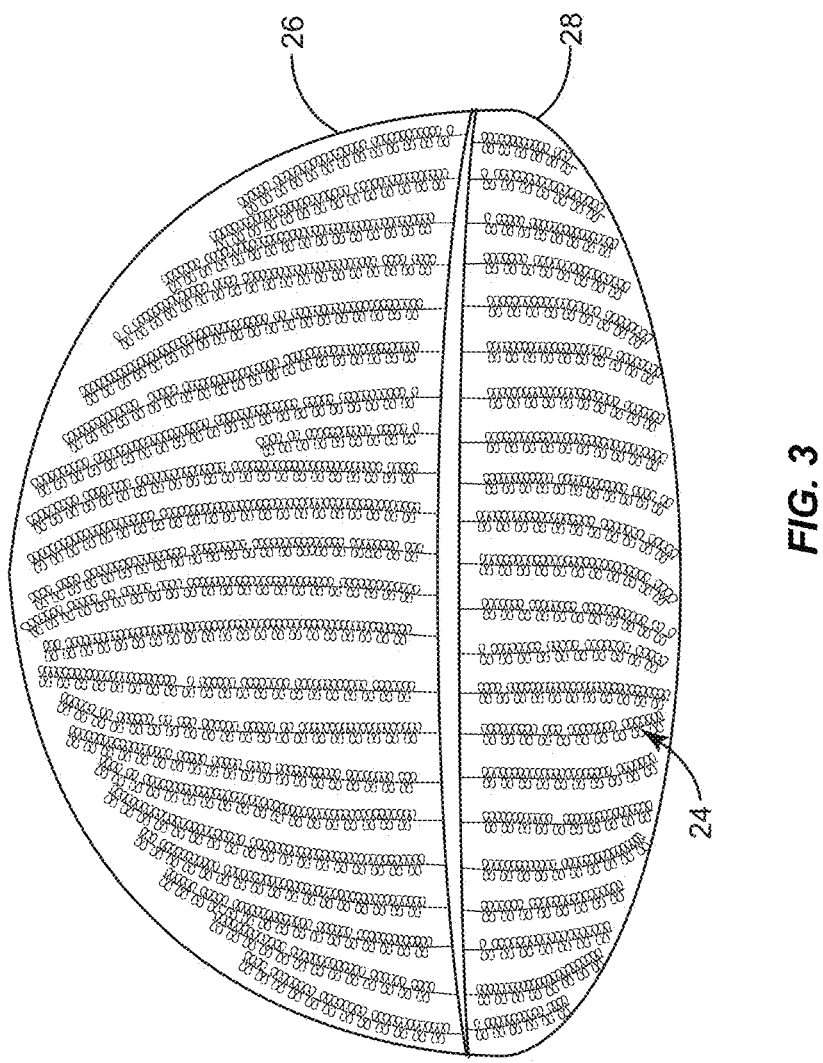
FIG. 3 illustrates exemplary upper and lower eyelids showing the meibomian glands contained therein.

The embodiments set forth below represent the necessary information to enable those skilled in the art to practice the disclosure and illustrate the best mode of practicing the disclosure. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Ocular surface imaging of ocular tear films and ocular topography are provided herein. Embodiments of the detailed description include ocular surface interferometry (OSI) devices, systems, and methods for imaging an ocular tear film and/or measuring a tear film layer thickness (TFLT) in a patient's ocular tear film. The OSI devices, systems, and methods can be used to measure the thickness of the lipid layer thickness (LLT) component and/or the aqueous layer thickness (ALT) component of the ocular tear film. "TFLT" as used herein includes LLT, ALT, or both LLT and ALT. "Measuring TFLT" as used herein includes measuring LLT, ALT, or both LLT and ALT. Imaging the ocular tear film and measuring TFLT can be used in the diagnosis of a patient's tear film, including but not limited to lipid layer and aqueous layer deficiencies. These characteristics may be the cause or contributing factor to a patient experiencing dry eye syndrome (DES).

In this regard, embodiments disclosed herein provide a full eye imaging apparatus for determining ocular properties of the eye, including TFLT and ocular surface properties. Full-eye imaging means illuminating the eye with a circular lighting pattern to be compatible with the circular shape of the cornea. A further advantage of the disclosed simultaneous dual properties measurement (TFLT and topography) is that corneal topographical measurements can be corrected for variations in tear film thickness, and in particular ALT.

Certain embodiments of the detailed description also include ocular topography devices, systems and methods for deducing corneal shape by capturing an image of a target reflecting from the surface of the cornea. The image of the target contains topography information that is reviewable by a clinician to diagnose the health of the patient's eye by detecting corneal aberrations and/or abnormalities in corneal shape. In cases where the ocular property is corneal shape and a corneal topography analysis is to be conducted by a clinician, the subtraction of the at least one second image from the at least one first image produces a Placido pattern. A typical Placido pattern comprises concentric circles and radials.

Moreover, certain other embodiments of the detailed description also include a combination of OSI and ocular topography devices, systems and methods to provide imaging that can be used to yield a combined diagnosis of the patient's tear film and corneal shape. Because embodiments provided herein include providing an OSI device for measuring TFLT that is configured to illuminate the eye with circular shaped light patterns, the same images resulting from illumination of the eye in circular lighting patterns also provide circular topography information about the cornea that can be observed for corneal topography analysis. An exemplary benefit of a combined diagnosis would be using corneal topography imaging for fitting contact lenses, while performing a precorneal tear film analysis and TFLT measurements before, during, and/or after the fitting of the contact lenses to ensure that the contact lenses do not interfere with proper tear film production and distribution.

Exemplary OSI Device with Motorised Placido Disk

Figure 4B:
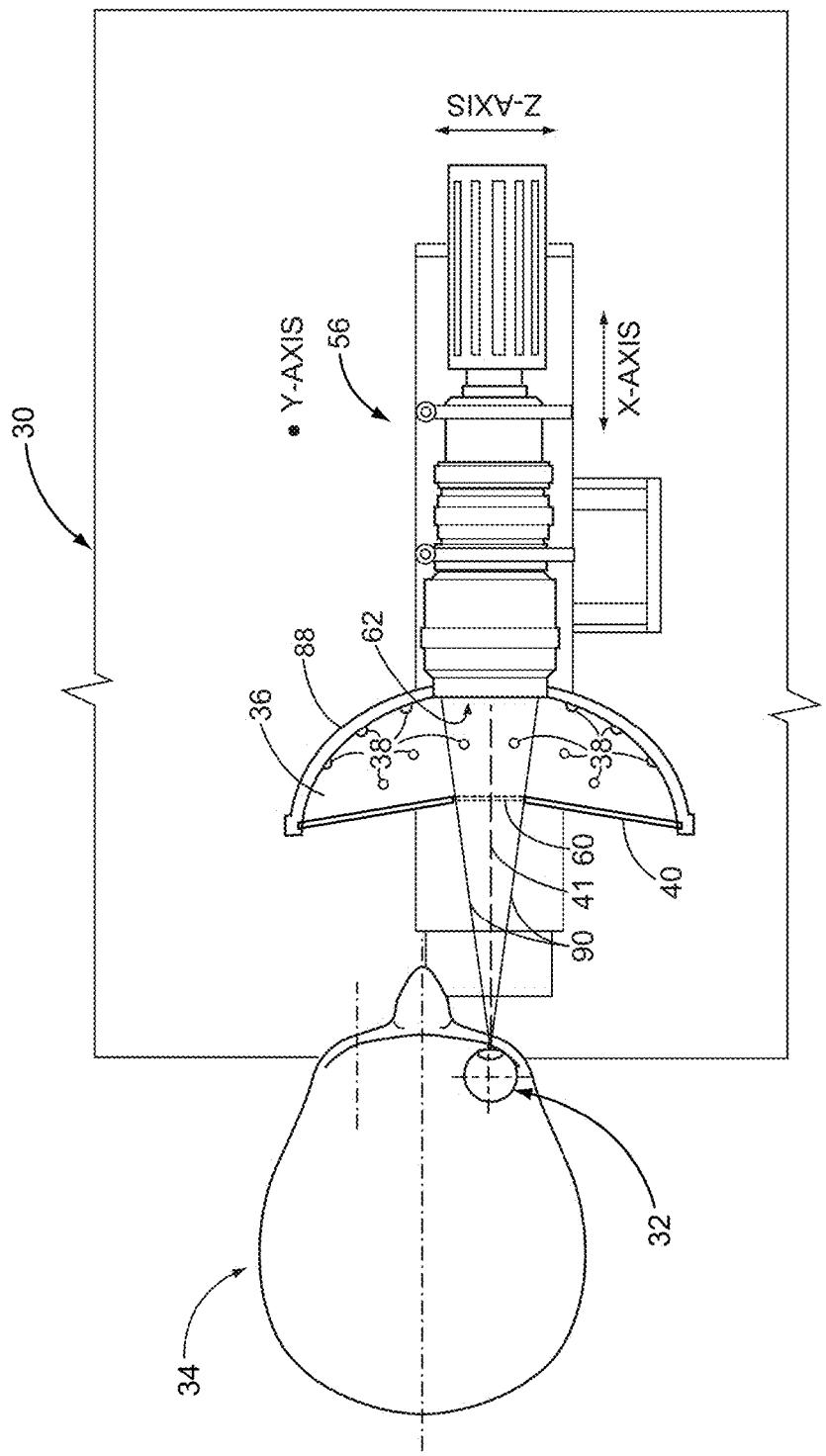

In this regard, FIGS. 4A-4B illustrate a general embodiment of an ocular surface interferometry (OSI) device 30 for providing ocular surface imaging of ocular tear film and ocular topography. Other embodiments will be described later in this application. In general, the OSI device 30 is configured to illuminate a patient's ocular tear film, capture images of interference interactions of specularly reflected light from the ocular tear film, and process and analyze the interference interactions to measure TFLT. As shown in FIG. 4A, the exemplary OSI device 30 positioned in front of one of the patient's eye 32 is shown from a side view. A top view of the patient 34 in front of the OSI device 30 is illustrated in FIG. 4B. The ocular tear film of a patient's eyes 32 is illuminated with a light source 36 (also referred to herein as "illuminator 36") and comprises a large area light source having a spectrum in the visible region adequate for TLFT measurement and correlation to dry eye. The illuminator 36 can be a white or multi-wavelength light source and in this exemplary embodiment is made up of an array of light emitting diodes (LEDs) 38. An optional diffuser can be included to improve the uniformity of the LEDs 38.

In this embodiment, the illuminator 36 is a Lambertian emitter and is adapted to be positioned in front of the patient's eye 32. As employed herein, the terms "Lambertian surface" and "Lambertian emitter" are defined to be a light emitter having equal or substantially equal (also referred to as "uniform" or substantially uniform) intensity in all pertinent directions. This allows the imaging of the reflection of a uniformly or substantially uniformly bright tear film region for TFLT, as discussed in more detail in this disclosure. The illuminator 36 comprises a large surface area emitter, arranged such that rays emitted from the emitter are specularly reflected from the ocular tear film and undergo constructive and destructive interference in tear film layers therein. An image of the patient's 34 lipid layer is the backdrop over which the interference image is seen and it should be as spatially uniform as possible. Although it is convenient to have the illuminator 36 emit light in a substantially spatially uniform manner, it should be understood that a calibration and correction for less spatially uniform light emissions can be accomplished via processing using a processor of the OSI device 30.

A Placido disk 40 is disposed between the illuminator 36 and the patient 34. A cut-away along a line A-A' depicts the Placido disk 40 in this exemplary embodiment as having a circular pattern 42 including concentric circles 44 with alternating opaque tiles 46 and translucent tiles 48 that have edges that form radials 50. The exemplary OSI device 30 includes an electric motor 52 coupled to a drive mechanism 54 for rotating the Placido disk 40 around an optical axis 41. In this particular embodiment, the Placido disk 40 is rotatably coupled to the illuminator 36 which in turn is attached to an imaging device 56 included in the OSI device 30. The Placido disk 40 may be a flexible, acrylic plastic sheet that is patterned with a circular pattern having concentric circles, radials, and alternating opaque tiles and translucent tiles. The Placido disk 40 also includes a centrally located aperture 60 through which the imaging device 56 receives light.

In operation, a controller 58 synchronizes the rotation of the Placido disk 40 with the capturing of images via the imaging device 56. In particular, the imaging device 56 is employed to capture interference interactions of specularly reflected light from the patient's 34 ocular tear film when illuminated by the illuminator 36. A desired portion of the specularly reflected light passes through the aperture 60 in the Placido disk 40 to impinge upon an imaging lens 62 of the imaging device 56. A stand 64 carries the imaging device 56 and the electric motor 52. The stand 64 allows for height adjustment of the imaging device 56 along a Y-AXIS. The stand 64 is also movable along an X-AXIS for positioning the imaging device 56 relative to the patient 34. The imaging device 56 may be a still or video camera, or other device that captures images and produces an output signal representing information in captured images. The output signal may be a digital representation of the captured images.

Figure 5:
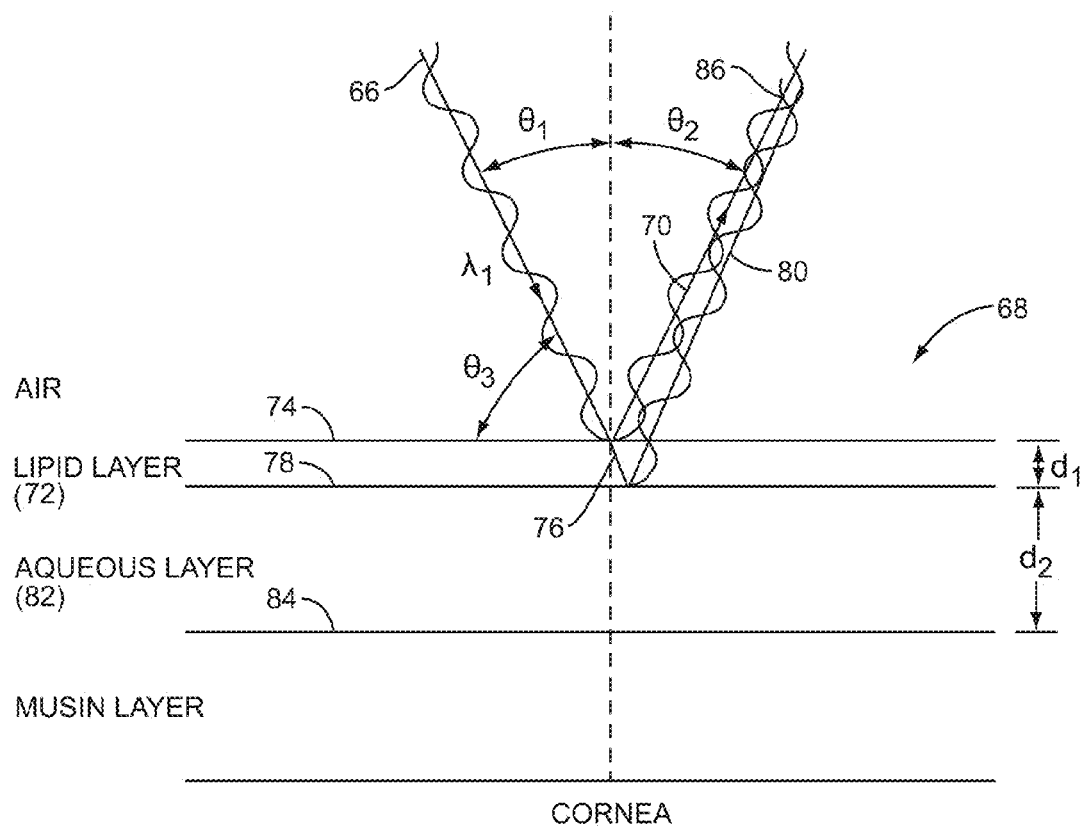
FIG. 5 illustrates (in a microscopic section view) exemplary tear film layers to illustrate how light rays can specularly reflect from various tear film layer transitions to produce light wave interference.

The geometry of the illuminator 36 can be understood by starting from the imaging lens 62 of the imaging device 56 and proceeding forward to the patient's eye 32 and then to the illuminator 36. The fundamental equation for tracing ray lines is Snell's law, which provides:

$$n1 \sin \Theta_1 = n2 \sin \Theta_2,$$

where "n1" and "n2" are the indexes of refraction of two mediums containing the ray, and $\Theta_1$ and $\Theta_2$ are the angles of the ray relative to the normal from the transition surface. As illustrated in FIG. 5, light rays 66 are directed by the illuminator 36 to an ocular tear film 68. In the case of specularly reflected light 70 that does not enter a lipid layer 72 and instead reflects from an anterior surface 74 of the lipid layer 72, Snell's law reduces down to $\Theta_1 = \Theta_2$, since the index of refraction does not change (i.e., air in both instances). Under these conditions, Snell's law reduces to the classical law of reflection such that the angle of incidence is equal and opposite to the angle of reflectance.

Some of the light rays 76 pass through the anterior surface 74 of the lipid layer 72 and enter into the lipid layer 72, as illustrated in FIG. 5. As a result, the angle of these light rays 76 (i.e., $\Theta_3$) normal to the anterior surface 74 of the lipid layer 72 will be different than the angle of the light rays 66 ($\Theta_1$) according to Snell's law. This is because the index of refraction of the lipid layer 72 is different than the index of refraction of air. Some of the light rays 76 passing through the lipid layer 72 will specularly reflect from the lipid layer-to-aqueous layer transition 78 thereby producing specularly reflected light rays 80. The specularly reflected light rays 70, 80 undergo constructive and destructive interference anterior of the lipid layer 72. The modulations of the interference of the specularly reflected light rays 70, 80 superimposed on the anterior surface 74 of the lipid layer 72 are collected by the imaging device 56 (FIGS. 4A and 4B) when focused on the anterior surface 74 of the lipid layer 72. Focusing the imaging device 56 on the anterior surface 74 of the lipid layer 72 allows capturing of the modulated interference information at the plane of the anterior surface 74. In this manner, the captured interference information and the resulting calculated TFLT from the interference information is spatially registered to a particular area of the tear film 68 since the calculated TFLT can be associated with such particular area, if desired.

The thickness of the lipid layer 72 ('$d_1$') is a function of the interference interactions between specularly reflected light rays 70, 80. The thickness of the lipid layer 72 ('$d_1$') is on the scale of the temporal (or longitudinal) coherence of the illuminator 36. Therefore, thin lipid layer films on the scale of one wavelength of visible light emitted by the illuminator 36 offer detectable colors from the interference of specularly reflected light when viewed by a camera or human eye. The colors may be detectable as a result of calculations performed on the interference signal and represented as digital values including, but not limited to, a red-green-blue (RGB) value in the RGB color space. Quantification of the interference of the specularly reflected light can be used to measure LLT. The thicknesses of an aqueous layer 82 ('$d_2$') can also be determined using the same principle. Some of the light rays 76 (not shown) passing through the lipid layer 72 can also pass through the lipid layer-to-aqueous layer transition 78 and enter into the aqueous layer 82 specularly reflecting from the aqueous-to-mucin/cornea layer transition 84. These specular reflections also undergo interference with the specularly reflected light rays 70, 80. The magnitude of the reflections from each interface depends on the refractive indices of the materials as well as the angle of incidence, according to Fresnel's equations, and so the depth of the modulation of the interference interactions is dependent on these parameters, thus so is the resulting color.

Turning back to FIGS. 4A and 4B, the illuminator 36 in this embodiment is a broad spectrum light source covering the visible region between about 400 nm to about 700 nm. The illuminator 36 contains an arced or curved housing 88 (see FIG. 4B) into which the LEDS 38 are mounted, subtending an arc of approximately 130 degrees from the optical axis 41 of the patient's eye 32 (see FIG. 4B). A curved surface may present better uniformity and be more efficient, as the geometry yields a smaller device to generating a given intensity of light. The total power radiated from the illuminator 36 should be kept to a minimum to prevent accelerated tear evaporation. Light entering the pupil can cause reflex tearing, squinting, and other visual discomforts, all of which affect TFLT measurement accuracy.

In order to prevent alteration of the proprioceptive senses and reduce heating of the tear film 68, incident power and intensity on the patient's eye 32 may be minimized and thus, the step of collecting and focusing the specularly reflected light may be carried out by the imaging device 56. The imaging device 56 may be a video camera, slit lamp microscope, or other observation apparatus mounted on the stand 64, as illustrated in FIGS. 4A and 4B. Detailed visualization of the image patterns of the tear film 68 involves collecting the specularly reflected light 90 (see FIG. 4B) and focusing the specularly reflected light 90 at the lipid layer 72 such that the interference interactions of the specularly reflected light from the ocular tear film are observable.

In the embodiment shown in FIGS. 4A-4B, a second image is captured when the tear film is obliquely illuminated by the illuminator 36 using illumination that possesses the same or nearly the same average geometry and illuminance level as used to produce specularly reflected light from a tear film. In this manner, the background signal captured in the second image contains the equivalent background signal present in the first image including scattered light from the tear film and patient's eye as a result of diffuse illumination by the illuminator 36. The second image also includes a representative signal of eye structure beneath the tear film because of the equivalent lighting when the illuminator 36 is activated when capturing the second image. In the embodiment of FIGS. 4A and 4B, the Placido disk 40 provides a "tiled" or "tiling" illumination of the tear film. Tiling allows a light source to illuminate a sub-area(s) of interest on the tear film to obtain specularly reflected light while at the same time non-specularly illuminating adjacent sub-area(s) of interest of the tear film to obtain scattered light as a result of diffuse illumination by the illuminator 36. In this manner, the subtracted background signal includes scattered light as a result of diffuse illumination by the illuminator 36 to allow further reduction of offset bias (i.e., offset) error and to thereby increase interference signal purity and contrast.

Figure 6:
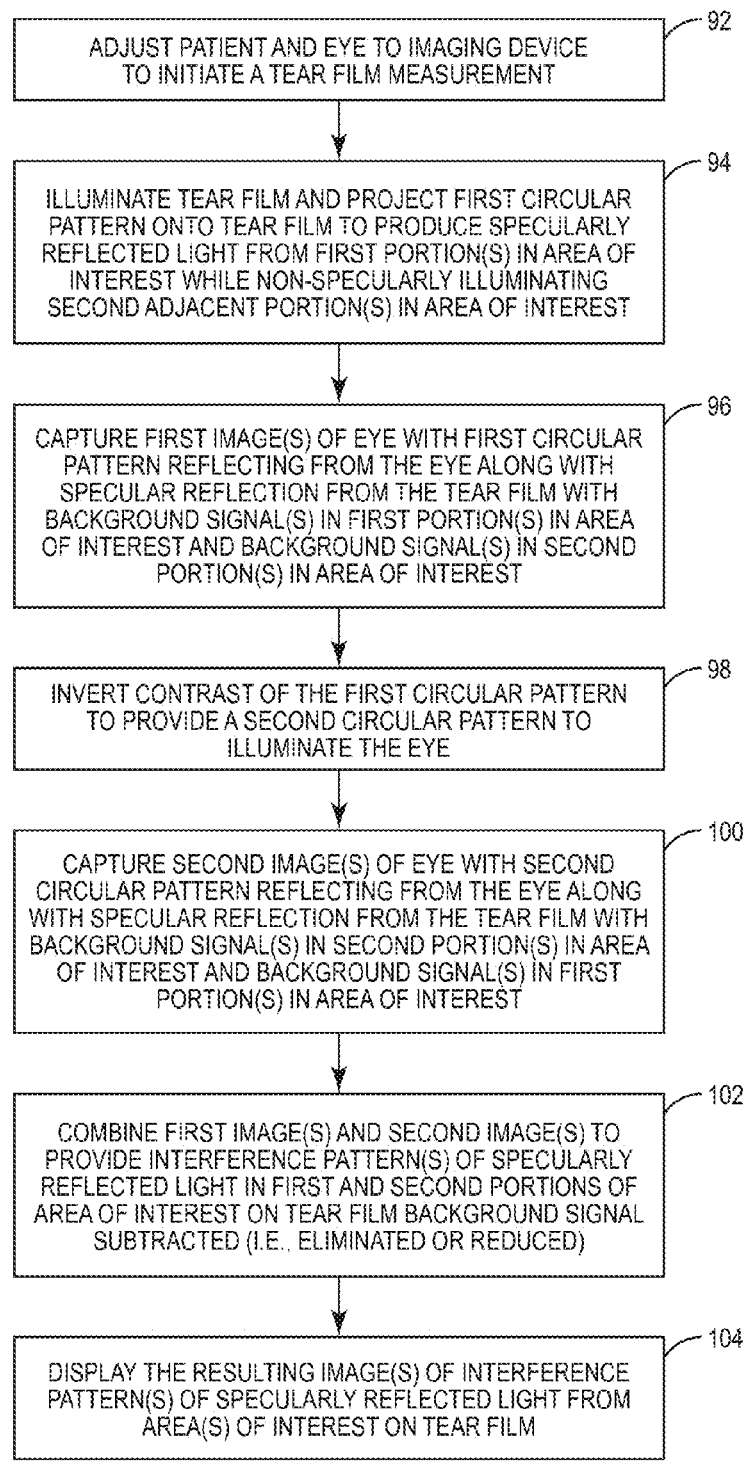
FIG. 6 is a flowchart of an exemplary process for obtaining one or more interference signals from images of a tear film representing specularly reflected light from the tear film with background signal subtracted or substantially subtracted.

In this regard, as illustrated in FIG. 6, the process starts by adjusting the patient 34 with regard to the illuminator 36 and the imaging device 56 (block 92). The illuminator 36 is controlled to illuminate the patient's 34 tear film. The imaging device 56 is located appropriately and is controlled to be focused on the lipid layer such that the interference interactions of specularly reflected light from the tear film are observable when the tear film is illuminated. Thereafter, light emitted from the illuminator 36 is modulated via the Placido disk 40 in a first "tiling" mode in which a first circular pattern 42A (FIG. 8A) is projected onto the patient's 34 tear film to produce specularly reflected light from a first area(s) of interest of the tear film while non-specularly illuminating an adjacent, second area(s) of interest of the tear film (block 94). Specifically, the circular pattern 42 of the Placido disk 40 is projected onto the patient's eye 32.

Figure 7A:
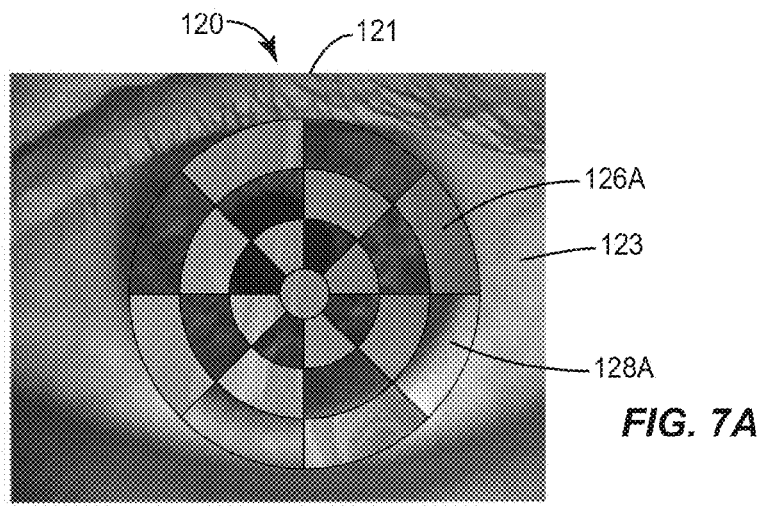
FIG. 7A illustrates a first image focused on a lipid layer of a tear film and capturing interference interactions of specularly reflected light from an area or region of interest of the tear film.

An example of a first image 120 captured of a patient's eye 121 and tear film 123 by the imaging device 56 when the illuminator 36 produces the circular pattern 42 in the first mode is illustrated by example in FIG. 7A. In this example, the illuminator 36 and Placido disk 40 are controlled to provide a first tiled illumination pattern on the tear film 123. While illumination of the tear film 123 is in the first mode, the imaging device 56 captures the first image 120 of the patient's eye 121 and the tear film 123 (block 96). As illustrated in FIG. 7A, the first image 120 of the patient's eye 121 has been illuminated so that specularly reflected light is produced in first portions 126A of the tear film 123. The interference signal(s) from the first portions 126A include interference from specularly reflected light along with additive background signal, which includes scattered light signal as a result of diffuse illumination from the illuminator 36. Again, the illuminator 36 and the imaging device 56 may be controlled to illuminate the tear film 123 that does not include the pupil of the eye 121 so as to reduce reflex tearing. The illuminator 36 may be flashed in block 94 to produce specularly reflected light from the first portions 126A, whereby the imaging device 56 is synchronized with the frequency of the projection of the circular pattern 42 in block 96 to capture the first image 120 of the patient's eye 121 and the tear film 123.

Also during the first mode, the illuminator 36 obliquely illuminates adjacent second portions 128A to the first portions 126A on the eye 121, as shown in the first image 120 in FIG. 7A. The second portions 128A include comparable background offset present in the first portion(s) 126A, which includes scattered light signal as a result of diffuse illumination from the illuminator 36 since the illuminator 36 is turned on when the first image 120 is captured by the imaging device 56. Further, the eye 121 structures beneath the tear film 123 are captured in the second portions 128A due to the diffuse illumination by the illuminator 36. Moreover, in this embodiment, the area of the tear film 123 is broken into two portions at the same time: first portions 126A producing specularly reflected light combined with background signal, and second portions 128A diffusedly illuminated by the illuminator 36 and containing background signal, which includes scattered light from the illuminator 36. The imaging device 56 produces a first output signal that contains a representation of the first portions 126A and the second portions 128A.

Figure 8A:
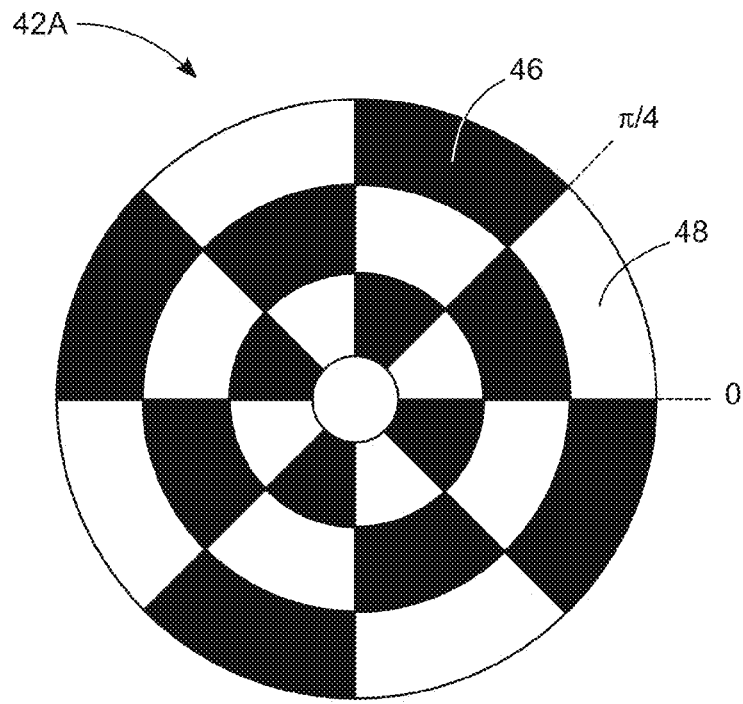
FIG. 8A is an exemplary first circular pattern having concentric circles with alternating opaque tiles and translucent tiles that have edges that form radials.

Next, the illuminator 36 and the Placido disk 40 are controlled in a second mode to invert the first circular pattern 42A (FIG. 8A) from the first mode when illuminating the tear film 123 (block 98, FIG. 6). An exemplary method usable to invert the first circular pattern can be better understood by turning to FIGS. 8A and 8B. In FIG. 8A, the first circular pattern 42A is in a first mode in which an outer one of the translucent tiles 48 is located between 0 radians and $\pi/4$ radians. The second mode shown in FIG. 8B occurs after the first circular pattern 42A is rotated by $\pi/4$ radians in either direction. In the second mode, an outer one of the opaque tiles 46 is now located between 0 radians and $\pi/4$ radians. As such, all of the opaque tiles 46 and all of the translucent tiles 48 have been effectively inverted (i.e. swapped) between the first mode and the second mode. It is to be understood that an angle of rotation (N) necessary for Placido disk 40 to invert the opaque tiles 46 and the translucent tiles 48 is a function of the number of radials (R) that separate the opaque tiles 46 and the translucent tiles 48. The angle of rotation N is equal to $2\pi/R$.

Figure 7B:
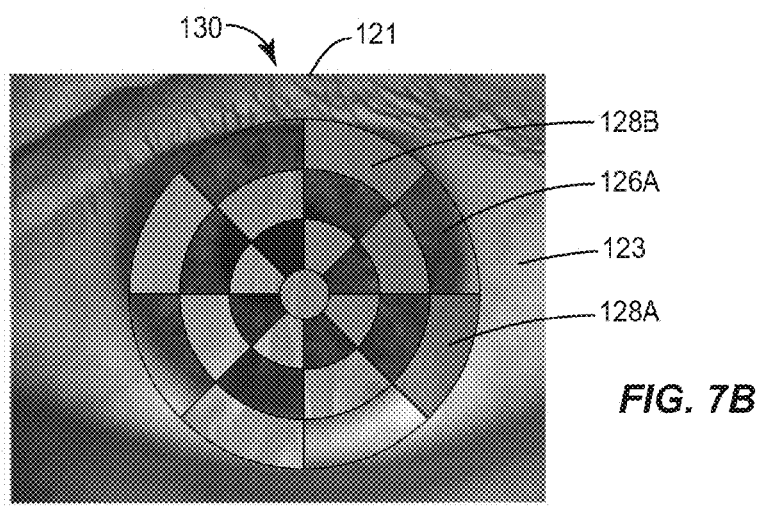
FIG. 7B illustrates a second image focused on the lipid layer of the tear film in FIG. 7A and capturing background signal when not illuminated by the light source.

Returning to FIG. 6, a second image 130 of the tear film 123 in the second mode, as illustrated by example in FIG. 7B (block 100, FIG. 6). As shown in the second image 130 in FIG. 7B, the second portions 128A in the first image 120 of FIG. 7A are now second portions 128B in the second image 130 in FIG. 7B containing specularly reflected light from the tear film 123 with additive background signal. The first portions 126A in the first image 120 of FIG. 7A are now first portions 126B in the second image 130 in FIG. 7B containing background signal without specularly reflected light. Again, the background signal in the first portions 126B includes scattered light signal as a result of diffuse illumination by the illuminator 36. The imaging device 56 produces a second output signal of the second image 130 in FIG. 7B. The illuminator 36 may also be flashed in block 98 to produce specularly reflected light from the second portions 128B, whereby the imaging device 56 is synchronized with the frequency of the projection of the second circular pattern in block 98 to capture the second image 130 of the patient's eye 32 and the tear film 123.

Figure 7C:
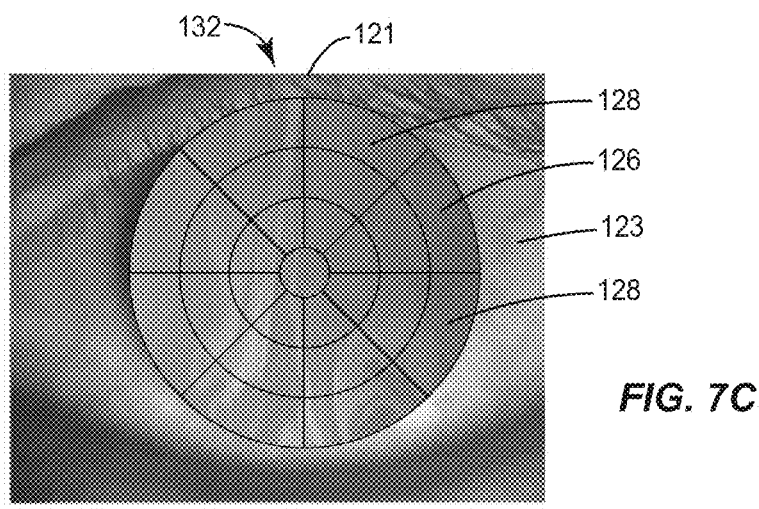
FIG. 7C illustrates an image of the tear film when background signal captured in the second image of FIG. 7B is subtracted from the first image of FIG. 7A.
Figure 8B:
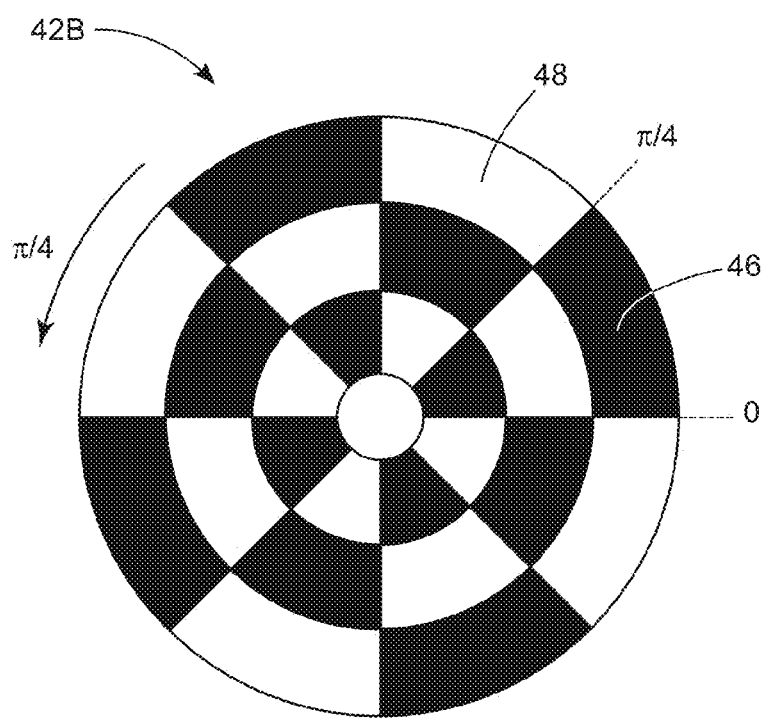
FIG. 8B is an exemplary second circular pattern that is the inverse contrast of the first circular pattern.

The first and second output signals can then be combined to produce a resulting signal comprised of the interference signal of the specularly reflected light from the tear film 123 with background signal subtracted or substantially removed from the interference signal (block 102, FIG. 6). A resulting image is produced as a result of having interference information from the specularly reflected light from the tear film 123 with background signal eliminated or reduced, including background signal resulting from scattered light from diffuse illumination by the illuminator 36 (block 104, FIG. 6). An example of a resulting image 132 in this regard is illustrated in FIG. 7C. The resulting image 132 represents the first output signal represented by the first image 120 in FIG. 7A combined with the second output signal represented by the second image 130 in FIG. 7B. As illustrated in FIG. 7C, interference signals of specularly reflected light from the tear film 123 are provided for both the first and second portions 126, 128 of the tear film 123. The background signal has been eliminated or reduced. As can be seen in FIG. 7C, the signal purity and contrast of the interference signal representing the specularly reflected light from the tear film 123 from first and second portions 126, 128 appears more vivid and higher in contrast than the interference interaction would without spatially modulating the light emitted from the illuminator 36 by using the Placido disk 40 to project the circular patterns 42A and 42B (FIGS. 8A and 8B).

In the discussion of the example first and second images 120, 130 in FIGS. 7A and 7B above, each first portion 126 can be thought of as a first image, and each second portion 128 can be thought of as a second image. Thus, when the first and second portions 126A, 128B are combined with corresponding first and second portions 126B, 128A, this is akin to subtracting second portions 126B, 128A from the first portions 126A, 128B, respectively.

In the example of FIGS. 6-7C, the first image and second image 120, 130 contain a plurality of portions or tiles. The number of tiles depends on the resolution of lighting interactions provided for and selected for the illuminator 36 to produce the first and second modes of illumination to the tear film 123. The illumination modes can go from one extreme of one tile to any number of tiles desired. Each tile can be the size of one pixel in the imaging device 56 or areas covering more than one pixel depending on the capability of the illuminator 36 and the imaging device 56. The number of tiles can affect accuracy of the interference signals representing the specularly reflected light from the tear film. Providing too few tiles in a tile pattern can limit the representative accuracy of the average illumination geometry that produces the scattered light signal captured by the imaging device 56 in the portions 128A and 126B for precise subtraction from portions 128B and 126A respectively.

Note that while this example in FIGS. 6-7C discusses a first image and a second image captured by the imaging device 56 and a resulting first output signal and second output signal, the first image and the second image may comprise a plurality of images taken in a time-sequenced fashion. If the imaging device 56 is a video camera, the first and second images may contain a number of sequentially-timed frames governed by the frame rate of the imaging device 56. The imaging device 56 produces a series of first output signals and second output signals. If more than one image is captured, the subtraction performed in a first image should ideally be from a second image taken immediately after the first image so that the same or substantially the same lighting conditions exist between the images so the background signal in the second image is present in the first image, and more importantly, so that movement of the eye and especially of the tear-film dynamic is minimal between subtracted frames. The subtraction of the second output signal from the first output signal can be performed in real time. Alternatively, the first and second output signals can be recorded and processed at a later time.

Exemplary OSI Device with an Electronic Placido Disk

The above discussed illustrations provide examples of illuminating and imaging a patient's TFLT. These principles are described in more detail with respect to a specific example of an OSI device 170 illustrated in FIGS. 14-48 and described below throughout the remainder of this application. The OSI device 170 can illuminate a patient's tear film, capture interference information from the patient's tear film, and process and analyze the interference information to measure TFLT. Further, the OSI device 170 includes a number of optional pre-processing features that may be employed to process the interference signal in the resulting signal to enhance TFLT measurement. The OSI device 170 may include a display and user interface to allow a physician or technician to control the OSI device 170 to image a patient's eye and tear film and measure the patient's TFLT.

Illumination and Imaging

Figure 9:
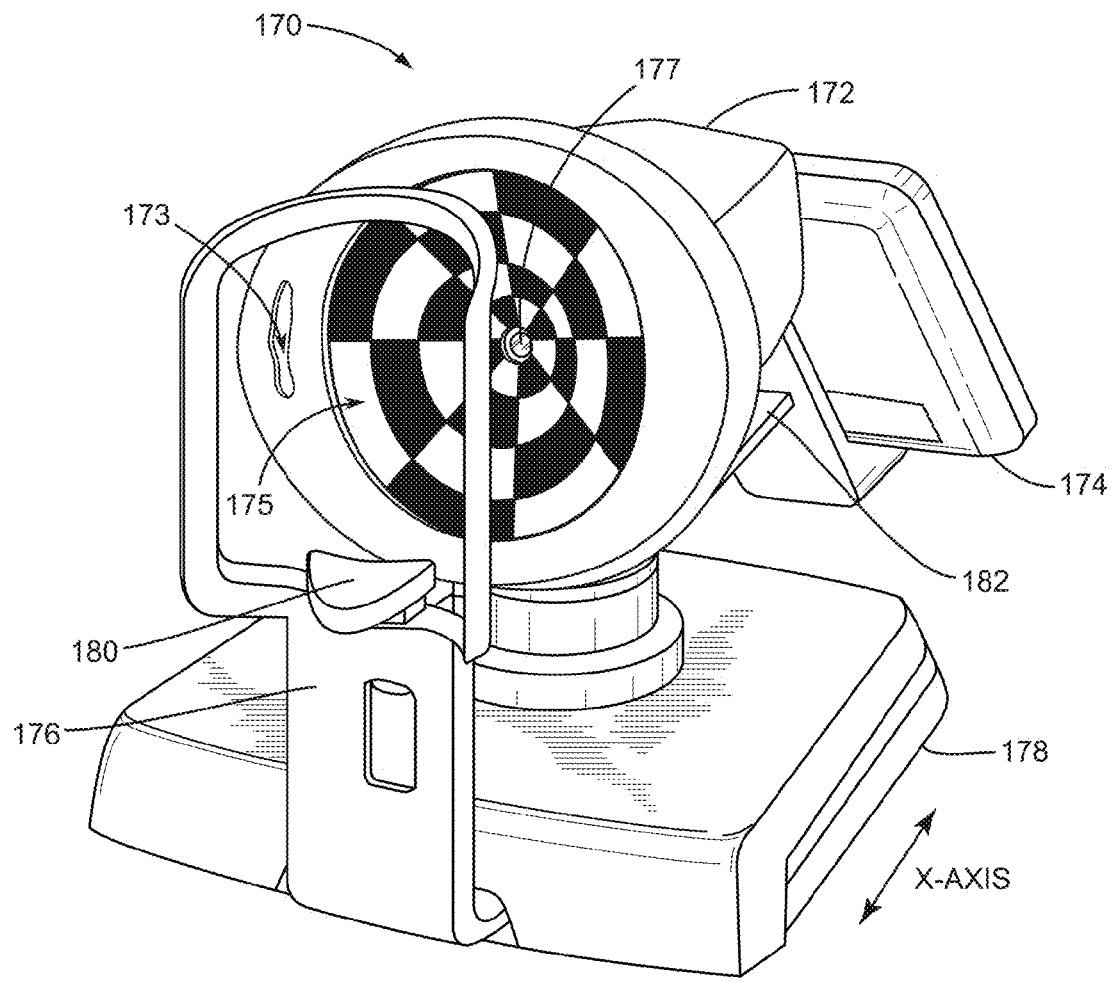
FIG. 9 is a perspective view of an exemplary ocular surface interferometry (OSI) device for illuminating and imaging a patient's tear film, displaying images, analyzing the patient's tear film, generating results from the analysis of the patient's tear film and for providing ocular topography images.

In this regard, FIG. 9 illustrates a perspective view of the OSI device 170. The OSI device 170 is designed to facilitate imaging of the patient's ocular tear film and processing and analyzing the images to determine characteristics regarding a patient's tear film. The OSI device 170 includes an imaging device and light source in this regard, as will be described in more detail below. As illustrated in FIG. 9, the OSI device 170 is comprised generally of a housing 172, a display monitor ("display") 174, and a patient head support 176. The housing 172 may be designed for table top placement. The housing 172 rests on a base 178 in a fixed relationship. As will be discussed in more detail below, the housing 172 houses an imaging device and other electronics, hardware, and software to allow a clinician to image a patient's ocular tear film. A light source 173 (also referred to herein as "illuminator 173") is also provided inside the housing 172 and is provided behind a Placido disk 175. Unlike the Placido disk 40 of the OSI device 30 (FIGS. 4A and 4B), the Placido disk 175 of the OSI device 170 of this embodiment is not physically rotatable. Instead, the Placido disk 175 is an electronic screen made up of a substrate having pixels that are controllable by a controller. The pixels are controllable to transition between dark and light in response to signals transmitted from the controller. Similar to the Placido disk 40 of the OSI device 30 (FIGS. 4A and 4B), the Placido disk 175 includes a centrally located aperture 177 through which the imaging device receives light reflected from the patient's 184 eye 192 (Shown in FIG. 10).

To image a patient's ocular tear film, the patient places his or her head in the patient head support 176 and rests his or her chin on a chin rest 180. The chin rest 180 can be adjusted to align the patient's eye and tear film with the imaging device inside the housing 172, as will be discussed in more detail below. The chin rest 180 may be designed to support up to two (2) pounds of weight, but such is not a limiting factor. A transparent window 177 allows the imaging device inside the housing 172 to have a clear line of sight to a patient's eye and tear film when the patient's head is placed in the patient head support 176. The OSI device 170 is designed to image one eye at a time, but can be configured to image both eyes of a patient, if desired.

In general, the display 174 provides input and output from the OSI device 170. For example, a user interface can be provided on the display 174 for the clinician to operate the OSI device 170 and to interact with a control system provided in the housing 172 that controls the operation of the OSI device 170, including an imaging device, an imaging device positioning system, a light source, other supporting hardware and software, and other components. For example, the user interface can allow control of imaging positioning, focus of the imaging device, and other settings of the imaging device for capturing images of a patient's ocular tear film. The control system may include a general purpose microprocessor or computer with memory for storage of data, including images of the patient's eye and tear film. The microprocessor should be selected to provide sufficient processing speed to process images of the patient's tear film and generate output characteristic information about the tear film (e.g., one minute per twenty second image acquisition). The control system may control synchronization of activation of the light source and the imaging device to capture images of areas of interest on the patient's ocular tear film when properly illuminated. Various input and output ports and other devices can be provided, including but not limited to a joystick for control of the imaging device, USB ports, wired and wireless communication including Ethernet communication, a keyboard, a mouse, speaker(s), etc. A power supply is provided inside the housing 172 to provide power to the components therein requiring power. A cooling system, such as a fan, may also be provided to cool the OSI device 170 from heat generating components therein.

The display 174 is driven by the control system to provide information regarding a patient's imaged tear film, including TFLT. The display 174 also provides a graphical user interface (GUI) to allow a clinician or other user to control the OSI device 170. To allow for human diagnosis of the patient's tear film, images of the patient's ocular tear film taken by the imaging device in the housing 172 can also be displayed on the display 174 for review by a clinician, as will be illustrated and described in more detail below. The images displayed on the display 174 may be real-time images being taken by the imaging device, or may be previously recorded images stored in memory. To allow for different orientations of the OSI device 170 to provide a universal configuration for manufacturing, the display 174 can be rotated about the base 178. The display 174 is attached to a monitor arm 182 that is rotatable about the base 178, as illustrated. The display 174 can be placed opposite of the patient head support 176, as illustrated in FIG. 9, if the clinician desires to sit directly across from the patient. Alternatively, the display 174 can be rotated either left or right about the X-axis to be placed adjacent to the patient head support 176. The display 174 may be a touch screen monitor to allow a clinician or other user to provide input and control to the control system inside the housing 172 directly via touch of the display 174 for control of the OSI device 170. The display 174 illustrated in FIG. 9 is a fifteen inch (15") flat panel liquid crystal display (LCD). However, the display 174 may be provided of any type or size, including but not limited to a cathode ray tube (CRT), plasma, LED, OLED, projection system, etc.

Figure 10:
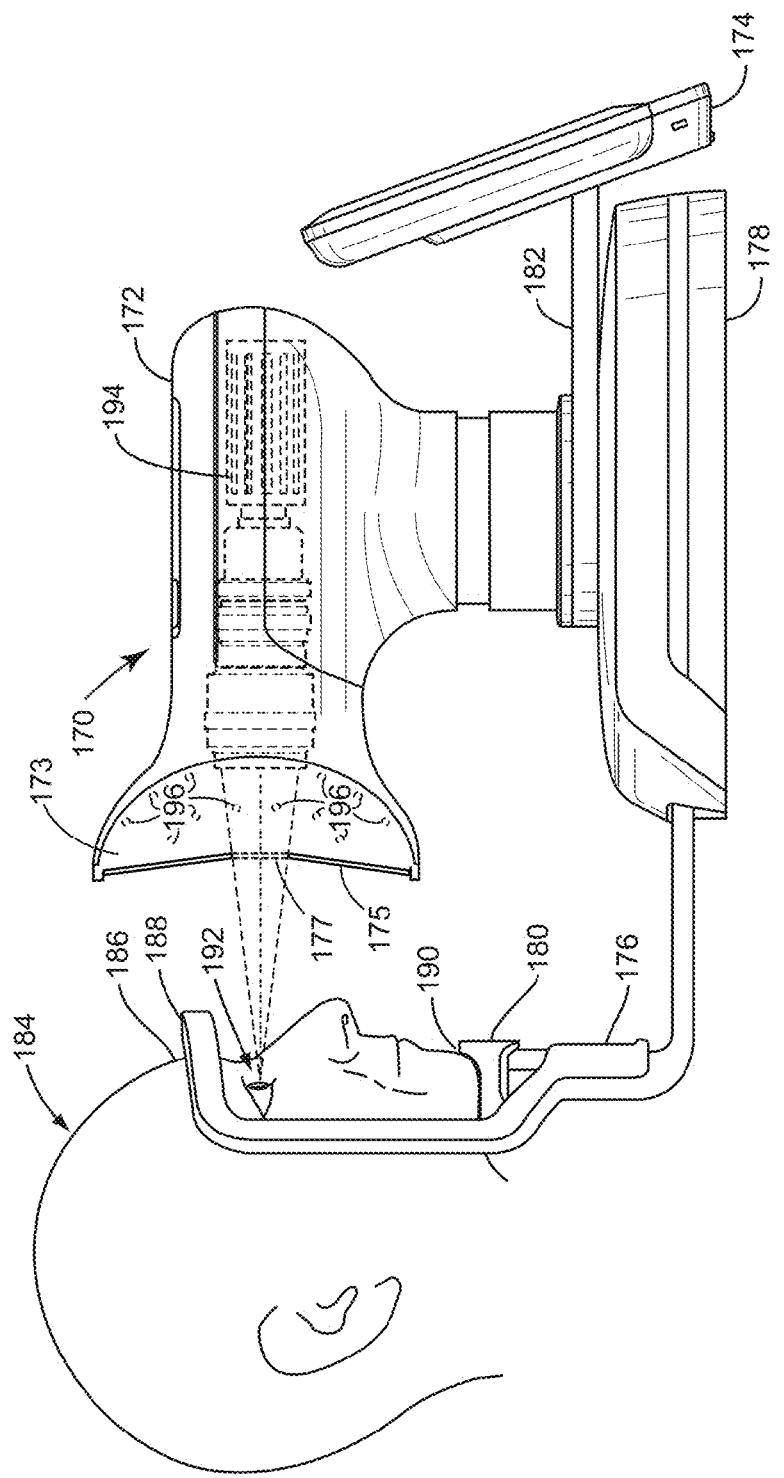
FIG. 10 is a side view of the OSI device of FIG. 9 illuminating and imaging a patient's eye and tear film.

FIG. 10 illustrates a side view of the OSI device 170 of FIG. 9 to further illustrate imaging of a patient's eye and ocular tear film. As illustrated therein, a patient 184 places their head in the patient head support 176. More particularly, the patient places their forehead 186 against a headrest 188 provided as part of the patient head support 176. The patient places their chin 190 in the chin rest 180. The patient head support 176 is designed to facilitate alignment of a patient's 184 eye 192 with the OSI device 170, and in particular, an imaging device 194 (and the illuminator 173 with LEDS 196) shown as being provided inside the housing 172. The chin rest 180 can be adjusted higher or lower to move the patient's 184 eye 192 with respect to the OSI device 170.

Figure 11:
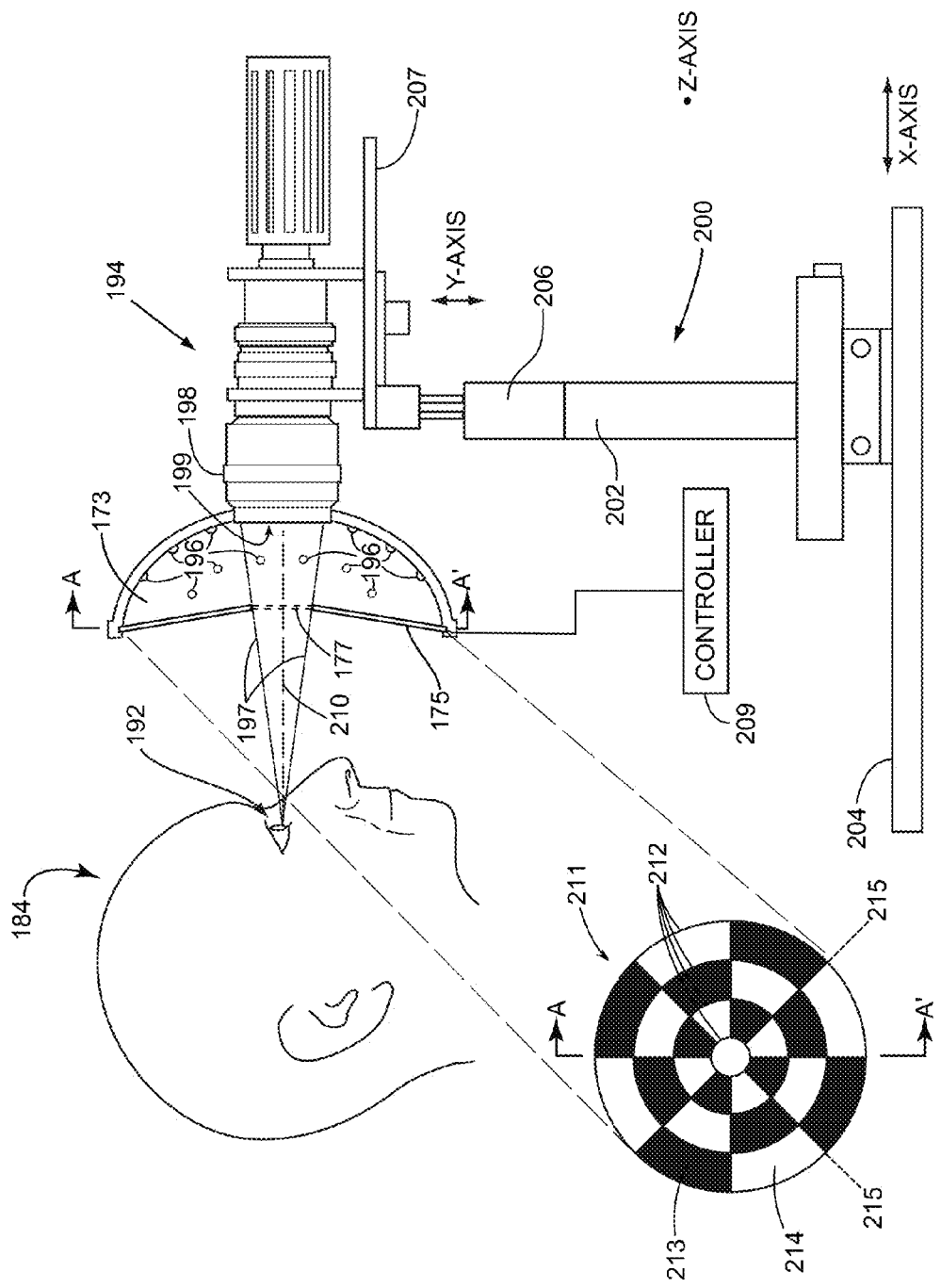
FIG. 11 is a side view of a video camera and illuminator within the OSI device of FIG. 9 imaging a patient's eye and tear film.

As shown in FIG. 11, the imaging device 194 is used to image the patient's ocular tear film to determine characteristics of the patient's tear film. In particular, the imaging device 194 is used to capture interference interactions of the specularly reflected light 197 from the patient's tear film when illuminated by the illuminator 173 (also referred to herein as "illuminator 173") as well as background signal. As previously discussed, background signal may be captured when the illuminator 173 is illuminating or not illuminating a patient's tear film. In the OSI device 170, the imaging device 194 is "The Imaging Source" model DFK21BU04 charge coupling device (CCD) digital video camera 198, but many types of metrological grade cameras or imaging devices can be provided. The CCD digital video camera 198 employs an imaging lens 199 to focus the captured specularly reflected light 197 onto a CCD chip (not shown). A CCD camera enjoys characteristics of efficient light gathering, linear behavior, cooled operation, and immediate image availability. A linear imaging device is one that provides an output signal representing a captured image which is precisely proportional to the input signal from the captured image. Thus, use of a linear imaging device (e.g., gamma correction set to 1.0, or no gamma correction) provides undistorted interference data which can then be analyzed using linear analysis models. In this manner, the resulting images of the tear film do not have to be linearized before analysis, thus saving processing time. Gamma correction can then be added to the captured linear images for human-perceptible display on a non-linear display 174 in the OSI device 170. Alternatively, the opposite scenario could be employed. That is, a non-linear imaging device or non-linear setting would be provided to capture tear film images, wherein the non-linear data representing the interference interactions of the interference signal can be provided to a non-linear display monitor without manipulation to display the tear film images to a clinician. The non-linear data would be linearized for tear film processing and analysis to estimate tear film layer thickness.

The video camera 198 is capable of producing lossless full motion video images of the patient's eye. As illustrated in FIG. 11, the video camera 198 has a depth of field defined by the angle between specularly reflected light rays 197 and the lens focal length that allows the patient's entire tear film to be in focus simultaneously. The video camera 198 has an external trigger support so that the video camera 198 can be controlled by a control system to image the patient's 184 eye 192. The video camera 198 includes the imaging lens 199 that fits within the housing 172. The video camera 198 in this embodiment has a resolution of 640×480 pixels and is capable of frame rates up to sixty (60) frames per second (fps). The lens system employed in the video camera 198 images a 16×12 mm dimension in a sample plane onto an active area of a CCD detector within the video camera 198. As an example, the video camera 198 may be the DBK21AU04 Bayer VGA (640×480) video camera using a Pentax VS-LD25 Daitron 25-mm fixed focal length lens. Other camera models with alternate pixel size and number, alternate lenses, (etc.) may also be employed.

Although a video camera 198 is provided in the OSI device 170, a still camera could also be used if the frame rate is sufficiently fast enough to produce high quality images of the patient's eye. High frame rate in frames per second (fps) facilitates high quality subtraction of background signal from a captured interference signal representing specularly reflected light from a patient's tear film, and may provide less temporal (i.e., motion) artifacts (e.g., motion blurring) in captured images, resulting in high quality captured images. This is especially the case since the patient's eye may move irregularly as well as blinking, obscuring the tear film from the imaging device during examination.

A camera positioning system 200 is also provided in the housing 172 of the OSI device 170 to position the video camera 198 for imaging of the patient's tear film. The camera positioning system 200 is under the control of a control system. In this manner, a clinician can manipulate the position of the video camera 198 to prepare the OSI device 170 to image the patient's tear film. The camera positioning system 200 allows a clinician and/or control system to move the video camera 198 between each of the patient's 184 eyes 192, but can also be designed to limit the range of motion within designed tolerances. The camera positioning system 200 also allows for fine tuning of the video camera 198 position. The camera positioning system 200 includes a stand 202 attached to a base 204. A linear servo or actuator 206 is provided in the camera positioning system 200 and connected between the stand 202 and a camera platform 207 supporting the video camera 198 to allow the video camera 198 to be moved in the vertical (i.e., Y-axis) direction.

In this embodiment of the OSI device 170, the camera positioning system 200 may not allow the video camera 198 to be moved in the X-axis or the Z-axis (in and out of FIG. 11), but the disclosure is not so limited. The illuminator 173 is also attached to the camera platform 207 such that the illuminator 173 maintains a fixed geometric relationship to the video camera 198. Thus, when the video camera 198 is adjusted to the patient's 184 eye 192, the illuminator 173 is automatically adjusted to the patient's 184 eye 192 in the same regard as well. This may be important to enforce a desired distance (d) to properly capture the interference interactions of the specularly reflected light from the patient's tear film at the proper angle of incidence according to Snell's law, since the OSI device 170 is programmed to assume a certain distance and certain angles of incidence.

In this exemplary embodiment, the Placido disk 175 is frusto-conical shaped with an open major base and an open minor base with the open minor base facing the imaging device 194, while the open major base faces the patient 184. The Placido disk 175 is centered about an optical axis 210 that extends between the patient's 184 eye 192 and the imaging lens 199. Moreover, a controller 209 controls the pixels of the Placido disk 175 to generate a circular pattern, which is shown in this exemplary embodiment as a circular tiled pattern 211. The circular tiled pattern 211 includes concentric circles 212 with alternating dark tiles 213 and light tiles 214 that have edges that form radials 215. In at least one embodiment, the pixels that generate the circular tiled pattern are liquid crystals such as those that make up a traditional liquid crystal display (LCD). The liquid crystals are controllable to align in a first direction to generate opaque pixels that make up the dark tiles 213. Alternately, the liquid crystals are controllable to align in a second direction to generate translucent pixels that make up the light tiles 214. In at least one other embodiment, pixels of the Placido disk 175 are active devices such as OLEDs that can be controlled to emit multi-wavelength light in place of the illuminator 173.

Tear Film Thickness Measurement

A tear film thickness measurement using OSI device 170 is accomplished by the procedure depicted in FIG. 6. In particular, a tear film measurement is initiated by adjusting the patient's 184 eye 192 to the imaging device 194 (block 92). Next, a first circular pattern is projected onto the eye 192 when illuminated by the illuminator 173 (block 94). While illuminating the tear film 123 in the first mode, the imaging device 194 captures the first image 120 of the patient's eye 121 and the tear film 123 as shown in FIG. 7A (block 96). The controller 209 inverts the pixels after the projection of the first circular pattern in order to project a second circular pattern onto the eye 192 when illuminated by the illuminator 173 (block 98). In the exemplary embodiment of the OSI device 170, the Placido disk 175 does not rotate to invert the first circular pattern to generate the second circular pattern. Instead, the controller 209 transitions the light pixels to dark pixels and vice versa to invert the first circular pattern and thereby generate the second circular pattern. A second image 130 is captured of the tear film 123 is captured in the second mode, as illustrated by example in FIG. 7B (block 100, FIG. 6). It is to be understood that the controller 209 synchronizes the frequency of alternating projections of the first circular pattern and the second circular pattern with the capturing of images via the imaging device 194.

As shown in the second image 130 in FIG. 7B, the second portions 128A in the first image 120 of FIG. 7A are now second portions 128B in the second image 130 in FIG. 7B containing specularly reflected light from the tear film 123 with additive background signal. The first portions 126A in the first image 120 of FIG. 7A are now first portions 126B in the second image 130 in FIG. 7B containing background signal without specularly reflected light. Again, the background signal in the first portions 126B includes scattered light signal as a result of diffuse illumination by the illuminator 173. The imaging device 194 produces a second output signal of the second image 130 in FIG. 7B. The illuminator 173 may also be flashed in block 98 to produce specularly reflected light from the second portions 128B, whereby the imaging device 194 is synchronized with the frequency of the projection of the second circular pattern in block 98 to capture the second image 130 of the patient's 184 eye 192 and the tear film 123. The first and second output signals can then be combined to produce a resulting signal comprised of the interference signal of the specularly reflected light from the tear film 123 with background signal subtracted or substantially removed from the interference signal (block 102, FIG. 6). A resulting image is produced and displayed as a result of having interference information from the specularly reflected light from the tear film 123 with background signal eliminated or reduced, including background signal resulting from scattered light from diffuse illumination by the illuminator 173 (block 104, FIG. 6). An example of a resulting image 132 in this regard is illustrated in FIG. 7C. The resulting image 132 represents the first output signal represented by the first image 120 in FIG. 7A combined with the second output signal represented by the second image 130 in FIG. 7B. As illustrated in FIG. 7C, interference signals of specularly reflected light from the tear film 123 are provided for both the first and second portions 126, 128 of the tear film 123. The background signal has been eliminated or reduced. In this manner, a medical doctor is able to have a visualization of the patient's 184 tear film 123.

Corneal Topography

Figure 12:
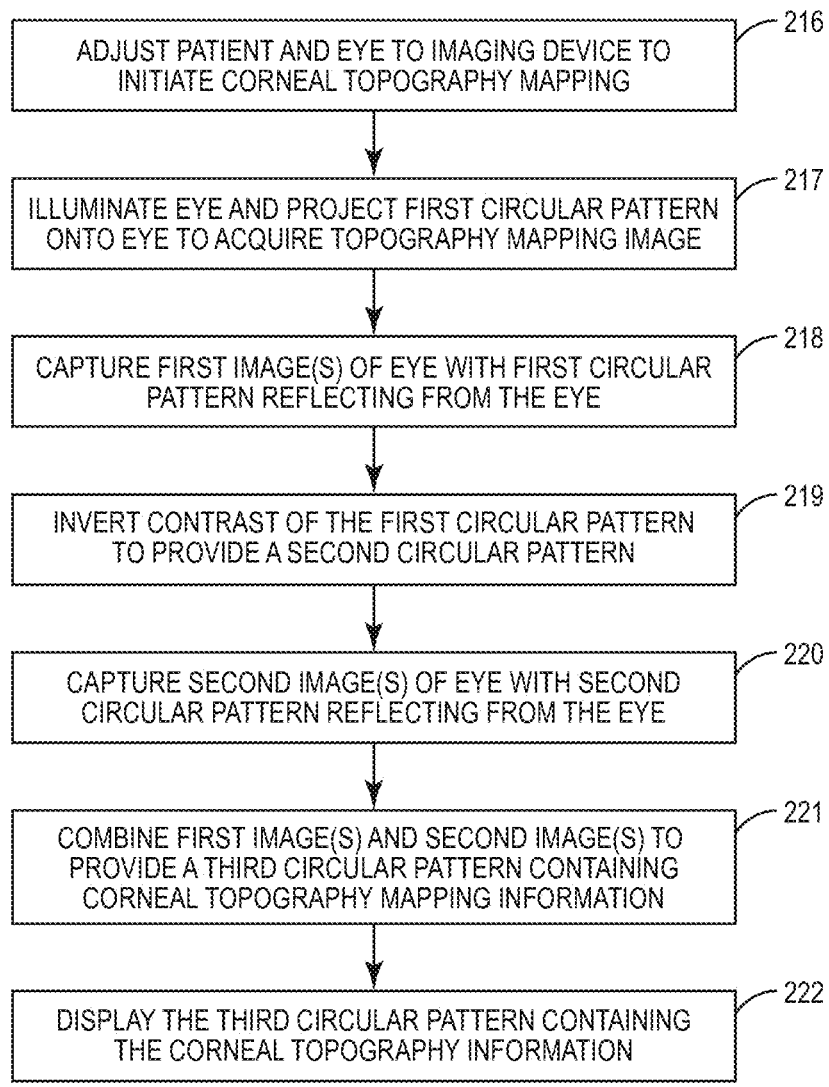
FIG. 12 is a flowchart of an exemplary process for corneal topography mapping using the OSI device of FIGS. 4A and 4B or the OSI device of FIGS. 9-11.
Figure 13:
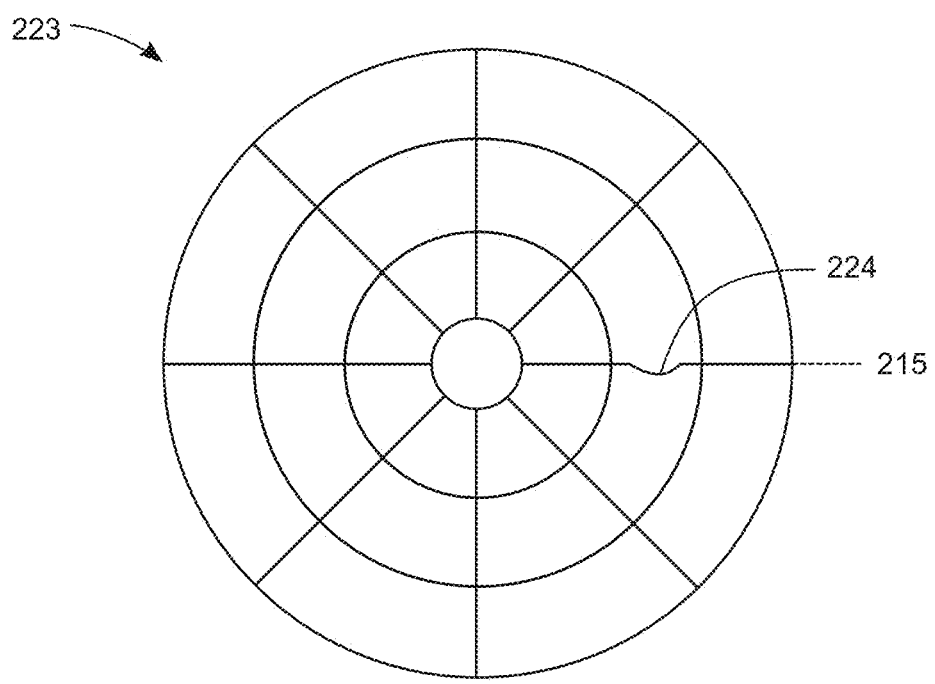
FIG. 13 is an exemplary corneal topography mapping Placido pattern resulting from the exemplary process for corneal topography mapping depicted in the flowchart of FIG. 12.

Beyond tear film measurement, the OSI device 170 is ideal for conducting corneal topography mapping. A flowchart depicting a process for corneal topography mapping using the OSI device 170 is shown in FIG. 12. The corneal topography mapping process is initiated by adjusting the patient's 184 eye 192 to the imaging device 194 (block 216). Once proper adjustments are made, the patient's 184 eye 192 is illuminated via the illuminator 173 and a first circular pattern is projected onto the eye 192 before acquiring a corneal topography mapping image (block 217). Once the eye 192 is illuminated, a first image(s) of the eye 192 is captured with the first circular pattern reflected from the eye 192 (block 218). After capturing the first image(s) the first circular pattern is inverted to provide a second circular pattern that is projected onto the eye 192 (block 219). Next, a second image(s) of the eye 192 with the second circular pattern reflecting therefrom is captured by the imaging device 194 (block 220). The OSI device 170 then combines the first image(s) and the second image(s) to provide a third circular pattern containing corneal topography information (block 221). Lastly, the third circular pattern containing the corneal topography information is displayed on the display 174 (block 222). FIG. 13 depicts an example of a third circular pattern 223 containing an indication of a corneal aberration 224 that is visually represented as a bump in a radial 215.

Figure 14:
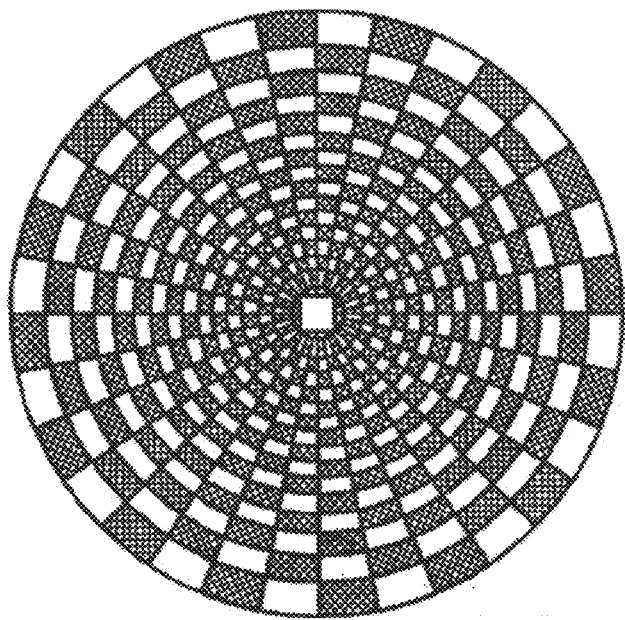
FIG. 14 is a rearview of a prior art checkered Placido apparatus.
Figure 15:
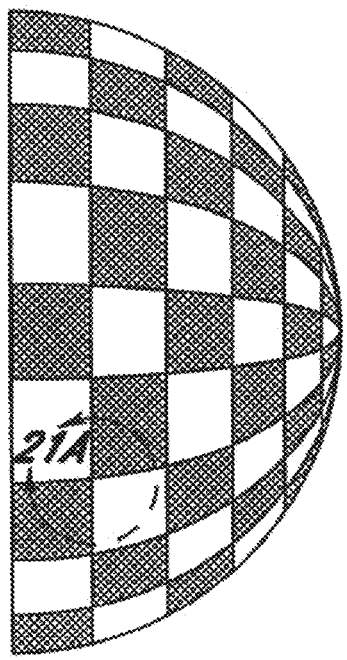
FIG. 15 is a side view of the prior art checkered Placido image projected onto a cornea.

FIGS. 14 and 15 are prior art figures from U.S. Pat. No. 6,450,641 to D'Souza et al (hereafter D'Souza). In particular, D'Souza is directed to a method of corneal analysis using a checkered Placido apparatus. FIG. 14 is a rearview of the D' Souza checkered Placido disk and FIG. 15 is a side view of the D'Souza checkered Placido image projected onto a cornea. While FIG. 14 depicts a pattern similar to the present circular pattern 211 (FIG. 11), the D'Souza checkered Placido disk is not usable for measuring tear film thickness. For example, the D'Souza checkered Placido disk does not have a means for projecting a first circular pattern onto a cornea, inverting the first circular pattern to generate a second circular pattern and then projecting the second circular pattern onto the cornea like the OSI devices of the present disclosure. In other words, D'Souza does not rotate the checkered Placido disk or invert pixels so that dark areas and light areas are swapped between a first circular checkered pattern and a second circular checkered pattern. Further still, D'Souza does not combine a first image(s) of a first circular pattern reflected from a cornea with a second image(s) of a second circular pattern reflected from the cornea to generate a third circular pattern without tiles (i.e. no checkered pattern). As a result, D'Souza does not teach or suggest tear film thickness measurement. In particular, D'Souza does not include the color processing of the present embodiments that relate color to light specularly reflected from the tear film that undergo constructive and destructive optical wave interference interactions. Thus, D'Souza does not teach or suggest the combined tear film measurement and corneal topography mapping OSI device embodiments of the present disclosure.

Combined Tear Film Measurement and Corneal Topography

Since the OSI device embodiments of the present disclosure provide more area of tear film 123 than with traditional tear film measurement instruments and techniques, it may be important to understand if there are tear film deficiencies located at corneal aberrations such as scar tissue. As such, a medical doctor may need to visually inspect the resultant image containing both tear film measurement information combined with corneal topography information. The OSI device 170 can be controlled by the medical doctor to display an image of both the tear film along with corneal topography mapping information. Therefore, not only can the medical doctor use the resultant image to examine the RGB color representations of the lipid layer, the medical doctor is now also able to visually correlate abnormalities in lipid layer thickness with abnormalities in the corneal shape of the eye.

Figure 16:
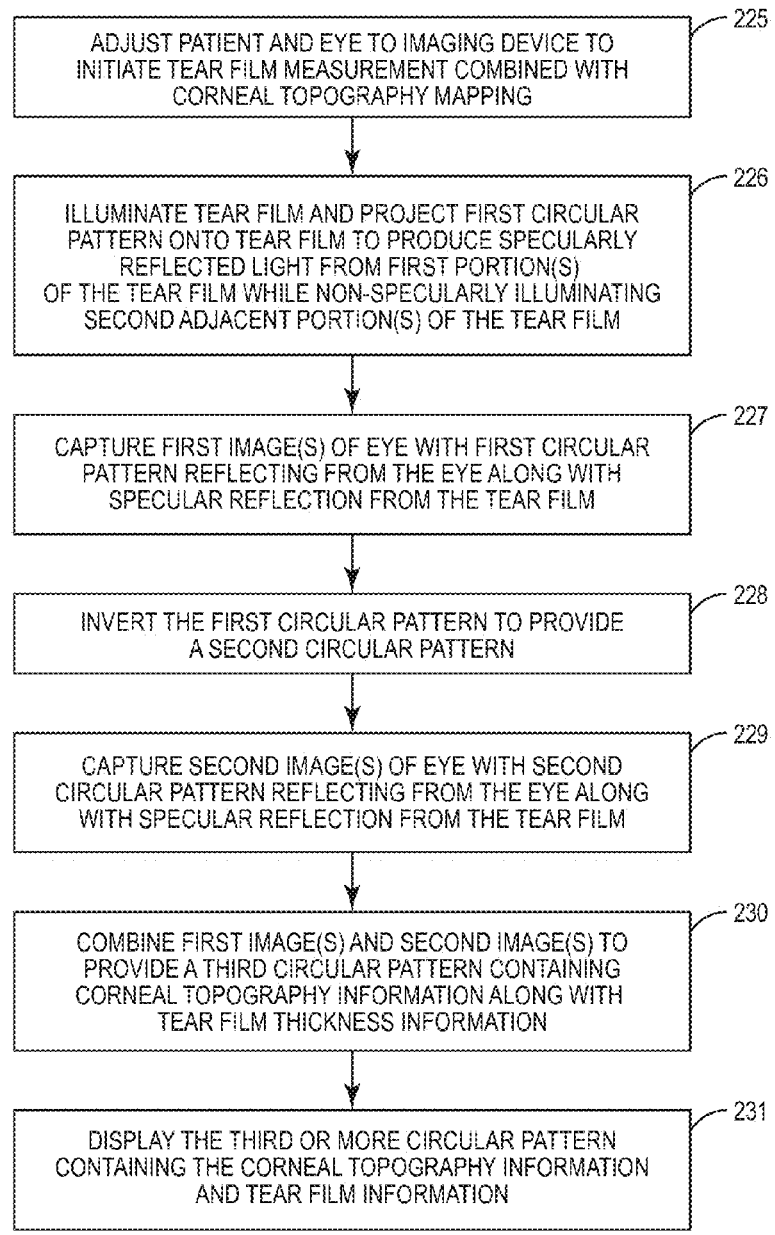
FIG. 16 is a flowchart of an exemplary process of measuring tear film thickness combined with corneal topography mapping using the OSI device of FIGS. 4A and 4B or the OSI device of FIGS. 9-11.

In this regard, FIG. 16 is a flowchart of an exemplary process of measuring tear film thickness combined with corneal topography mapping using the OSI device 30 of FIGS. 4A and 4B or the OSI device 170 of FIGS. 9-11. The exemplary process for conducting a tear film measurement combined with corneal topography mapping is initiated by adjusting the patient's 184 eye 192 to the imaging device 194 (block 225). Once the patient's 184 eye 192 is adjusted to the imaging device 194, the tear film is illuminated by the illuminator 173 and a first circular pattern is projected onto the tear film to produce specularly reflected light from first portion(s) in the tear film while non-specularly illuminating second adjacent portion(s) of the tear film (block 226). Next, the imaging device 194 captures a first image(s) of the eye 192 with the first circular pattern reflecting from the eye along with the specular light reflections from the tear film (block 227). Once the first image(s) are captured, the first circular pattern is inverted to provide a second circular pattern (block 228). Next, a second image(s) of the eye 192 is captured while the second circular pattern is reflecting from the eye 192 along with the specular reflection from the tear film (block 229). Afterwards, the first image(s) and the second image(s) are combined to provide a third circular pattern containing both corneal topography and tear film thickness information (block 230). Lastly, the third circular pattern containing the corneal topography information and the tear film information is displayed on the display 174 (block 231).

System Level

Figure 17A:
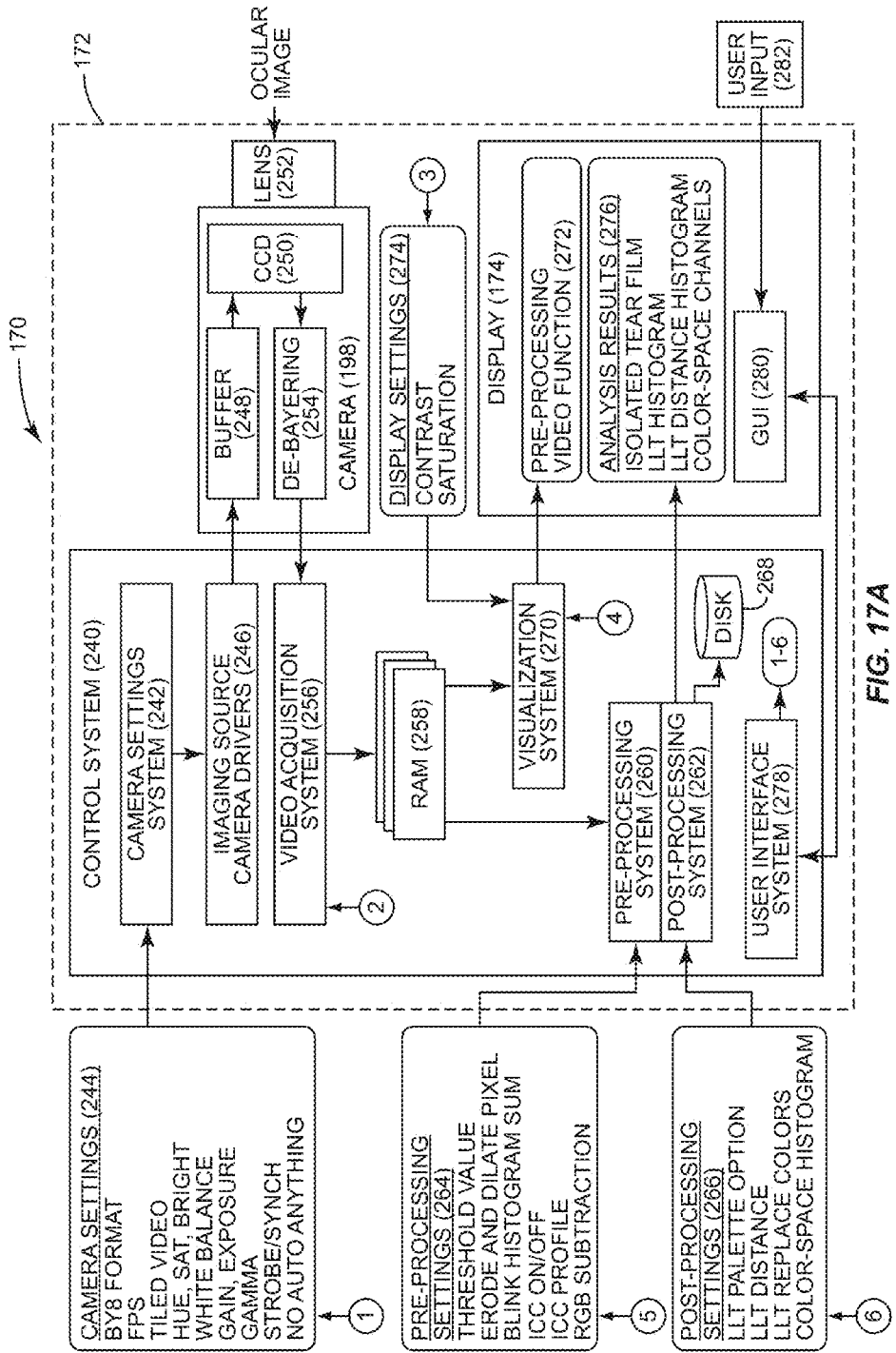
FIG. 17A illustrates an exemplary system diagram of a control system and supporting components in the OSI device of FIGS. 9-11.

Now that the imaging and illumination functions of the OSI device 170 have been described, FIG. 17A illustrates a system level diagram illustrating more detail regarding the control system and other internal components of the OSI device 170 provided inside the housing 172 according to one embodiment to capture images of a patient's tear film and process those images. As illustrated therein, a control system 240 is provided for the overall control of the OSI device 170. The control system 240 may be provided by any microprocessor-based or computer system. The control system 240 illustrated in FIG. 17A is provided in a system-level diagram and does not necessarily imply a specific hardware organization and/or structure. As illustrated therein, the control system 240 contains several systems. A camera settings system 242 may be provided that accepts camera settings from a clinician user. Exemplary camera settings 244 are illustrated, but may be any type according to the type and model of camera provided in the OSI device 170 as is well understood by one of ordinary skill in the art.

The camera settings 244 may be provided to (The Imaging Source) camera drivers 246, which may then be loaded into the video camera 198 upon initialization of the OSI device 170 for controlling the settings of the video camera 198. The settings and drivers may be provided to a buffer 248 located inside the video camera 198 to store the settings for controlling a CCD 250 for capturing ocular image information from a lens 252. Ocular images captured by the lens 252 and the CCD 250 are provided to a de-Bayering function 254 which contains an algorithm for post-processing of raw data from the CCD 250 as is well known. The ocular images are then provided to a video acquisition system 256 in the control system 240 and stored in memory, such as random access memory (RAM) 258. The stored ocular images or signal representations can then be provided to a pre-processing system 260 and a post-processing system 262 to manipulate the ocular images to obtain the interference interactions of the specularly reflected light from the tear film and analyze the information to determine characteristics of the tear film. Pre-processing settings 264 and post-processing settings 266 can be provided to the pre-processing system 260 and post-processing system 262, respectively, to control these functions. These settings 264, 266 will be described in more detail below. The post-processed ocular images and information may also be stored in mass storage, such as disk memory 268, for later retrieval and viewing on the display 174.

The control system 240 may also contain a visualization system 270 that provides the ocular images to the display 174 to be displayed in human-perceptible form on the display 174. Before being displayed, the ocular images may have to be pre-processed in a pre-processing video function 272. For example, if the ocular images are provided by a linear camera, non-linearity (i.e. gamma correction) may have to be added in order for the ocular images to be properly displayed on the display 174. Further, contrast and saturation display settings 274, which may be controlled via the display 174 or a device communicating to the display 174, may be provided by a clinician user to control the visualization of ocular images displayed on the display 174. The display 174 is also adapted to display analysis result information 276 regarding the patient's tear film, as will be described in more detail below. The control system 240 may also contain a user interface system 278 that drives a graphical user interface (GUI) utility 280 on the display 174 to receive user input 282. The user input 282 can include any of the settings for the OSI device 170, including the camera settings 244, the pre-processing settings 264, the post-processing settings 266, the display settings 274, the visualization system 270 enablement, and video acquisition system 256 enablement, labeled 1-6. The GUI utility 280 may only be accessible by authorized personnel and used for calibration or settings that would normally not be changed during normal operation of the OSI device 170 once configured and calibrated.

Overall Process Flow

Figure 17B:
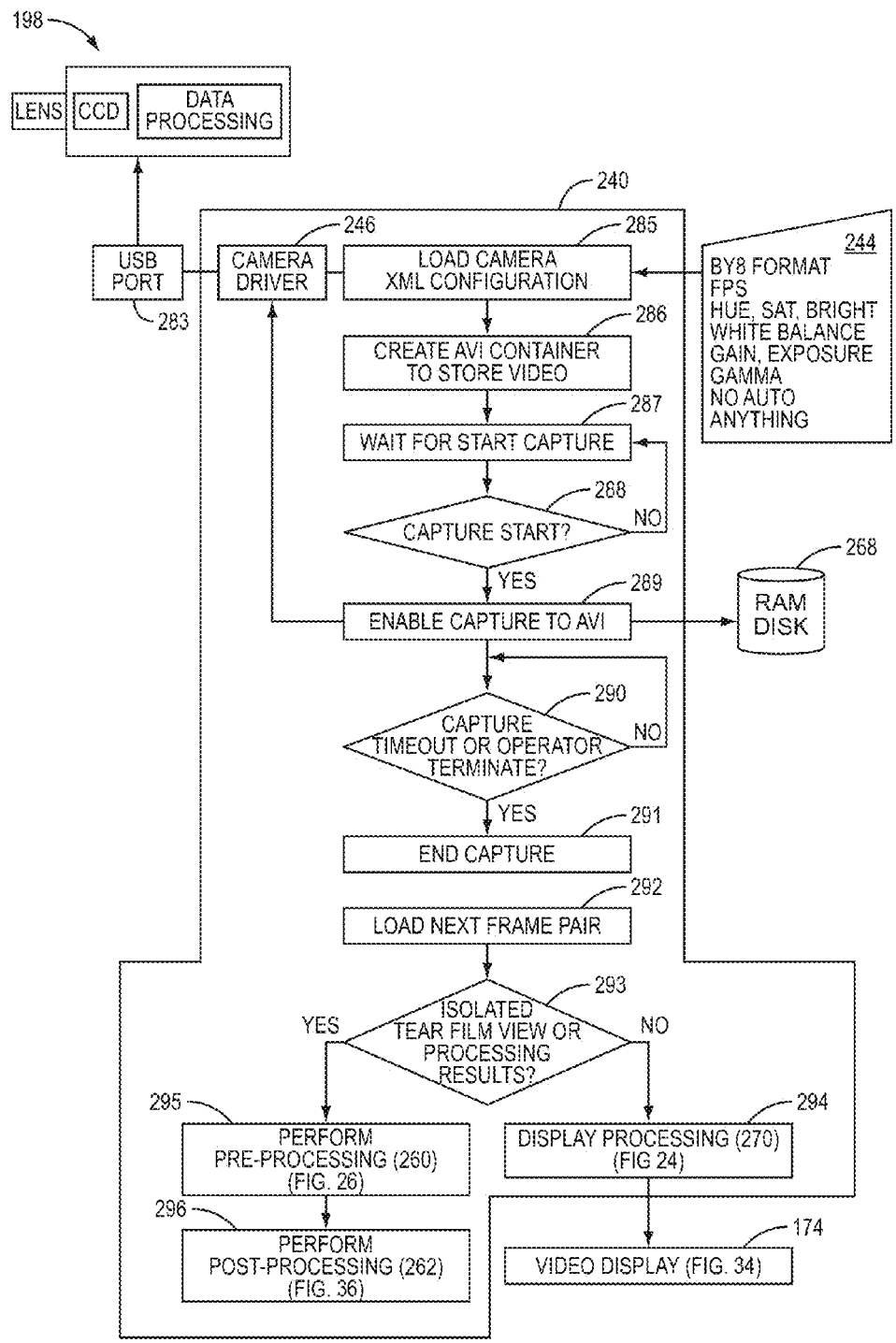
FIG. 17B is a flowchart illustrating an exemplary overall processing flow of the OSI device of FIGS. 9-11 having systems components according to the exemplary system diagram of the OSI device in FIG. 17A.

FIG. 17B illustrates an exemplary overall flow process performed by the OSI device 170 for capturing tear film images from a patient and analysis for TFLT measurement. As illustrated in FIG. 17B, the video camera 198 is connected via a USB port 283 to the control system 240 (see FIG. 17A) for control of the video camera 198 and for transferring images of a patient's tear film taken by the video camera 198 back to the control system 240. The control system 240 includes a compatible camera driver 246 to provide a transfer interface between the control system 240 and the video camera 198. Prior to tear film image capture, the configuration of camera settings 244 is loaded into the video camera 198 over the USB port 283 to prepare the video camera 198 for tear film image capture (block 285). Further, an audio video interleaved (AVI) container is created by the control system 240 to store video of tear film images to be captured by the video camera 198 (block 286). At this point, the video camera 198 and control system 240 are ready to capture images of a patient's tear film. The control system 240 waits for a user command to initiate capture of a patient's tear film (blocks 287, 288).

Once image capture is initiated (block 288), the control system 240 enables image capture to the AVI container previously setup (block 286) for storage of images captured by the video camera 198 (block 289). The control system 240 controls the video camera 198 to capture images of the patient's tear film (block 289) until timeout or the user terminates image capture (block 290) and image capture halts or ends (block 291). Images captured by the video camera 198 and provided to the control system 240 over the USB port 283 are stored by the control system 240 in RAM 258.

The captured images of the patient's ocular tear film can subsequently be processed and analyzed to perform TFLT measurement, as described in more detail below and throughout the remainder of this disclosure. The process in this embodiment involves processing tear film image pairs to perform background subtraction, as previously discussed. For example, image tiling may be performed to provide the tear film image pairs, if desired. The processing can include simply displaying the patient's tear film or performing TFLT measurement (block 293). If the display option is selected to allow a technician to visually view the patient's tear film, display processing is performed (block 294) which can be the visualization system 270 described in more detail below with regard to FIG. 26. For example, the control system 240 can provide a combination of images of the patient's tear film that show the entire region of interest of the tear film on the display 174. The displayed image may include the background signal or may have the background signal subtracted. If TFLT measurement is desired, the control system 240 performs pre-processing of the tear film images for TFLT measurement (block 295), which can be the pre-processing system 260 described in more detail below with regard to FIG. 18. The control system 240 also performs post-processing of the tear film images for TFLT measurement (block 296), which can be the post-processing system 262 described in more detail below with regard to FIG. 28.

Pre-Processing

Figure 18:
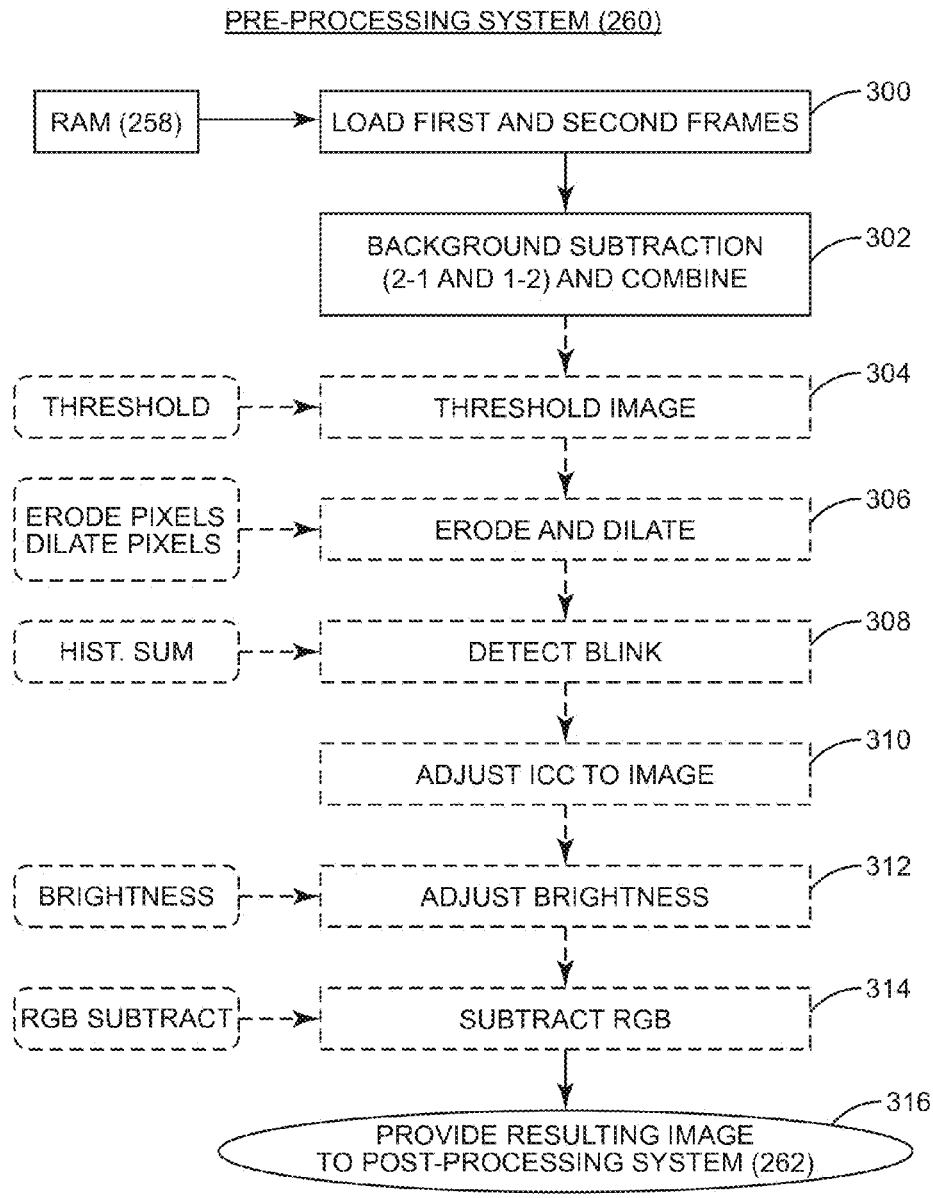
FIG. 18 is a flowchart illustrating exemplary pre-processing steps performed on the combined first and second images of a patient's tear film before measuring tear film layer thickness (TFLT)
Figure 19:
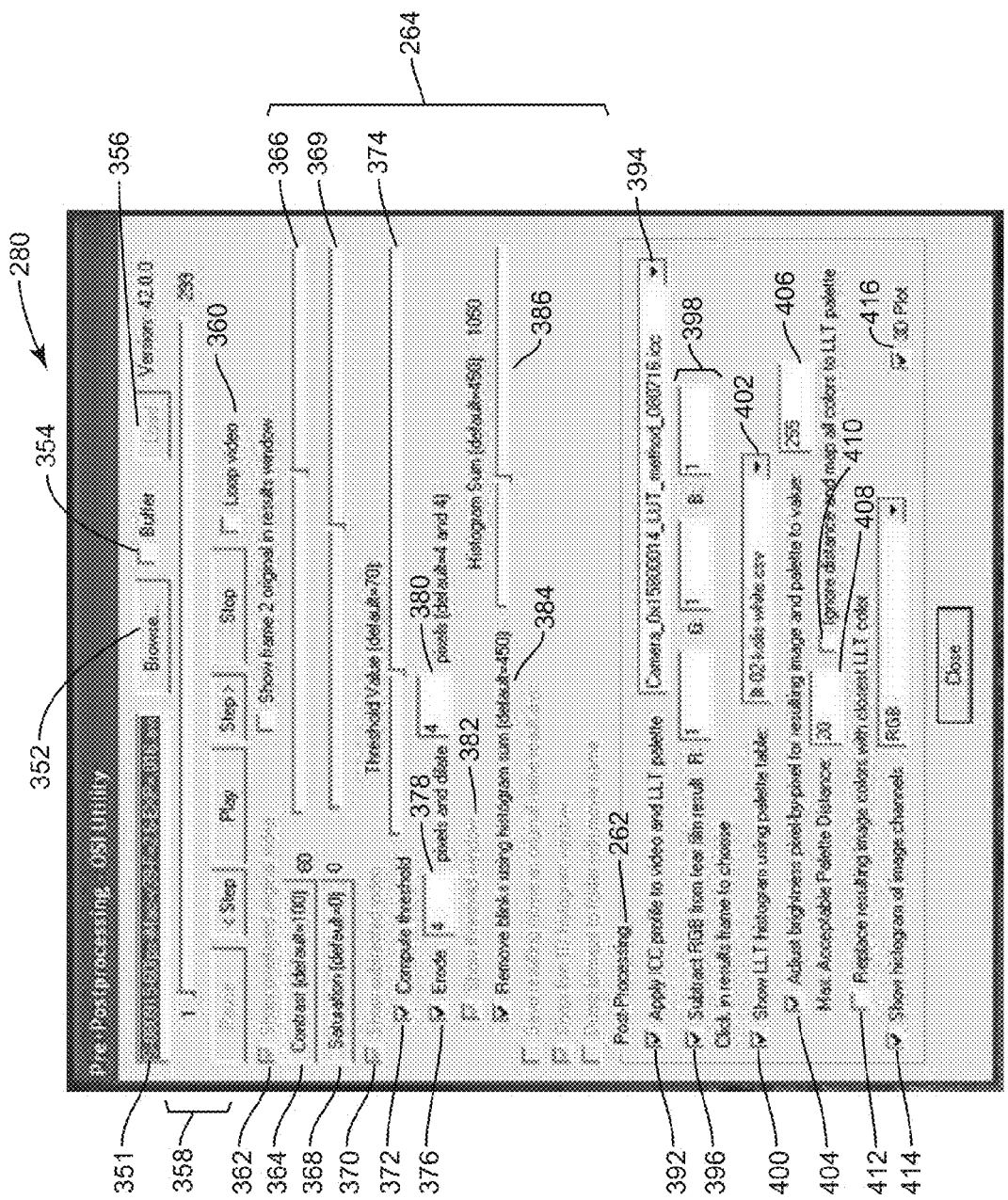
FIG. 19 is an exemplary graphical user interface (GUI) for controlling imaging, pre-processing, and post-processing settings of the OSI device of FIGS. 9-11.
Figure 20:
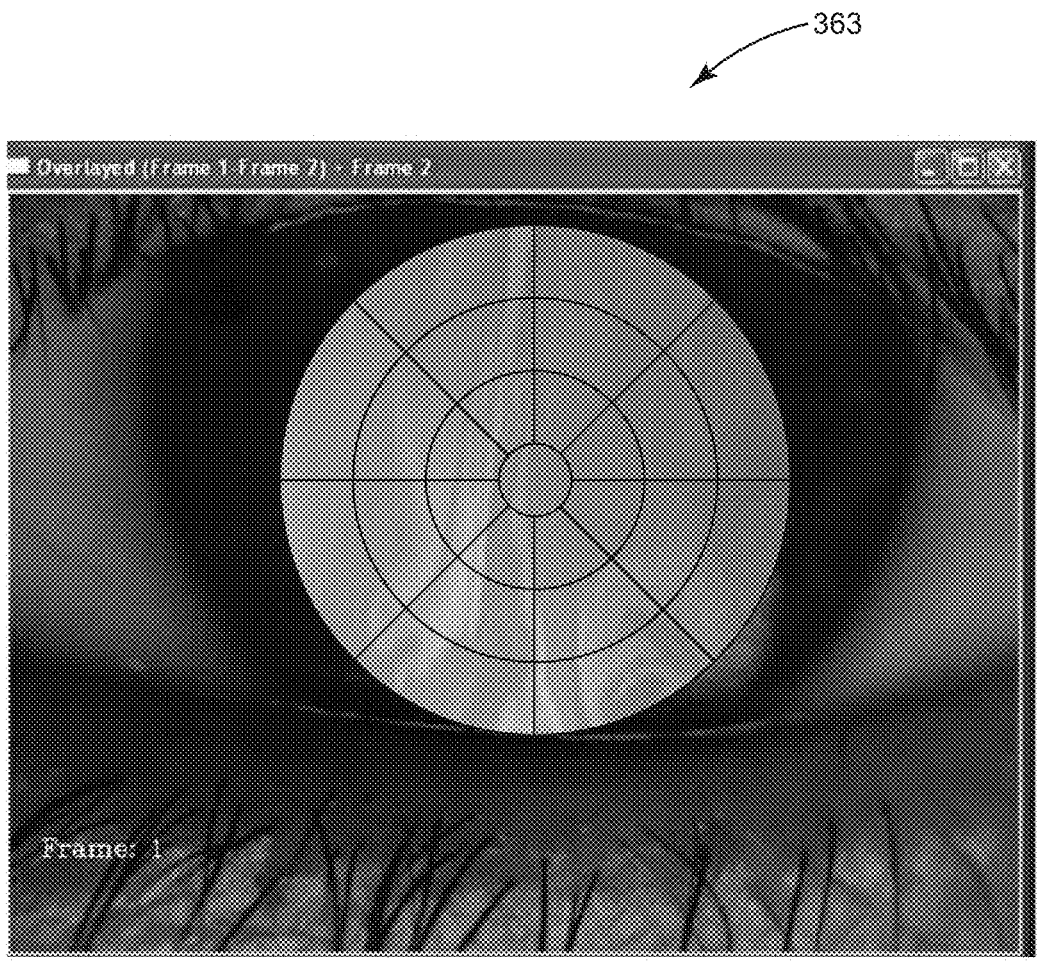
FIG. 20 illustrates an example of a processed image in an area or region of interest of a tear film containing specularly reflected light from the tear film overlaid on top of a background image of the tear film.

FIG. 18 illustrates an exemplary pre-processing system 260 for pre-processing ocular tear film images captured by the OSI device 170 for eventual analysis and TFLT measurement. In this system, the video camera 198 has already taken the first and second tiled images of a patient's ocular tear film, as previously illustrated in FIGS. 11A and 11B, and provided the images to the video acquisition system 256. The frames of the first and second images were then loaded into RAM 258 by the video acquisition system 256. Thereafter, as illustrated in FIG. 18, the control system 240 commands the pre-processing system 260 to pre-process the first and second images. An exemplary GUI utility 280 is illustrated in FIG. 19 that may be employed by the control system 240 to allow a clinician to operate the OSI device 170 and control pre-processing settings 264 and post-processing settings 266, which will be described later in this application. In this regard, the pre-processing system 260 loads the first and second image frames of the ocular tear film from RAM 258 (block 300). The exemplary GUI utility 280 in FIG. 19 allows for a stored image file of previously stored video sequence of first and second image frames captured by the video camera 198 by entering a file name in the file name field 351. A browse button 352 also allows searches of the memory for different video files, which can either be buffered by selecting a buffer box 354 or loaded for pre-processing by selecting the load button 356.

If the loaded first and second image frames of the tear film are buffered, they can be played using display selection buttons 358, which will in turn display the images on the display 174. The images can be played on the display 174 in a looping fashion, if desired, by selecting the loop video selection box 360. A show subtracted video selection box 370 in the GUI utility 280 allows a clinician to show the resulting, subtracted video images of the tear film on the display 174 representative of the resulting signal comprised of the second output signal combined or subtracted from the first output signal, or vice versa. Also, by loading the first and second image frames, the previously described subtraction technique can be used to remove background image from the interference signal representing interference of the specularly reflected light from the tear film, as previously described above and illustrated in FIG. 12 as an example. The first image is subtracted from the second image to subtract or remove the background signal in the portions producing specularly reflected light in the second image, and vice versa, and then combined to produce an interference interaction of the specularly reflected light of the entire area or region of interest of the tear film, as previously illustrated in FIG. 12 (block 302 in FIG. 18). For example, this processing could be performed using the Matlab® function "cvAbsDiff."

The subtracted image containing the specularly reflected light from the tear film can also be overlaid on top of the original image capture of the tear film to display an image of the entire eye and the subtracted image in the display 174 by selecting the show overlaid original video selection box 362 in the GUI utility 280 of FIG. 19. An example of an overlaid original video to the subtracted image of specularly reflected light from the tear film is illustrated in the image 363 of FIG. 20. This overlay is provided so that flashing images of specularly reflected light from the tear film are not displayed, which may be unpleasant to visualize. An image, such as image 363 of the tear film illustrated in FIG. 20 may be obtained with a DBK 21AU04 Bayer VGA (640×480) video camera having a Pentax VS-LD25 Daitron 25-mm fixed focal length lens with maximum aperture at a working distance of 120 mm and having the following settings, as an example:

Gamma=100 (to provide linearity with exposure value)
Exposure=1/16 second
Frame rate=60 fps
Data Format=BY8
Video Format=—uncompressed, RGB 24-bit AVI
Hue=180 (neutral, no manipulation)
Saturation=128(neutral, no manipulation)
Brightness=0 (neutral, no manipulation)
Gain=260 (minimum available setting in this camera driver)
White balance=B=78; R=20.

Thresholding

Any number of optional pre-processing steps and functions can next be performed on the resulting combined tear film image(s), which will now be described. For example, an optional threshold pre-processing function may be applied to the resulting image or each image in a video of images of the tear film (e.g., FIG. 12) to eliminate pixels that have a subtraction difference signal below a threshold level (block 304 in FIG. 18). Image threshold provides a black and white mask (on/off) that is applied to the tear film image being processed to assist in removing residual information that may not be significant enough to be analyzed and/or may contribute to inaccuracies in analysis of the tear film. The threshold value used may be provided as part of a threshold value setting provided by a clinician as part of the pre-processing settings 264, as illustrated in the system diagram of FIG. 17A. For example, the GUI utility 280 in FIG. 19 includes a compute threshold selection box 372 that may be selected to perform thresholding, where the threshold brightness level can be selected via the threshold value slide 374. The combined tear film image of FIG. 12 is copied and converted to grayscale. The grayscale image has a threshold applied according to the threshold setting to obtain a binary (black/white) image that will be used to mask the combined tear film image of FIG. 12. After the mask is applied to the combined tear film image of FIG. 12, the new combined tear film image is stored in RAM 258. The areas of the tear film image that do not meet the threshold brightness level are converted to black as a result of the threshold mask.

Figure 21A:
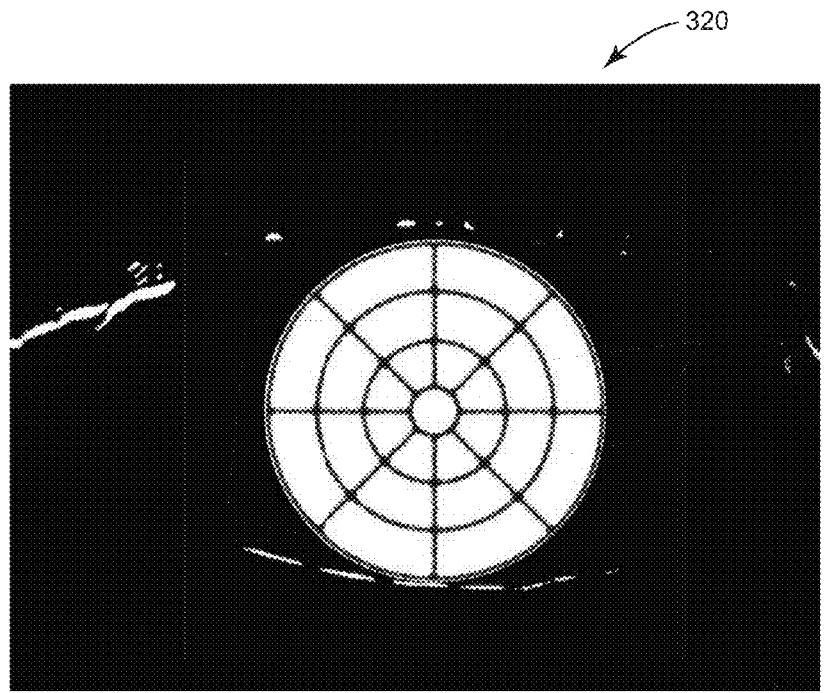
FIGS. 21A and 21B illustrate exemplary threshold masks that may be used to provide a threshold function during pre-processing of a resulting image containing specularly reflected light from a patient's tear film.
Figure 21B:
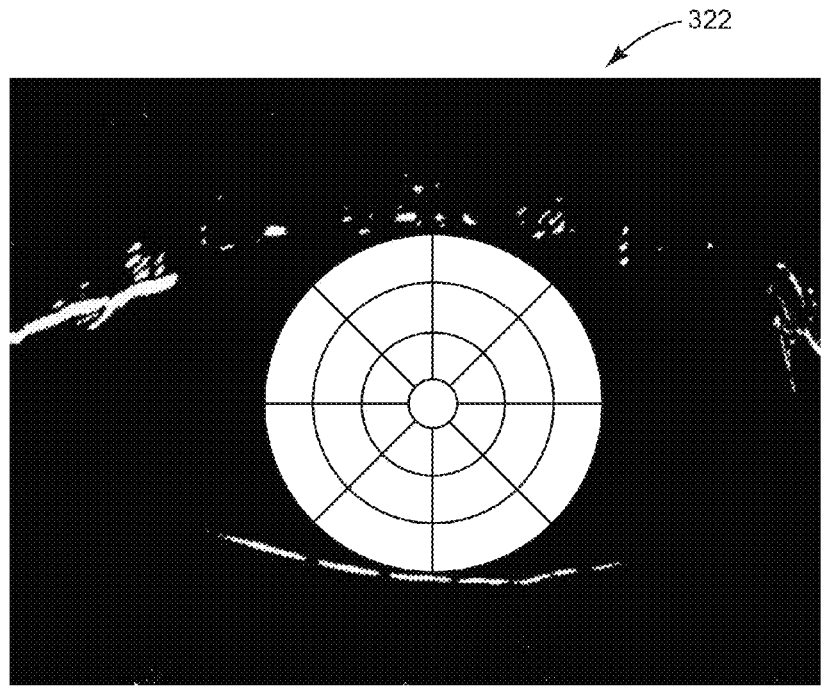
Figure 22:
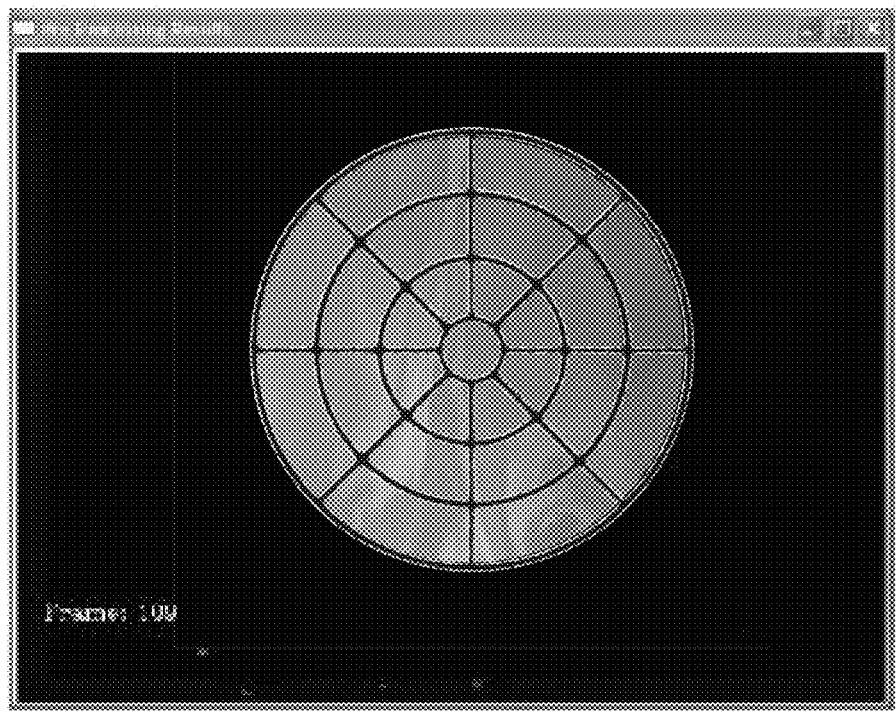
FIG. 22 illustrates an exemplary image of FIG. 20 after a threshold pre-processing function has been performed leaving interference of the specularly reflected light from the patient's tear film.

FIGS. 21A and 21B illustrate examples of threshold masks for the combined tear film provided in FIG. 12. FIG. 21A illustrates a threshold mask 320 for a threshold setting of 70 counts out of a full scale level of 255 counts. FIG. 21B illustrates a threshold mask 322 for a threshold setting of 50. Note that the threshold mask 320 in FIG. 21A contains less portions of the combined tear film image, because the threshold setting is higher than for the threshold mask 322 of FIG. 21B. When the threshold mask according to a threshold setting of 70 is applied to the exemplary combined tear film image of FIG. 12, the resulting tear film image is illustrated FIG. 22. Much of the residual subtracted background image that surrounds the area or region of interest has been masked away.

Erode and Dilate

Figure 23:
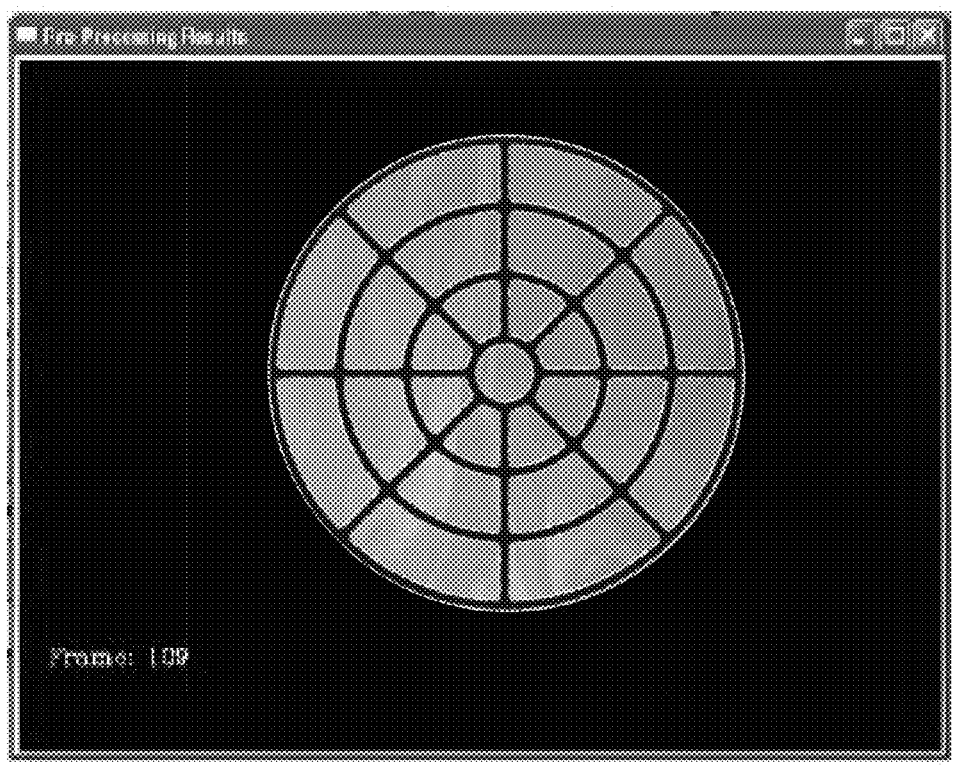
FIG. 23 illustrates an exemplary image of the FIG. 22 image after erode and dilate pre-processing functions have been performed on the image.

Another optional pre-processing function that may be applied to the resulting image or each image in a video of images of the tear film to correct anomalies in the combined tear film image(s) is the erode and dilate functions (block 306 in FIG. 18). The erode function generally removes small anomaly artifacts by subtracting objects with a radius smaller than an erode setting (which is typically in number of pixels) removing perimeter pixels where interference information may not be as distinct or accurate. The erode function may be selected by a clinician in the GUI utility 280 (see FIG. 19) by selecting the erode selection box 376. If selected, the number of pixels for erode can be provided in an erode pixels text box 378. Dilating generally connects areas that are separated by spaces smaller than a minimum dilate size setting by adding pixels of the eroded pixel data values to the perimeter of each image object remaining after the erode function is applied. The dilate function may be selected by a clinician in the GUI utility 280 (see FIG. 19) by providing the number of pixels for dilating in a dilate pixels text box 380. Erode and dilate can be used to remove small region anomalies in the resulting tear film image prior to analyzing the interference interactions to reduce or avoid inaccuracies. The inaccuracies may include those caused by bad pixels of the video camera 198 or from dust that may get onto a scanned image, or more commonly, spurious specular reflections such as: tear film meniscus at the juncture of the eyelids, glossy eyelash glints, wet skin tissue, etc. FIG. 23 illustrates the resulting tear film image of FIG. 22 after erode and dilate functions have been applied and the resulting tear film image is stored in RAM 258. As illustrated therein, pixels previously included in the tear film image that were not in the tear film area or region of interest are removed. This prevents data in the image outside the area or region of interest from affecting the analysis of the resulting tear film image(s).

Removing Blinks/Other Anomalies

Another optional pre-processing function that may be applied to the resulting image or each image in a video of images of the tear film to correct anomalies in the resulting tear film image is to remove frames from the resulting tear film image that include patient blinks or significant eye movements (block 308 in FIG. 18). As illustrated in FIG. 18, blink detection is shown as being performed after a threshold and erode and dilate functions are performed on the tear film image or video of images. Alternatively, the blink detection could be performed immediately after background subtraction, such that if a blink is detected in a given frame or frames, the image in such frame or frames can be discarded and not pre-processed. Not pre-processing images where blinks are detected may increase the overall speed of pre-processing. The remove blinks or movement pre-processing may be selectable. For example, the GUI utility 280 in FIG. 19 includes a remove blinks selection box 384 to allow a user to control whether blinks and/or eye movements are removed from a resulting image or frames of the patient's tear film prior to analysis. Blinking of the eyelids covers the ocular tear film, and thus does not produce interference signals representing specularly reflected light from the tear film. If frames containing whole or partial blinks obscuring the area or region of interest in the patient's tear film are not removed, it would introduce errors in the analysis of the interference signals to determine characteristics of the TFLT of the patient's ocular tear film. Further, frames or data with significant eye movement between sequential images or frames can be removed during the detect blink pre-processing function. Large eye movements could cause inaccuracy in analysis of a patient's tear film when employing subtraction techniques to remove background signal, because subtraction involves subtracting frame-pairs in an image that closely match spatially. Thus, if there is significant eye movement between first and second images that are to be subtracted, frame pairs may not be closely matched spatially thus inaccurately removing background signal, and possibly removing a portion of the interference image of specularly reflected light from the tear film.

Different techniques can be used to determine blinks in an ocular tear film image and remove the frames as a result. For example, in one embodiment, the control system 240 directs the pre-processing system 260 to review the stored frames of the resulting images of the tear film to monitor for the presence of an eye pupil using pattern recognition. A Hough Circle Transform may be used to detect the presence of the eye pupil in a given image or frame. If the eye pupil is not detected, it is assembled such that the image or frame contains an eye blink and thus should be removed or ignored during pre-processing from the resulting image or video of images of the tear film. The resulting image or video of images can be stored in RAM 258 for subsequent processing and/or analyzation.

Figure 24:
FIG. 24 illustrates an exemplary histogram used to detect eye blinks and/or eye movements in captured images or frames of a tear film.

In another embodiment, blinks and significant eye movements are detected using a histogram sum of the intensity of pixels in a resulting subtracted image or frame of a first and second image of the tear film. An example of such a histogram 329 is illustrated in FIG. 24. The resulting or subtracted image can be converted to grayscale (i.e., 255 levels) and a histogram generated with the gray levels of the pixels. In the histogram 329 of FIG. 24, the x-axis contains gray level ranges, and the number of pixels falling within each gray level is contained in the y-axis. The total of all the histogram 329 bins are summed. In the case of two identical frames that are subtracted, the histogram sum would be zero. However, even without an eye blink or significant eye movement, two sequentially captured frames of the patient's eye and the interference signals representing the specularly reflected light from the tear film are not identical. However, frame pairs with little movement will have a low histogram sum, while frame pairs with greater movement will yield a larger histogram sum. If the histogram sum is beyond a pre-determined threshold, an eye blink or large eye movement can be assumed and the image or frame removed. For example, the GUI utility 280 illustrated in FIG. 19 includes a histogram sum slide bar 386 that allows a user to set the threshold histogram sum. The threshold histogram sum for determining whether a blink or large eye movement should be assumed and thus the image removes from analysis of the patient's tear film can be determined experimentally, or adaptively over the course of a frame playback, assuming that blinks occur at regular intervals.

An advantage of a histogram sum of intensity method to detect eye blinks or significant eye movements is that the calculations are highly optimized as opposed to pixel-by-pixel analysis, thus assisting with real-time processing capability. Further, there is no need to understand the image structure of the patient's eye, such as the pupil or the iris details. Further, the method can detect both blinks and eye movements.

Another alternate technique to detect blinks in the tear film image or video of images for possible removal is to calculate a simple average gray level in an image or video of images. Because the subtracted, resulting images of the tear film subtract background signal, and have been processed using a threshold mask, and erode and dilate functions performed in this example, the resulting images will have a lower average gray level due to black areas present than if a blink is present. A blink contains skin color, which will increase the average gray level of an image containing a blink. A threshold average gray level setting can be provided. If the average gray level of a particular frame is below the threshold, the frame is ignored from further analysis or removed from the resulting video of frames of the tear film.

Another alternate technique to detect blinks in an image or video of images for removal is to calculate the average number of pixels in a given frame that have a gray level value below a threshold gray level value. If the percentage of pixels in a given frame is below a defined threshold percentage, this can be an indication that a blink has occurred in the frame, or that the frame is otherwise unworthy of consideration when analyzing the tear film. Alternatively, a spatial frequency calculation can be performed on a frame to determine the amount of fine detail in a given frame. If the detail present is below a threshold detail level, this may be an indication of a blink or other obscurity of the tear film, since skin from the eyelid coming down and being captured in a frame will have less detail than the subtracted image of the tear film. A histogram can be used to record any of the above-referenced calculations to use in analyzing whether a given frame should be removed from the final pre-processed resulting image or images of the tear film for analyzation.

ICC Profiling

Figure 25:
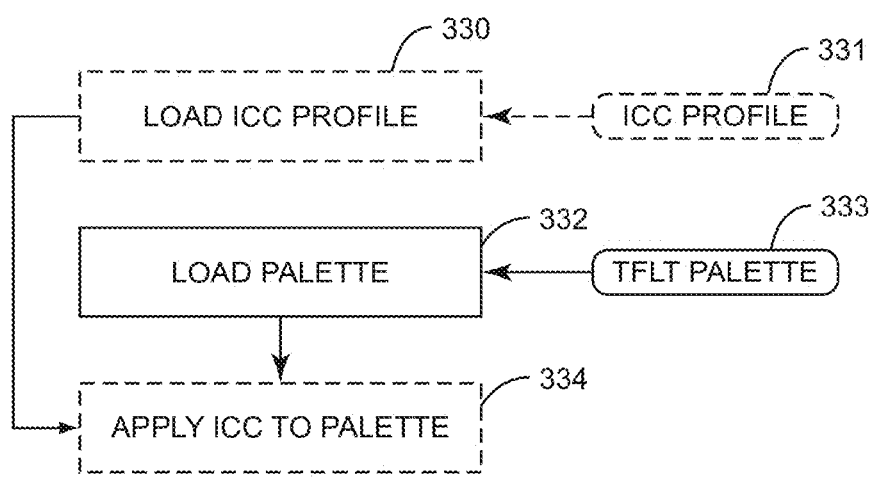
FIG. 25 illustrates an exemplary process for loading an International Colour Consortium (ICC) profile and tear film interference model into the OSI device of FIG. 9-11.

Pre-processing of the resulting tear film image(s) may also optionally include applying an International Colour Consortium (ICC) profile to the pre-processed interference images of the tear film (block 310, FIG. 18). FIG. 25 illustrates an optional process of loading an ICC profile into an ICC profile 331 in the control system 240 (block 330). In this regard, the GUI utility 280 illustrated in FIG. 19 also includes an apply ICC box 392 that can be selected by a clinician to load the ICC profile 331. The ICC profile 331 may be stored in memory in the control system 240, including in RAM 258. In this manner, the GUI utility 280 in FIG. 19 also allows for a particular ICC profile 331 to be selected for application in the ICC profile file text box 394. The ICC profile 331 can be used to adjust color reproduction from scanned images from cameras or other devices into a standard red-green-blue (RGB) color space (among other selectable standard color spaces) defined by the ICC and based on a measurement system defined internationally by the Commission Internationale de l'Eclairage (CIE). Adjusting the pre-processed resulting tear film interference images corrects for variations in the camera color response and the light source spectrum and allows the images to be compatibly compared with a tear film layer interference model to measure the thickness of a TFLT, as will be described later in this application. The tear film layers represented in the tear film layer interference model can be LLTs, ALTs, or both, as will be described in more detail below.

In this regard, the ICC profile 331 may have been previously loaded to the OSI device 170 before imaging of a patient's tear film and also applied to a tear film layer interference model when loaded into the OSI device 170 independent of imaging operations and flow. As will be discussed in more detail below, a tear film layer interference model in the form of a TFLT palette 333 containing color values representing interference interactions from specularly reflected light from a tear film for various LLTs and ALTs can also be loaded into the OSI device 170 (block 332 in FIG. 25). The TFLT palette 333 contains a series of color values that are assigned LLTs and/or ALTs based on a theoretical tear film layer interference model to be compared against the color value representations of interference interactions in the resulting image(s) of the patient's tear film. When applying the optional ICC profile 331 to the TFLT palette 333 (block 334 in FIG. 25), the color values in both the tear film layer interference model and the color values representing interference interactions in the resulting image of the tear film are adjusted for a more accurate comparison between the two to measure LLT and/or ALT.

Brightness

Also as an optional pre-processing step, brightness and red-green-blue (RGB) subtract functions may be applied to the resulting interference signals of the patient's tear film before post-processing for analysis and measuring TFLT is performed (blocks 312 and 314 respectively in FIG. 18). The brightness may be adjusted pixel-by-pixel by selecting the adjust brightness selection box 404 according to a corresponding brightness level value provided in a brightness value box 406, as illustrated in the GUI utility 280 of FIG. 19. When the brightness value box 406 is selected, the brightness of each palette value of the TFLT palette 333 is also adjusted accordingly.

RGB Subtraction (Normalization)

The RGB subtract function subtracts a DC offset from the interference signal in the resulting image(s) of the tear film representing the interference interactions in the interference signal. An RGB subtract setting may be provided from the pre-processing settings 264 to apply to the interference signal in the resulting image of the tear film to normalize against. As an example, the GUI utility 280 in FIG. 19 allows an RGB offset to be supplied by a clinician or other technician for use in the RGB subtract function. As illustrated therein, the subtract RGB function can be activated by selecting the RGB subtract selection box 396. If selected, the individual RGB offsets can be provided in offset value input boxes 398. After pre-processing is performed, if any, on the resulting image, the resulting image can be provided to a post-processing system 262 to measure TLFT (block 316), as discussed later below in this application.

Displaying Images

The resulting images of the tear film may also be displayed on the display 174 of the OSI device 170 for human diagnosis of the patient's ocular tear film. The OSI device 170 is configured so that a clinician can display and see the raw captured image of the patient's 184 eye 192 by the video camera 198, the resulting images of the tear film before pre-processing, or the resulting images of the tear film after pre-processing. Displaying images of the tear film on the display 174 may entail different settings and steps. For example, if the video camera 198 provides linear images of the patient's tear film, the linear images must be converted into a non-linear format to be properly displayed on the display 174. In this regard, a process that is performed by the visualization system 270 according to one embodiment is illustrated in FIG. 26.

Figure 26:
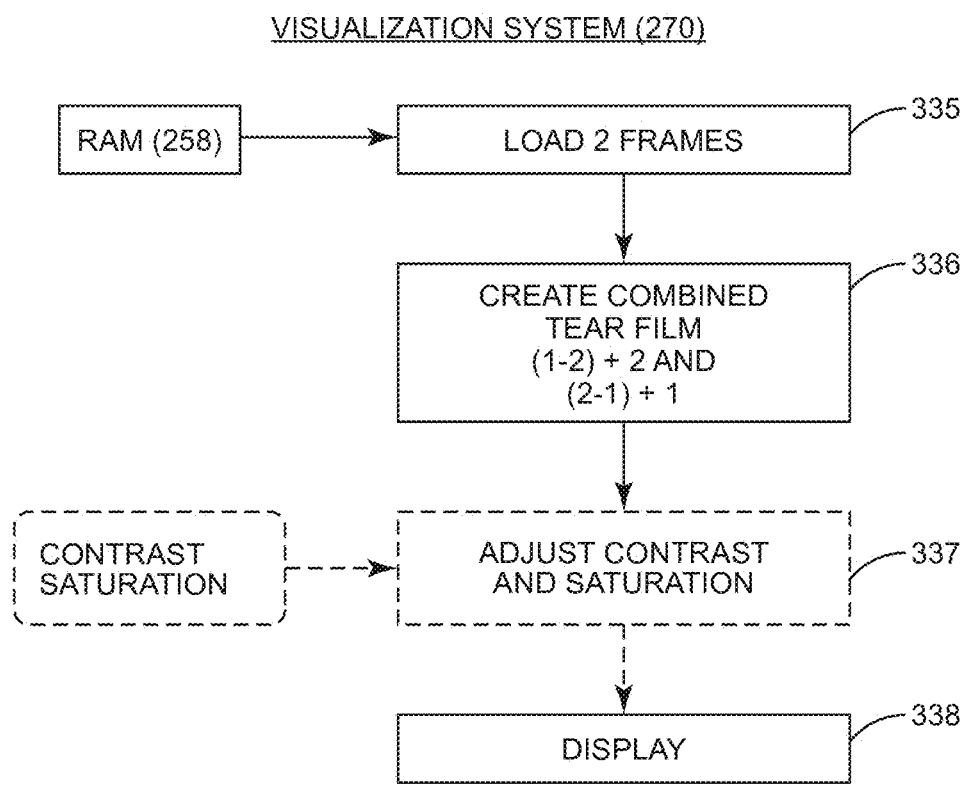
FIG. 26 illustrates a flowchart providing an exemplary visualization system process for displaying images of a patient's tear film on a display in the OSI device of FIG. 9-11.

As illustrated in FIG. 26, the video camera 198 has already taken the first and second tiled images of a patient's ocular tear film as previously illustrated in FIGS. 11A and 11B, and provided the images to the video acquisition system 256. The frames of the first and second images were then loaded into RAM 258 by the video acquisition system 256. Thereafter, as illustrated in FIG. 26, the control system 240 commands the visualization system 270 to process the first and second images to prepare them for being displayed on the display 174. In this regard, the visualization system 270 loads the first and second image frames of the ocular tear film from RAM 258 (block 335). The previously described subtraction technique is used to remove background signal from the interference interactions of the specularly reflected light from the tear film, as previously described above and illustrated in FIG. 12. The first image(s) is subtracted from the second image(s) to remove background signal in the illuminated portions of the first image(s), and vice versa, and the subtracted images are then combined to produce an interference interaction of the specularly reflected light of the entire area or region of interest of the tear film, as previously discussed and illustrated in FIG. 12 (block 336 in FIG. 26).

Again, for example, this processing could be performed using the Matlab® function "cvAbsDiff." Before being displayed, the contrast and saturation levels for the resulting images can be adjusted according to contrast and saturation settings provided by a clinician via the user interface system 278 and/or programmed into the visualization system 270 (block 337). For example, the GUI utility 280 in FIG. 19 provides an apply contrast button 364 and a contrast setting slide 366 to allow the clinician to set the contrast setting in the display settings 274 for display of images on the display 174. The GUI utility 280 also provides an apply saturation button 368 and a saturation setting slide 369 to allow a clinician to set the saturation setting in the display settings 274 for the display of images on the display 174. The images can then be provided by the visualization system 270 to the display 174 for viewing (block 338 in FIG. 26). Also, any of the resulting images after pre-processing steps in the pre-processing system 260 can be provided to the display 174 for processing.

Figure 27A:
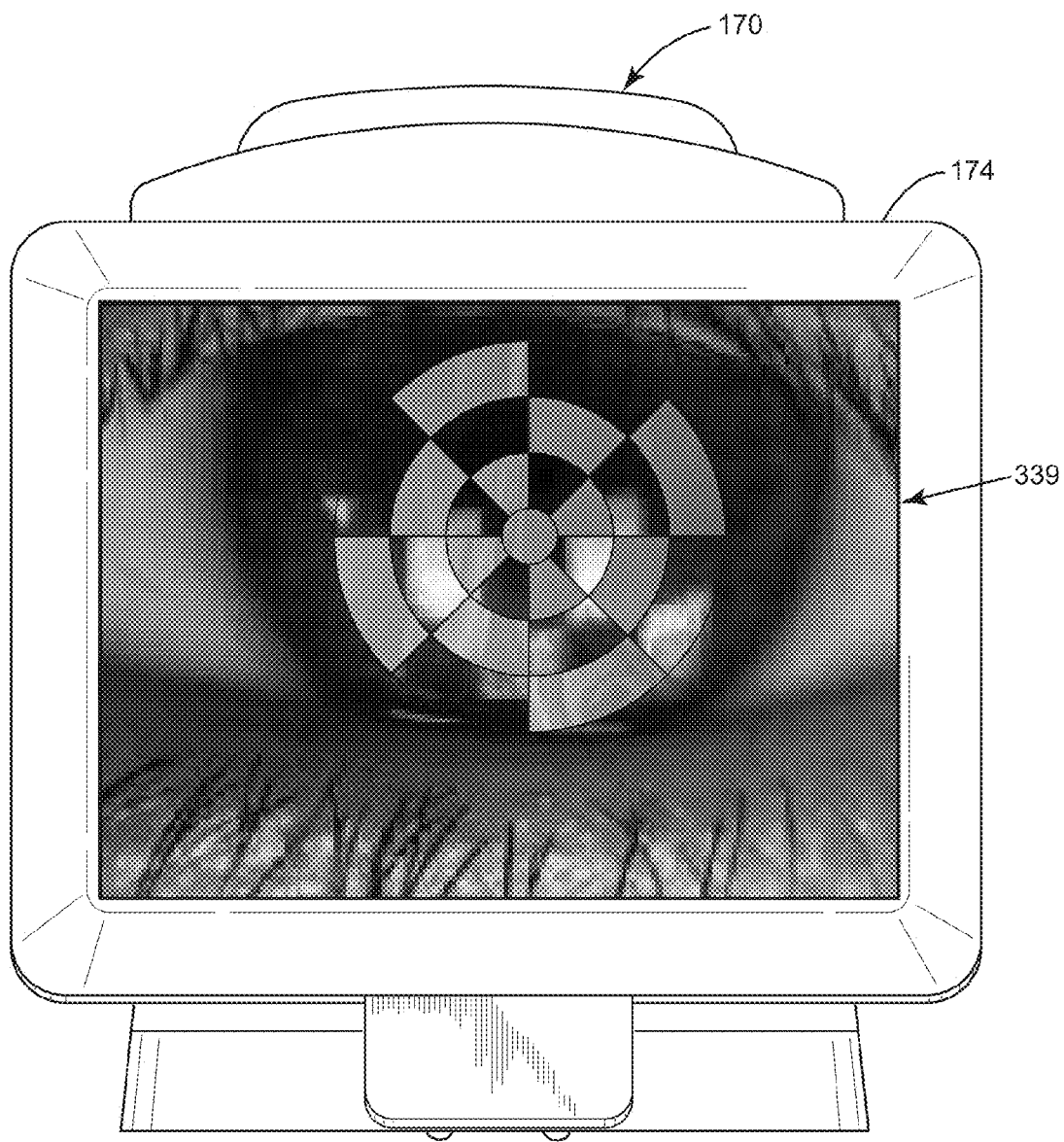
FIGS. 27A-27C illustrate exemplary images of a patient's tear film with a tiled pattern of interference interactions from specularly reflected light from the tear film displayed on a display.
Figure 27B:
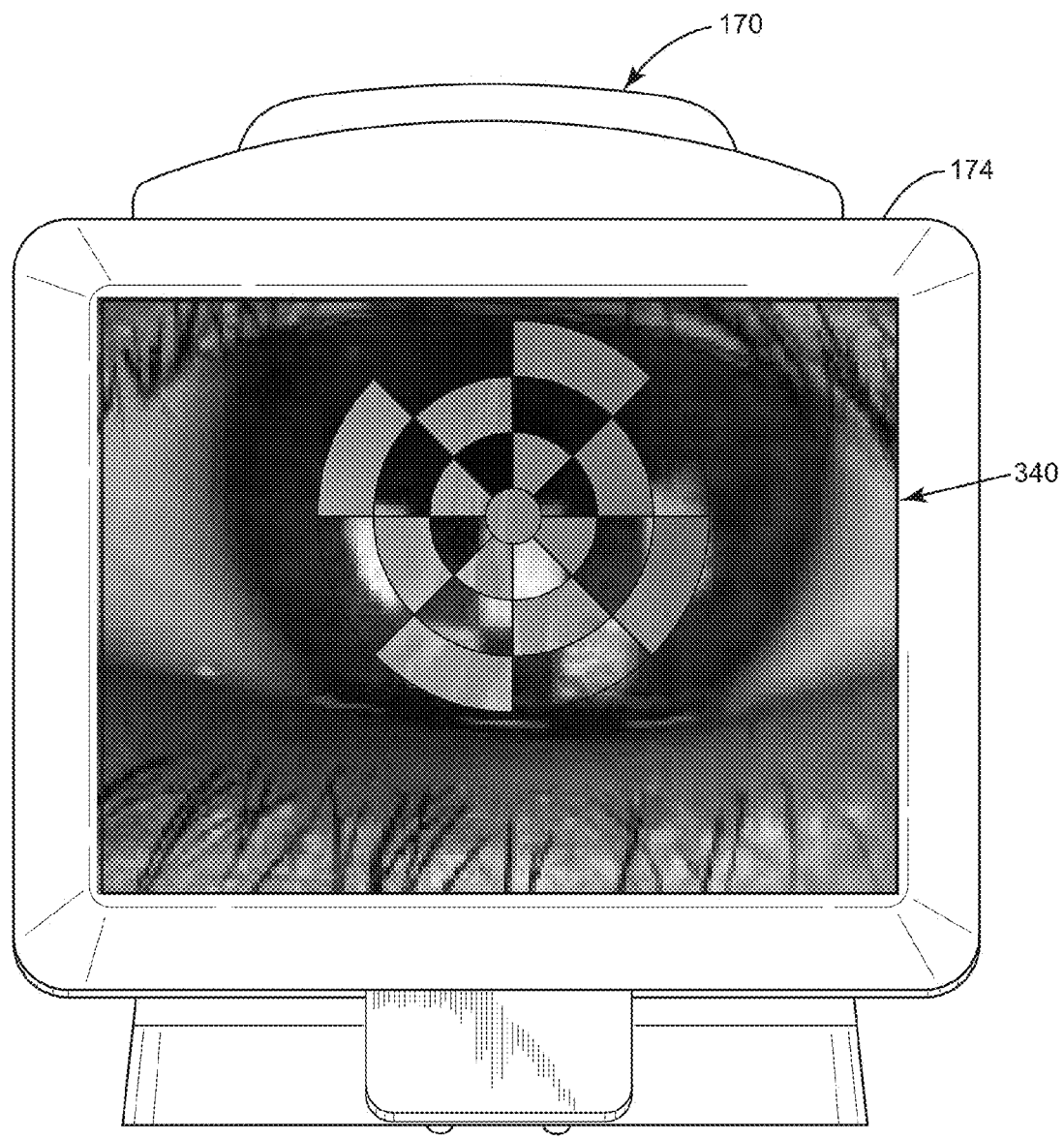
Figure 27C:
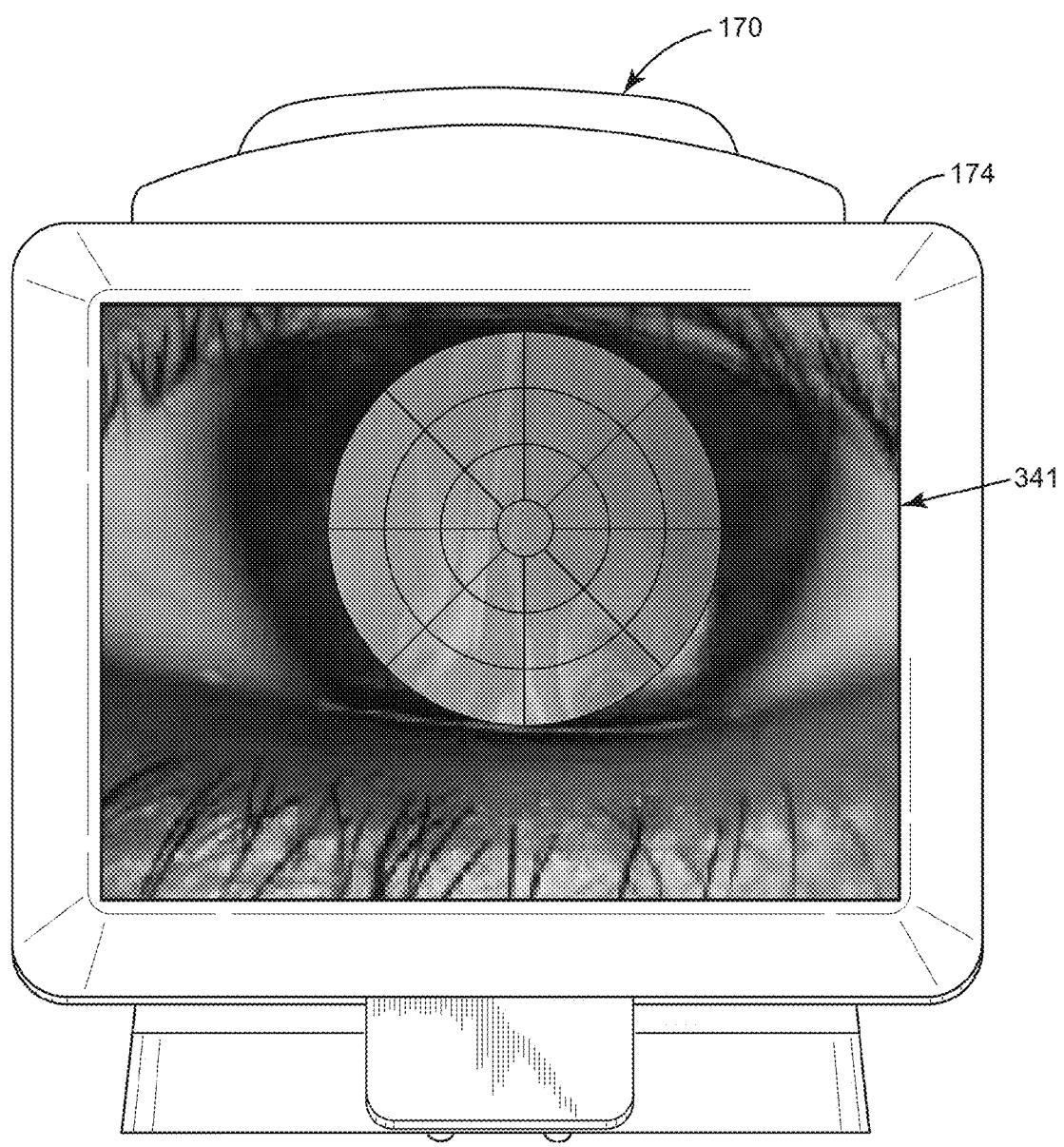

FIGS. 27A-27C illustrate examples of different tear film images that are displayed on the display 174 of the OSI device 170. FIG. 27A illustrates a first image 339 of the patient's tear film showing the tiled pattern captured by the video camera 198. This image is the same image as illustrated in FIG. 11A and previously described above, but processed from a linear output from the video camera 198 to be properly displayed on the display 174. FIG. 27B illustrates a second image 340 of the patient's tear film illustrated in FIG. 11B and previously described above. FIG. 27C illustrates a resulting "overlaid" image 341 of the first and second images 339, 340 of the patient's tear film and to provide interference interactions of the specularly reflected light from the tear film over the entire area or region of interest. This is the same image as illustrated in FIG. 7C and previously described above.

In this example, the original number of frames of the patient's tear film captured can be reduced by half due to the combination of the first and second tiled pattern image(s). Further, if frames in the subtracted image frames capture blinks or erratic movements, and these frames are eliminated in pre-processing, a further reduction in frames will occur during pre-processing from the number of images raw captured in images of the patient's tear film. Although these frames are eliminated from being further processed, they can be retained for visualization, rendering a realistic and natural video playback. Further, by applying a thresholding function and erode and dilating functions, the number of non-black pixels which contain TLFT interference information is substantially reduced as well. Thus, the amount of pixel information that is processed by the post-processing system 262 is reduced, and may be on the order of 70 percent (%) less information to process than the raw image capture information, thereby pre-filtering for the desired interference ROI and reducing or eliminating potentially erroneous information as well as allowing for faster analysis due to the reduction in information.

At this point, the resulting images of the tear film have been pre-processed by the pre-processing system 260 according to whatever pre-processing settings 264 and pre-processing steps have been selected or implemented by the control system 240. The resulting images of the tear film are ready to be processed for analyzing and determining TFLT. In this example, this is performed by the post-processing system 262 in FIG. 17A and is based on the post-processing settings 266 also illustrated therein. An embodiment of the post-processing performed by the post-processing system 262 is illustrated in the flowchart of FIG. 28.

Tear Film Interference Models

Figure 28:
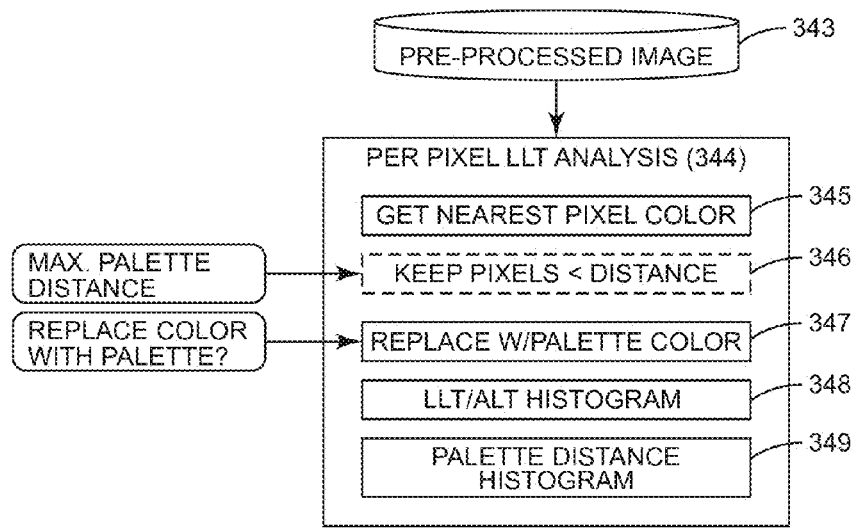
FIG. 28 illustrates an exemplary post-processing system that may be provided in the OSI device of FIG. 9.

As illustrated in FIG. 28, pre-processed images 343 of the resulting images of the tear film are retrieved from RAM 258 where they were previously stored by the pre-processing system 260. Before discussing the particular embodiment of the post-processing system 262 in FIG. 28, in general, to measure TFLT, the RGB color values of the pixels in the resulting images of the tear film are compared against color values stored in a tear film interference model that has been previously loaded into the OSI device 170 (see FIG. 25). The tear film interference model may be stored as a TFLT palette 333 containing RGB values representing interference colors for given LLTs and/or ALTs. The TFLT palette contains interference color values that represent TFLTs based on a theoretical tear film interference model in this embodiment. Depending on the TFLT palette 333 provided, the interference color values represented therein may represent LLTs, ALTs, or both. An estimation of TFLT for each ROI pixel is based on this comparison. This estimate of TFLT is then provided to the clinician via the display 174 and/or recorded in memory to assist in diagnosing DES.

Before discussing embodiments of how the TFLTs are estimated from the pre-processed resulting image colored interference interactions resulting from specularly reflected light from the tear film, tear film interference modeling is first discussed. Tear film interference modeling can be used to determine an interference color value for a given TFLT to measure TFLT, which can include both LLT and/or ALT.

Although the interference signals representing specularly reflected light from the tear film are influenced by all layers in the tear film, the analysis of interference interactions due to the specularly reflected light can be analyzed under a 2-wave tear film model (i.e., two reflections) to measure LLT. A 2-wave tear film model is based on a first light wave(s) specularly reflecting from the air-to-lipid layer transition of a tear film and a second light wave specularly reflecting from the lipid layer-to-aqueous layer transition of the tear film. In the 2-wave model, the aqueous layer is effective ignored and treated to be of infinite thickness. To measure LLT using a 2-wave model, a 2-wave tear film model was developed wherein the light source and lipid layers of varying thicknesses were modeled mathematically. To model the tear-film interference portion, commercially available software, such as that available by FilmStar and Zemax as examples, allows image simulation of thin films for modeling. Relevant effects that can be considered in the simulation include refraction, reflection, phase difference, polarization, angle of incidence, and refractive index wavelength dispersion. For example, a lipid layer could be modeled as having an index of refraction of 1.48 or as a fused silica substrate ($SiO_2$) having a 1.46 index of refraction. A back material, such as Magnesium Flouride ($MgF_2$) having an index of refraction of 1.38, may be used to provide a 2-wave model of air/$SiO_2$/$MgF_2$ (1.0/1.46/1.38). To obtain the most accurate modeling results, the model can include the refractive index and wavelength dispersion values of biological lipid material and biological aqueous material, found from the literature, thus to provide a precise two-wave model of air/lipid/aqueous layers. Thus, a 2-wave tear film interference model allows measurement of LLT regardless of ALT.

Simulations can be mathematically performed by varying the LLT between 10 to 300 nm. As a second step, the RGB color values of the resulting interference signals from the modeled light source causing the modeled lipid layer to specularly reflect light and be received by the modeled camera were determined for each of the modeled LLT. These RGB color values representing interference interactions in specularly reflected light from the modeled tear film were used to form a 2-wave model LLT palette, wherein each RGB color value is assigned a different LLT. The resulting subtracted image of the first and second images from the patient's tear film containing interference signals representing specularly reflected light are compared to the RGB color values in the 2-wave model LLT palette to measure LLT.

In another embodiment, a 3-wave tear film interference model may be employed to estimate LLT. A 3-wave tear film interference model does not assume that the aqueous layer is infinite in thickness. In an actual patient's tear film, the aqueous layer is not infinite. The 3-wave tear film interference model is based on both the first and second reflected light waves of the 2-wave model and additionally light wave(s) specularly reflecting from the aqueous-to-mucin layer and/or cornea transitions. Thus, a 3-wave tear film interference model recognizes the contribution of specularly reflected light from the aqueous-to-mucin layer and/or cornea transition that the 2-wave tear film interference model does not. To estimate LLT using a 3-wave tear film interference model, a 3-wave tear film model was previously constructed wherein the light source and a tear film of varying lipid and aqueous layer thicknesses were mathematically modeled. For example, a lipid layer could be mathematically modeled as a material having an index of refraction of 1.48 or as fused silica substrate ($SiO_2$), which has a 1.46 index of refraction. Different thicknesses of the lipid layer can be simulated. A fixed thickness aqueous layer (e.g., $>=2$ μm) could be mathematically modeled as Magnesium Flouride ($MgF_2$) having an index of refraction of 1.38. A biological cornea could be mathematically modeled as fused silica with no dispersion, thereby resulting in a 3-wave model of air/$SiO_2$/$MgF_2$/$SiO_2$ (i.e., 1.0/1.46/1.38/1.46 with no dispersion). As before, accurate results are obtained if the model can include the refractive index and wavelength dispersion values of biological lipid material, biological aqueous material, and cornea tissue, found from the literature, thus to provide a precise two-wave model of air/lipid/aqueous/cornea layers. The resulting interference interactions of specularly reflected light from the various LLT values and with a fixed ALT value are recorded in the model and, when combined with modeling of the light source and the camera, will be used to compare against interference from specularly reflected light from an actual tear film to measure LLT and/or ALT.

In another embodiment of the OSI device 170 and the post-processing system 262 in particular, a 3-wave tear film interference model is employed to estimate both LLT and ALT. In this regard, instead of providing either a 2-wave theoretical tear film interference model that assumes an infinite aqueous layer thickness or a 3-wave model that assumes a fixed or minimum aqueous layer thickness (e.g., ≥2 μm), a 3-wave theoretical tear film interference model is developed that provides variances in both LLT and ALT in the mathematical model of the tear film. Again, the lipid layer in the tear film model could be modeled mathematically as a material having an index of refraction of 1.48 or as fused silica substrate ($SiO_2$) having a 1.46 index of refraction. The aqueous layer could be modeled mathematically as Magnesium Flouride ($MgF_2$) having an index of refraction of 1.38. A biological cornea could be modeled as fused silica with no dispersion, thereby resulting in a 3-wave model of air/$SiO_2$/$MgF_2$/$SiO_2$ (no dispersion). Once again, the most accurate results are obtained if the model can include the refractive index and wavelength dispersion values of biological lipid material, biological aqueous material, and cornea tissue, found from the literature, thus to provide a precise two-wave model of air/lipid/aqueous/cornea layers. Thus, a two-dimensional (2D) TFLT palette 430 (FIG. 29A) is produced for analysis of interference interactions from specularly reflected light from the tear film. One dimension of the TFLT palette 430 represents a range of RGB color values each representing a given theoretical LLT calculated by mathematically modeling the light source and the camera and calculating the interference interactions from specularly reflected light from the tear film model for each variation in LLT 434 in the tear film interference model. A second dimension of the TFLT palette 430 represents ALT also calculated by mathematically modeling the light source and the camera and calculating the interference interactions from specularly reflected light from the tear film interference model for each variation in ALT 432 at each LLT value 434 in the tear film interference model.

Post-Processing/TFLT Measurement

Figure 29A:
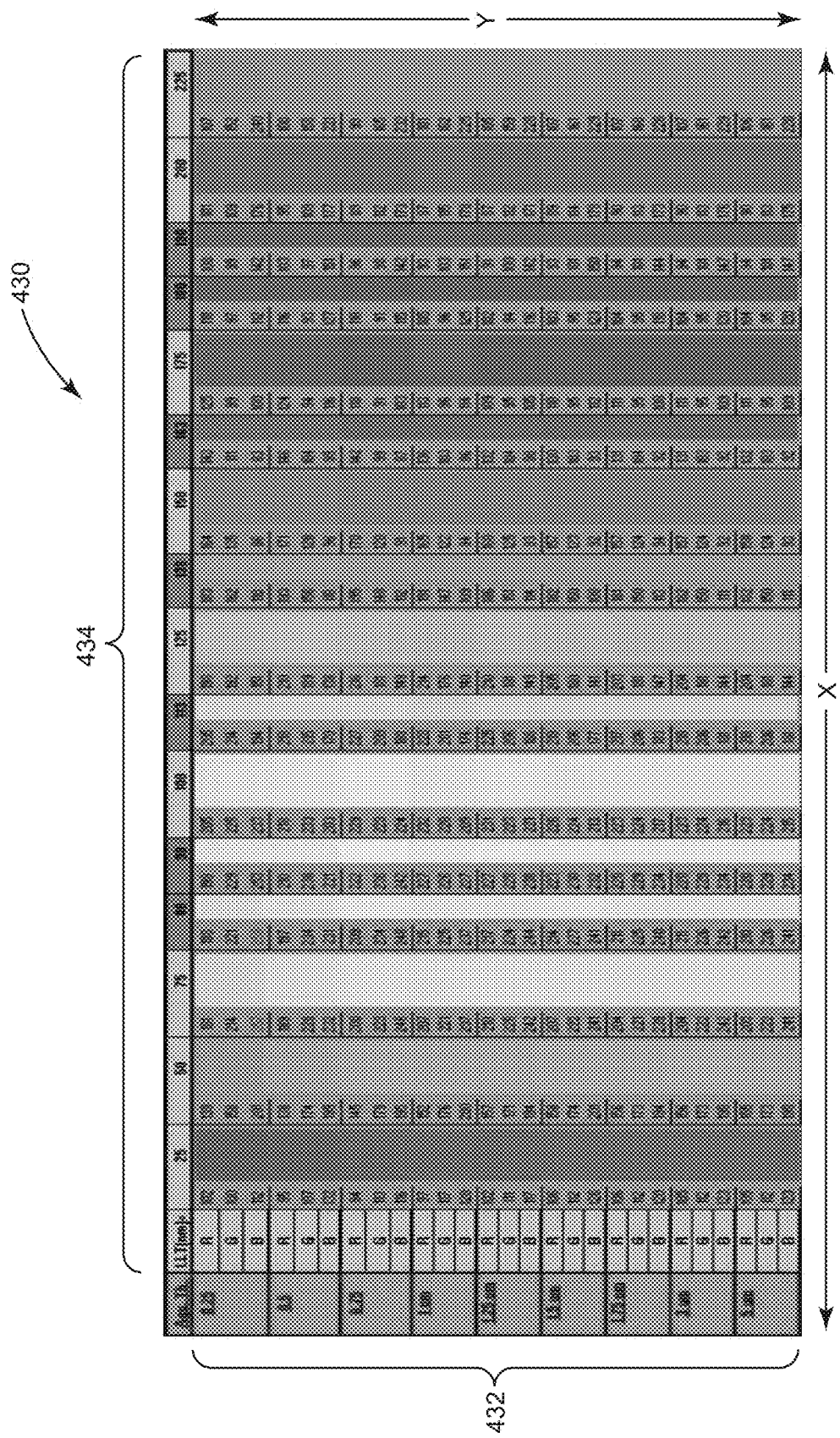
FIG. 29A illustrates an exemplary 3-wave tear film interference model based on a 3-wave theoretical tear film model to correlate different observed interference colors with different lipid layer thicknesses (LLTs) and aqueous layer thicknesses (ALTs)
Figure 29B:
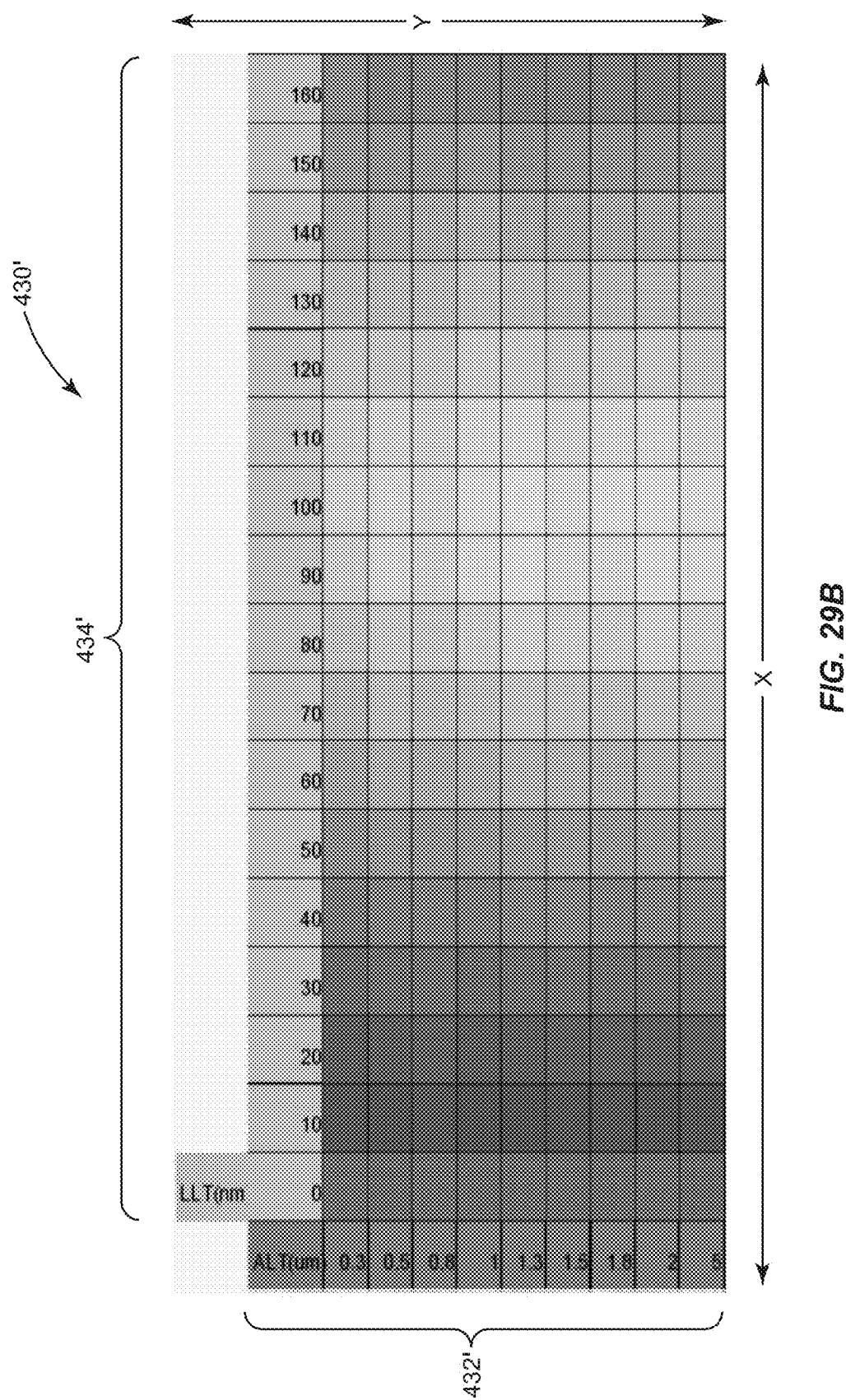
FIG. 29B illustrates another exemplary 3-wave tear film interference model based on a 3-wave theoretical tear film model to correlate different observed interference colors with different lipid layer thicknesses (LLTs) and aqueous layer thicknesses (ALTs)

To measure TFLT, a spectral analysis of the resulting interference signal or image is performed during post-processing. In one embodiment, the spectral analysis is performed by performing a look-up in a tear film interference model to compare one or more interference interactions present in the resulting interference signal representing specularly reflected light from the tear film to the RGB color values in the tear film interference model. In this regard, FIGS. 29A and 29B illustrate two examples of palette models for use in post-processing of the resulting image having interference interactions from specularly reflected light from the tear film using a 3-wave theoretical tear film interference model developed using a 3-wave theoretical tear film model. In general, an RGB numerical value color scheme is employed in this embodiment, wherein the RGB value of a given pixel from a resulting pre-processed tear film image of a patient is compared to RGB values in the 3-wave tear film interference model representing color values for various LLTs and ALTs in a 3-wave modeled theoretical tear film. The closest matching RGB color is used to determine the LLT and/or ALT for each pixel in the resulting signal or image. All pixels for a given resulting frame containing the resulting interference signal are analyzed in the same manner on a pixel-by-pixel basis. A histogram of the LLT and ALT occurrences is then developed for all pixels for all frames and the average LLT and ALT determined from the histogram (block 348 in FIG. 28).

FIG. 29A illustrates an exemplary TFLT palette 430 in the form of colors representing the included RGB color values representing interference of specularly reflected light from a 3-wave theoretical tear film model used to compared colors from the resulting image of the patient's tear film to estimate LLT and ALT. FIG. 29B illustrates an alternative example of a TFLT palette 430' in the form of colors representing the included RGB color values representing interference of specularly reflected light from a 3-wave theoretical tear film model used to compare colors from the resulting image of the patient's tear film to estimate LLT and ALT. As illustrated in FIG. 29A, the TFLT palette 430 contains a plurality of hue colors arranged in a series of rows for ALT 432 and columns for LLT 434. In this example, there are 144 color hue entries in the palette 430, with nine (9) different ALTs and sixteen (16) different LLTs in the illustrated TFLT palette 430, although another embodiment includes thirty (30) different LLTs. Providing any number of LLT and TFLT increments is theoretically possible. The columns for LLT 434 in the TFLT palette 430 contain a series of LLTs in ascending order of thickness from left to right. The rows for ALT 432 in the TFLT palette 430 contain a series of ALTs in ascending order of thickness from top to bottom. The sixteen (16) LLT increments provided in the columns for LLT 434 in the TFLT palette 430 are 25, 50, 75, 80, 90, 100, 113, 125, 138, 150, 163, 175, 180, 190, 200, and 225 nanometers (nm). The nine (9) ALT increments provided in the rows for ALT 432 in the TFLT palette 430 are 0.25, 0.5, 0.75, 1.0, 1.25, 1.5, 1.75, 3.0 and 6.0 μm. As another example, as illustrated in FIG. 29B, the LLTs in the columns for LLT 434' in the TFLT palette 430' are provided in increments of 10 nm between 0 nm and 160 nm. The nine (9) ALT increments provided in the rows for ALT 432' in the TFLT palette 430 are 0.3, 0.5, 0.08, 1.0, 1.3, 1.5, 1.8, 2.0 and 5.0 μm.

Figure 30:
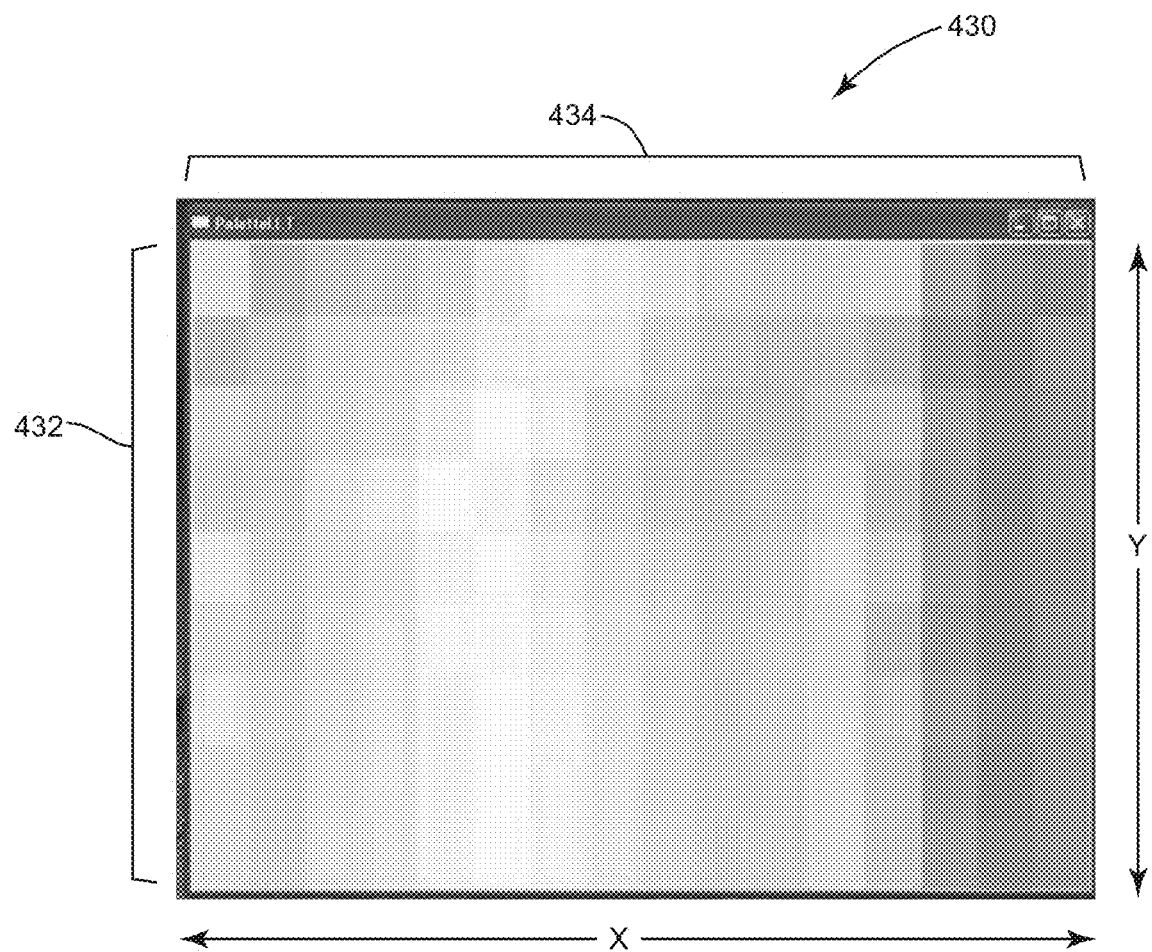
FIG. 30 is another representation of the 3-wave tear film interference model of FIGS. 29A and 29B with normalization applied to each red-green-blue (RGB) color value individually.

As part of a per pixel LLT analysis 344 provided in the post-processing system 262 in FIG. 28, for each pixel in each of the pre-processed resulting images of the area or region of interest in the tear film, a closest match determination is made between the RGB color of the pixel to the nearest RGB color in the TFLT palette 430 (block 345). The ALTs and LLTs for that pixel are determined by the corresponding ALT thickness in the y-axis of the TFLT palette 430, and the corresponding LLT thickness in the x-axis of the TFLT palette 430. As illustrated in FIG. 30, the TFLT palette 430 colors are actually represented by RGB values. The pixels in each of the pre-processed resulting images of the tear film are also converted and stored as RGB values, although any other color representation can be used as desired, as long as the palette and the image pixel data use the same representational color space. FIG. 30 illustrates the TFLT palette 430 in color pattern form with normalization applied to each red-green-blue (RGB) color value individually. Normalizing a TFLT palette is optional. The TFLT palette 430 in FIG. 30 is displayed using brightness control (i.e., normalization, as previously described) and without the RGB values included, which may be more visually pleasing to a clinician if shown on the display 174. The GUI utility 280 allows selection of different palettes by selecting a file in the palette file drop down 402, as illustrated in FIG. 19, each palette being specific to the choice of 2-wave vs. 3-wave mode, the chosen source's spectrum, and the chosen camera's RGB spectral responses. To determine the closest pixel color in the TFLT palette 430, a Euclidean distance color difference equation is employed to calculate the distance in color between the RGB value of a pixel from the pre-processed resulting image of the patient's tear film and RGB values in the TFLT palette 430 as follows below, although the present disclosure is not so limited:

$$\text{Diff.} = \sqrt{((R\text{pixel} - R\text{palette})^2 + (G\text{pixel} - G\text{palette})^2 + (B\text{pixel} - B\text{palette})^2)}$$

Thus, the color difference is calculated for all palette entries in the TFLT palette 430. The corresponding LLT and ALT values are determined from the color hue in the TFLT palette 430 having the least difference from each pixel in each frame of the pre-processed resulting images of the tear film. The results can be stored in RAM 258 or any other convenient storage medium. To prevent pixels without a close match to a color in the TFLT palette 430 from being included in a processed result of LLT and ALT, a setting can be made to discard pixels from the results if the distance between the color of a given pixel is not within the entered acceptable distance of a color value in the TFLT palette 430 (block 346 in FIG. 28). The GUI utility 280 in FIG. 19 illustrates this setting such as would be the case if made available to a technician or clinician. A distance range input box 408 is provided to allow the maximum distance value to be provided for a pixel in a tear film image to be included in LLT and ALT results. Alternatively, all pixels can be included in the LLT and ALT results by selecting the ignore distance selection box 410 in the GUI utility 280 of FIG. 19.

Figure 31:
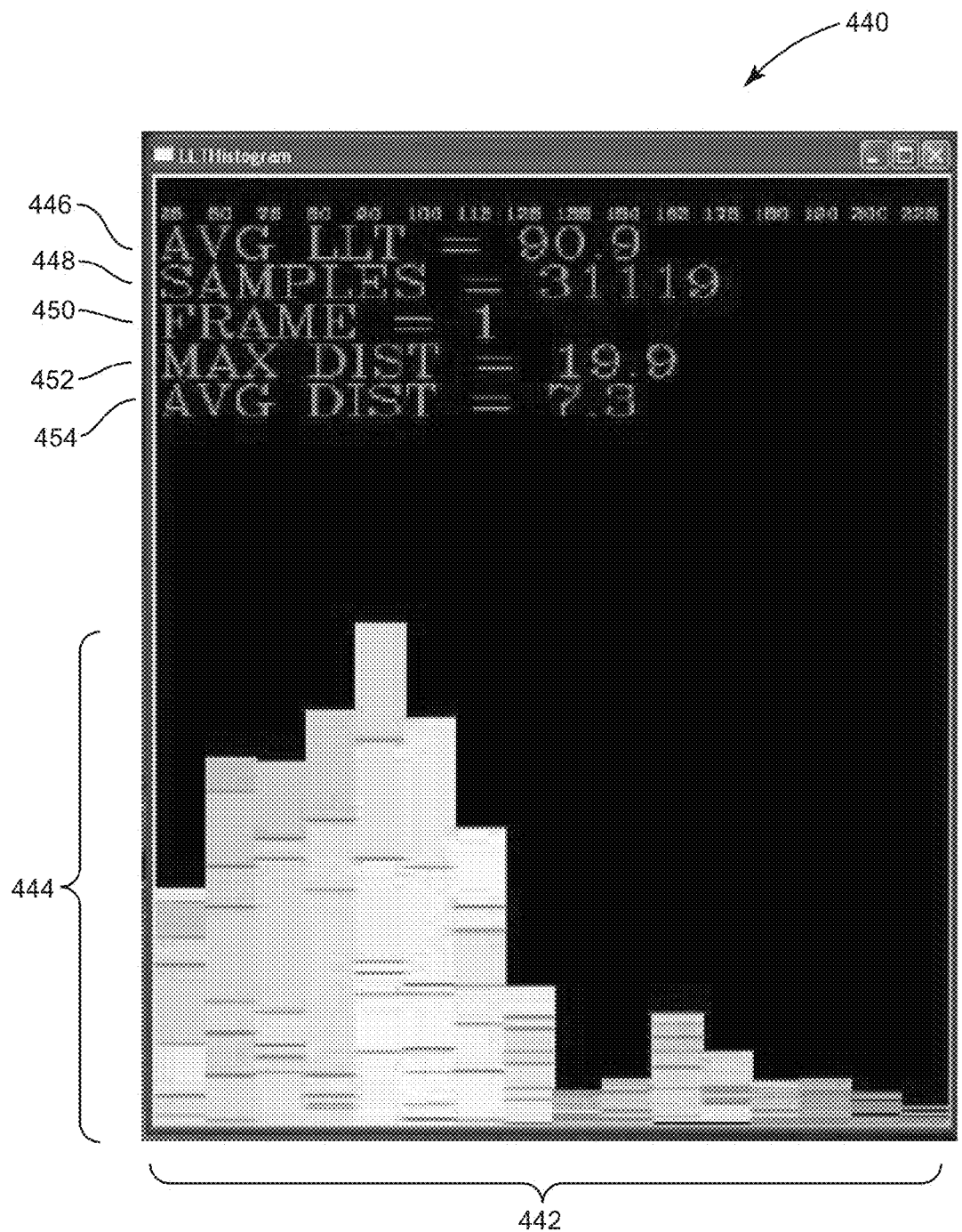
FIG. 31 is an exemplary histogram illustrating results of a comparison of interference interactions from the processed interference signal of specularly reflected light from a patient's tear film to the 3-wave tear film interference model of FIGS. 29A, 29B, and 30 for measuring TFLT of a patient's tear film.

Each LLT and ALT determined for each pixel from a comparison in the TFLT palette 430 via the closest matching color that is within a given distance (if that post-processing setting 266 is set) or for all LLT and ALT determined values is then used to build a TFLT histogram. The TFLT histogram is used to determine a weighted average of the LLT and ALT values for each pixel in the resulting image(s) of the patient's tear film to provide an overall estimate of the patient's LLT and ALT. FIG. 31 illustrates an example of such a TFLT histogram 440. This TFLT histogram 440 may be displayed as a result of the shown LLT histogram selection box 400 being selected in the GUI utility 280 of FIG. 19. As illustrated in FIG. 31, for each pixel within an acceptable distance, the TFLT histogram 440 is built in a stacked fashion with determined ALT values 444 stacked for each determined LLT value 442 (block 349 in FIG. 28). Thus, the TFLT histogram 440 represents LLT and ALT values 442, and 444, for each pixel. A horizontal line separates each stacked ALT value 444 within each LLT bar.

Figure 32:
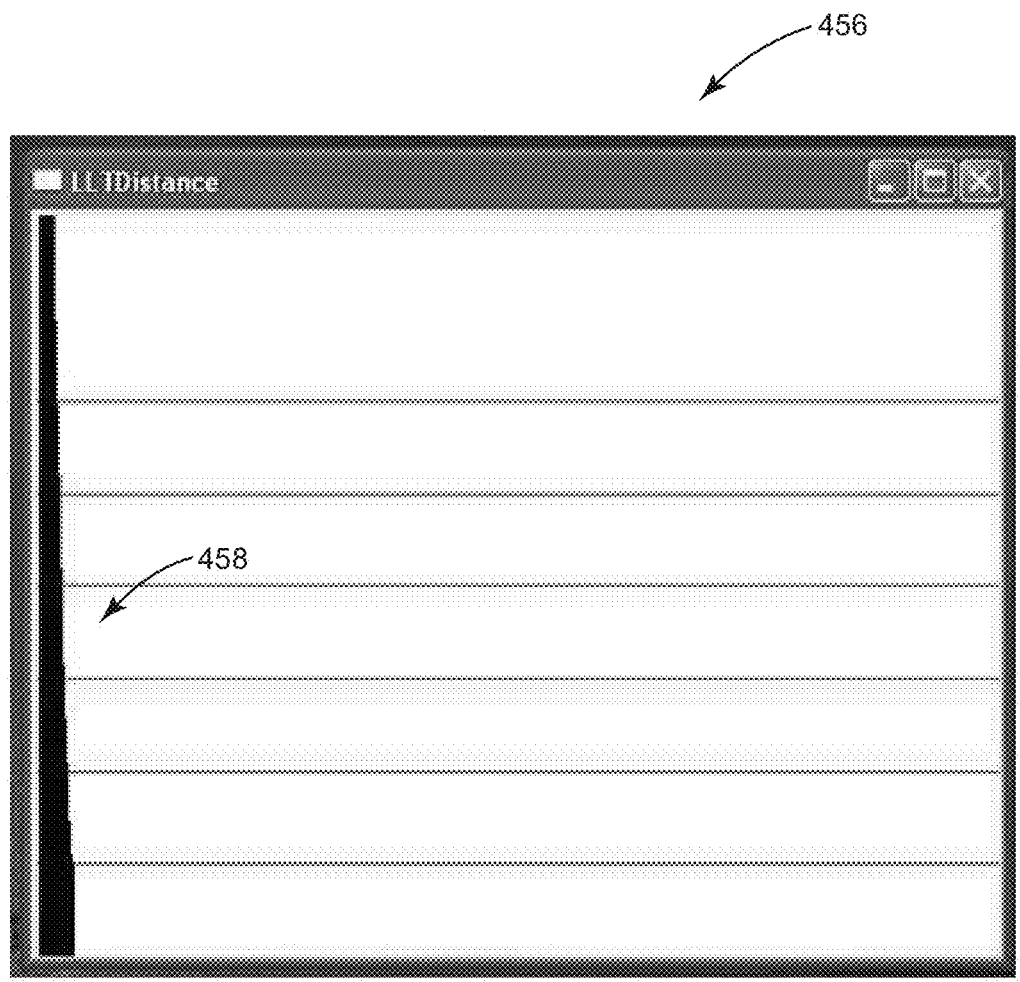
FIG. 32 is an exemplary histogram plot of distances in pixels between RGB color value representation of interference interactions from the processed interference signal of specularly reflected light from a patient's tear film and the nearest distance RGB color value in the 3-wave tear film interference model of FIGS. 29A, 29B, and 30.

One convenient way to determine the final LLT and ALT estimates is with a simple weighted average of the LLT and ALT values 442, 444 in the TFLT histogram 440. In the example of the TFLT histogram 440 in FIG. 31, the average LLT value 446 was determined to be 90.9 nm. The number of samples 448 (i.e., pixels) included in the TFLT histogram 440 was 31,119. The frame number 450 indicates which frame of the resulting video image is being processed, since the TFLT histogram 440 represents a single frame result, or the first of a frame pair in the case of background subtraction. The maximum distance 452 between the color of any given pixel among the 31,119 pixels and a color in the TFLT palette 430 was 19.9; 20 may have been the set limit (Maximum Acceptable Palette Distance) for inclusion of any matches. The average distance 454 between the color of each of the 31,119 pixels and its matching color in the TFLT palette 430 was 7.8. The maximum distance 452 and average distance 454 values provide an indication of how well the color values of the pixels in the interference signal of the specularly reflected light from the patient's tear film match the color values in the TFLT palette 430. The smaller the distance, the closer the matches. The TFLT histogram 440 can be displayed on the display 174 to allow a clinician to review this information graphically as well as numerically. If either the maximum distance 452 or average distance 454 values are too high, this may be an indication that the measured LLT and ALT values may be inaccurate, or that the image normalization is not of the correct value. Further imaging of the patient's eye and tear film, or system recalibration can be performed to attempt to improve the results. Also, a histogram 456 of the LLT distances 458 between the pixels and the colors in the TFLT palette 430 can be displayed as illustrated in FIG. 32 to show the distribution of the distance differences to further assist a clinician in judgment of the results.

Figure 33:
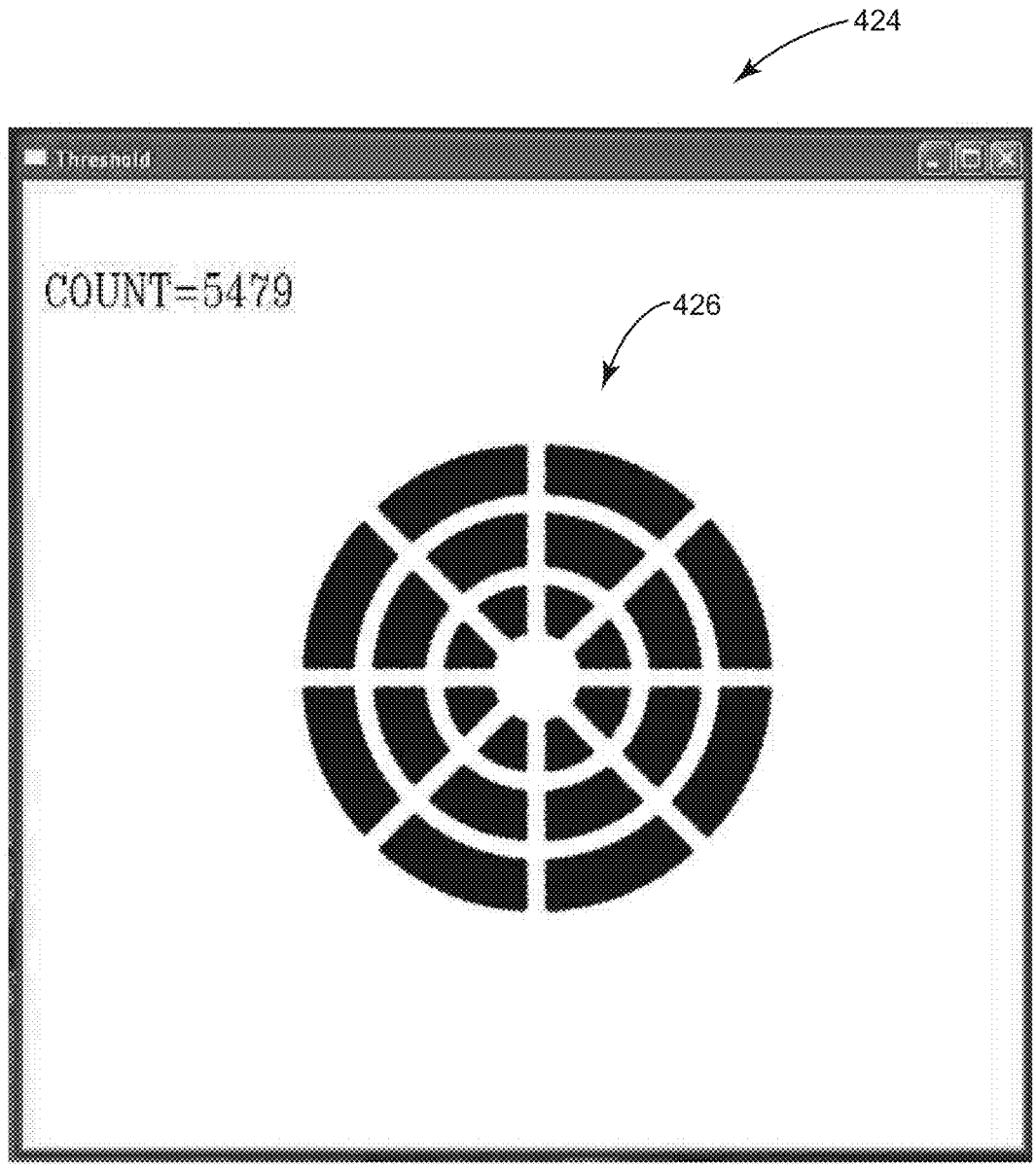
FIG. 33 is an exemplary threshold mask used during pre-processing of the tear film images.

Other results can be displayed on the display 174 of the OSI device 170 that may be used by a physician or technician to judge the LLT and/or ALT measurement results. For example, FIG. 33 illustrates a threshold window 424 illustrating a (inverse) threshold mask 426 that was used during pre-processing of the tear film images. In this example, the threshold window 424 was generated as a result of the show threshold window selection box 382 being selected in the GUI utility 280 of FIG. 19. This may be used by a clinician to evaluate whether the threshold mask looks abnormal. If so, this may have caused the LLT and ALT estimates to be inaccurate and may cause the clinician to discard the results and image the patient's tear film again. The maximum distance between the color of any given pixel among the 31,119 pixels and a color in the palette 430 was 19.9 in this example.

Figure 34:
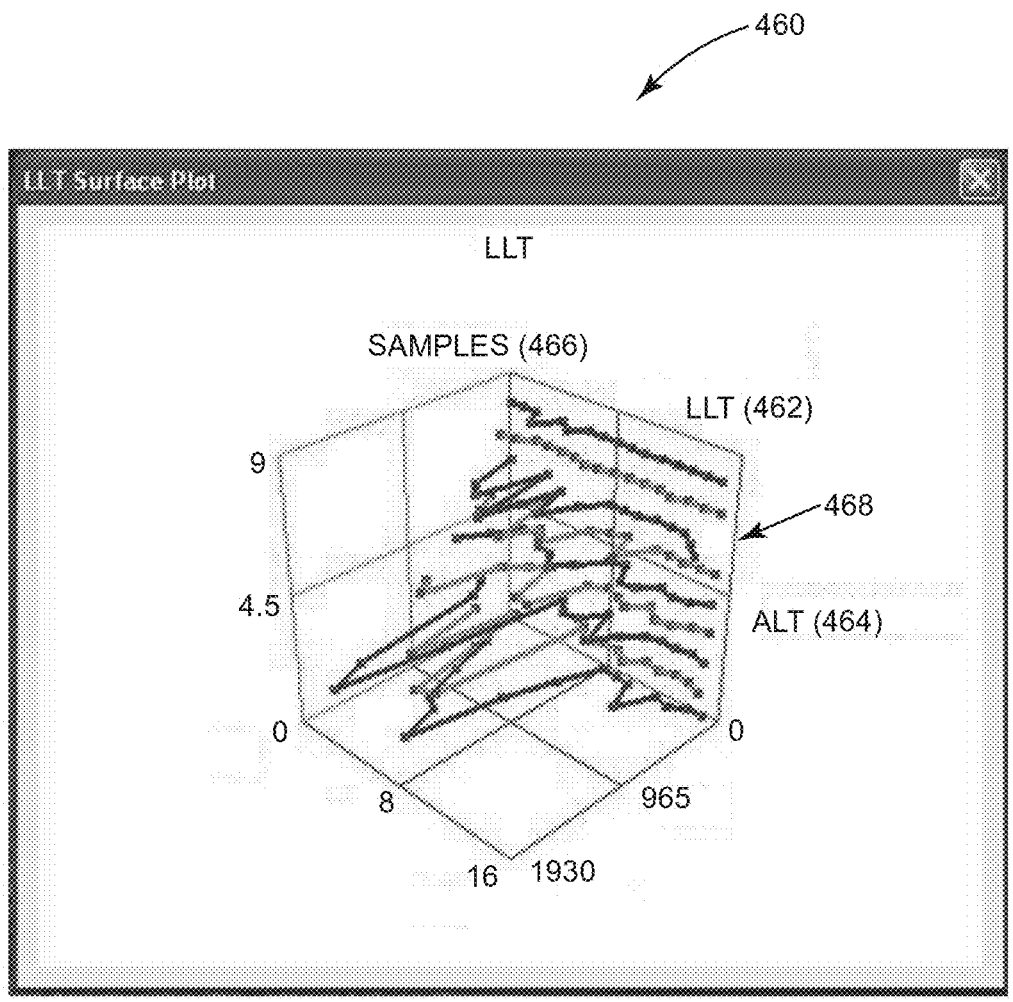
FIG. 34 is an exemplary three-dimensional (3D) surface plot of the measured LLT and ALT thicknesses of a patient's tear film.

FIG. 34 illustrates another histogram that may be displayed on the display 174 and may be useful to a clinician. As illustrated therein, a three-dimensional (3D) histogram plot 460 is illustrated. The clinician can choose whether the OSI device 170 displays this histogram plot 460 by selecting the 3D plot selection box 416 in the GUI utility 280 of FIG. 19, as an example, or the OSI device 170 may automatically display the histogram plot 460. The 3D histogram plot 460 is simply another way to graphically display the fit of the processed pixels from the pre-processed images of the tear film to the TFLT palette 430. The plane defined by the LLT 462 and ALT 464 axes represents the TFLT palette 430. The axis labeled "Samples" 466 is the number of pixels that match a particular color in the TFLT palette 430.

Figure 35:
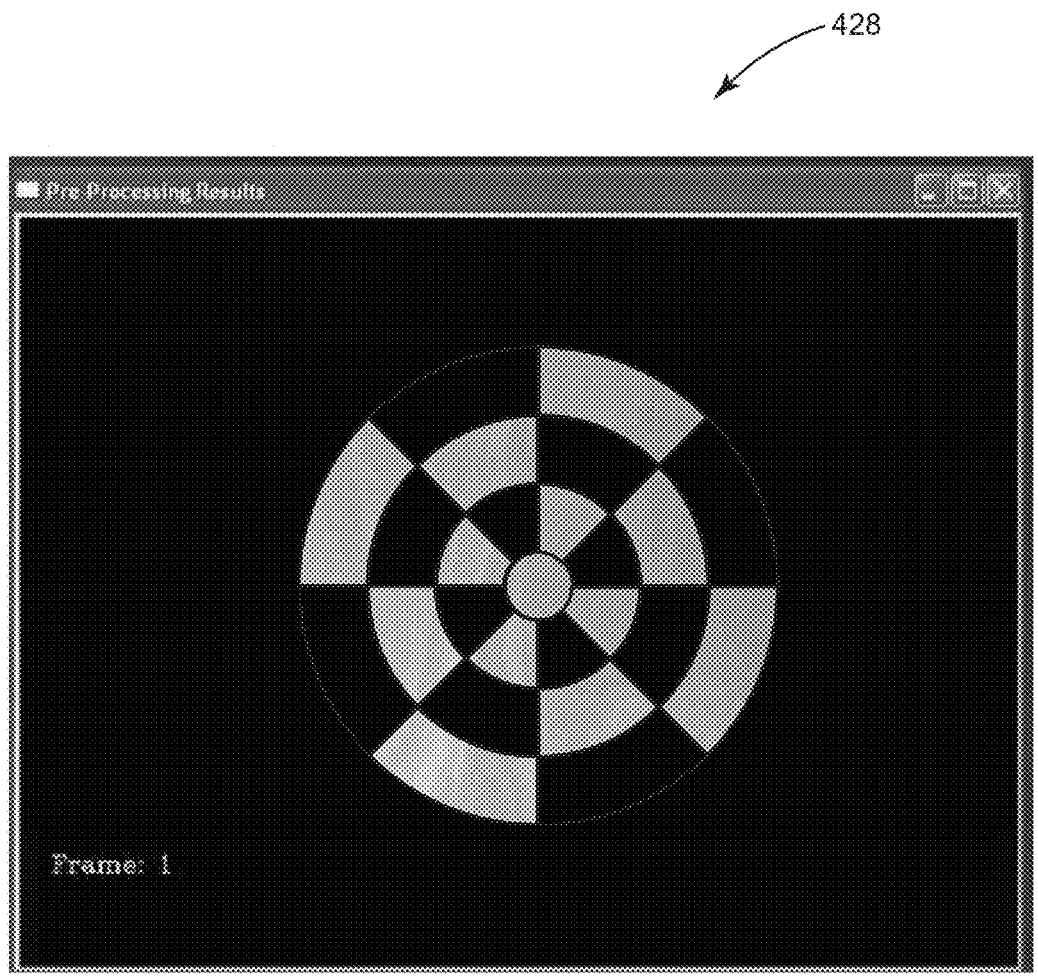
FIG. 35 is an exemplary image representing interference interactions of specularly reflected light from a patient's tear film results window based on replacing a pixel in the tear film image with the closest matching RGB color value in the normalized 3-wave tear film interference model of FIG. 30.

FIG. 35 illustrates a result image 428 of the specularly reflected light from a patient's tear film. However, the actual pixel value for a given area on the tear film is replaced with the determined closest matching color value representation in the TFLT palette 430 to a given pixel for that pixel location in the resulting image of the patient's tear film (block 347 in FIG. 28). This setting can be selected, for example, in the GUI utility 280 of FIG. 19. Therein, a "replace resulting image . . ." selection box 412 is provided to allow a clinician to choose this option. Visually displaying interference interactions representing the closest matching color value to the interference interactions in the interference signal of the specularly reflected light from a patient's tear film in this manner may be helpful to determine how closely the tear film interference model matches the actual color value representing the resulting image (or pixels in the image). Moreover, a selection box 414 is provided to allow the clinician to select a showing of a histogram of the images channels.

Ambiguities can arise when calculating the nearest distance between an RGB value of a pixel from a tear film image and RGB values in a TFLT palette, such as TFLT palettes 430 and 430' in FIGS. 29A and 29B as examples. This is because when the theoretical LLT of the TFLT palette is plotted in RGB space for a given ALT in three-dimensional (3D) space, the TFLT palette 469 is a locus that resembles a pretzel-like curve, as illustrated with a 2-D representation in the exemplary TFLT palette locus 470 in FIG. 36. Ambiguities can arise when a tear film image RGB pixel value has close matches to the TFLT palette locus 470 at significantly different LLT levels. For example, as illustrated in the TFLT palette locus 470 in FIG. 36, there are three (3) areas of close intersection 472, 474, 476 between RGB values in the TFLT palette locus 470 even though these areas of close intersection 472, 474, 476 represent substantially different LLTs on the TFLT palette locus 470. This is due to the cyclical phenomenon caused by increasing orders of optical wave interference, and in particular, first order versus second order interference for the LLT range in the tear films. Thus, if an RGB value of a tear film image pixel is sufficiently close to two different LLT points in the TFLT palette locus 470, the closest RGB match may be difficult to match. The closest RGB match may be to an incorrect LLT in the TFLT palette locus 470 due to error in the camera and translation of received light to RGB values. Thus, it may be desired to provide further processing when determining the closest RGB value in the TFLT palette locus 470 to RGB values of tear film image pixel values when measuring TFLT.

Figure 36:
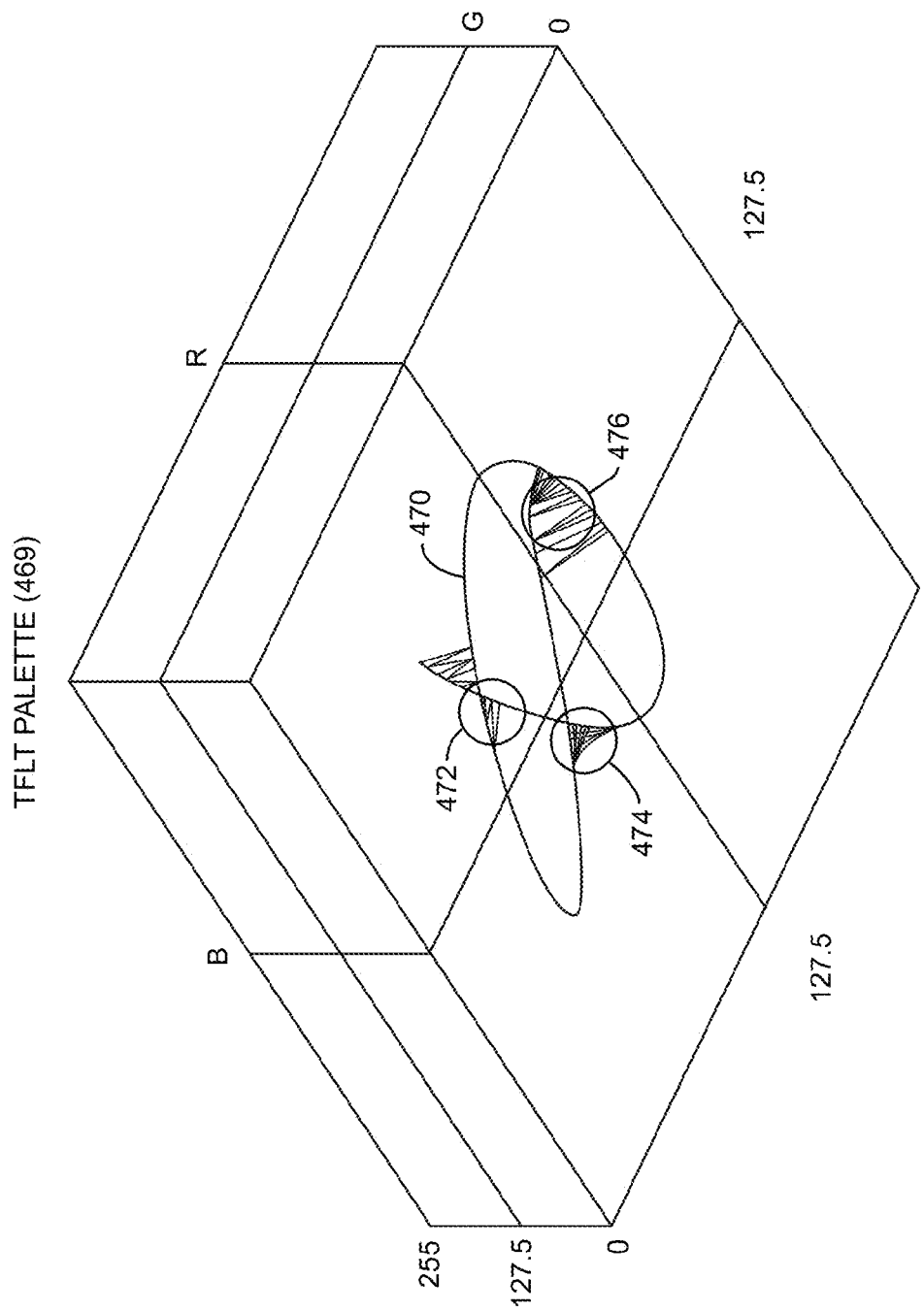
FIG. 36 is an exemplary TFLT palette curve for a TFLT palette of LLTs plotted in RGB space for a given ALT in three-dimensional (3D) space.

In this regard, there are several possibilities that can be employed to avoid ambiguous RGB matches in a TFLT palette. For example, the maximum LLT values in a TFLT palette may be limited. For example, the TFLT palette locus 470 in FIG. 36 includes LLTs between 10 nm and 300 nm. If the TFLT palette locus 470 was limited in LLT range, such as 240 nm as illustrated in the TFLT palette locus 478 in FIG. 37, two areas of close intersection 474, 476 in the TFLT palette 469 in FIG. 36 are avoided in the TFLT palette 469 of FIG. 37. This restriction of the LLT ranges may be acceptable based on clinical experience since most patients do not exhibit tear film colors above the 240 nm range and dry eye symptoms are more problematic at thinner LLTs. In this scenario, the limited TFLT palette 469 of FIG. 37 would be used as the TFLT palette in the post-processing system 262 in FIG. 28, as an example.

Figure 37:
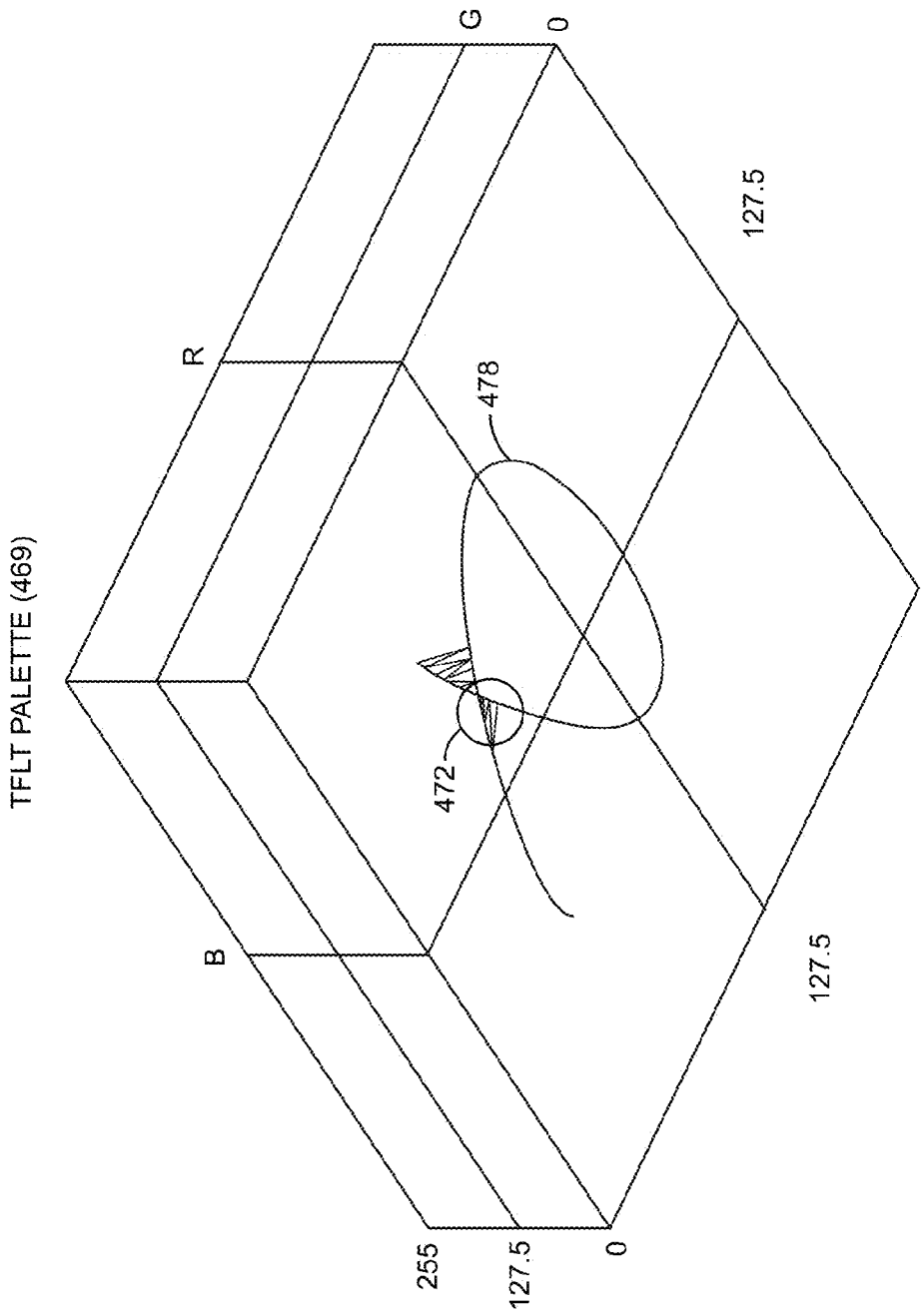
FIG. 37 is an exemplary TFLT palette curve for the TFLT palette of FIG. 36 with LLTs limited to a maximum LLT of 240 nm plotted in RGB space for a given ALT in three-dimensional (3D) space.

Even by eliminating two areas of close intersection 474, 476 in the TFLT palette 469, as illustrated in FIG. 37, the area of close intersection 472 still remains in the TFLT palette locus 478. In this embodiment, the area of close intersection 472 is for LLT values near 20 nm versus 180 nm. In these regions, the maximum distance allowed for a valid RGB match is restricted to a value of about half the distance of the TFLT palette's 469 nearing ambiguity distance. In this regard, RGB values for tear film pixels with match distances exceeding the specified values can be further excluded from the TFLT calculation to avoid tear film pixels having ambiguous corresponding LLT values for a given RGB value to avoid error in TFLT measurement as a result.

Figure 38:
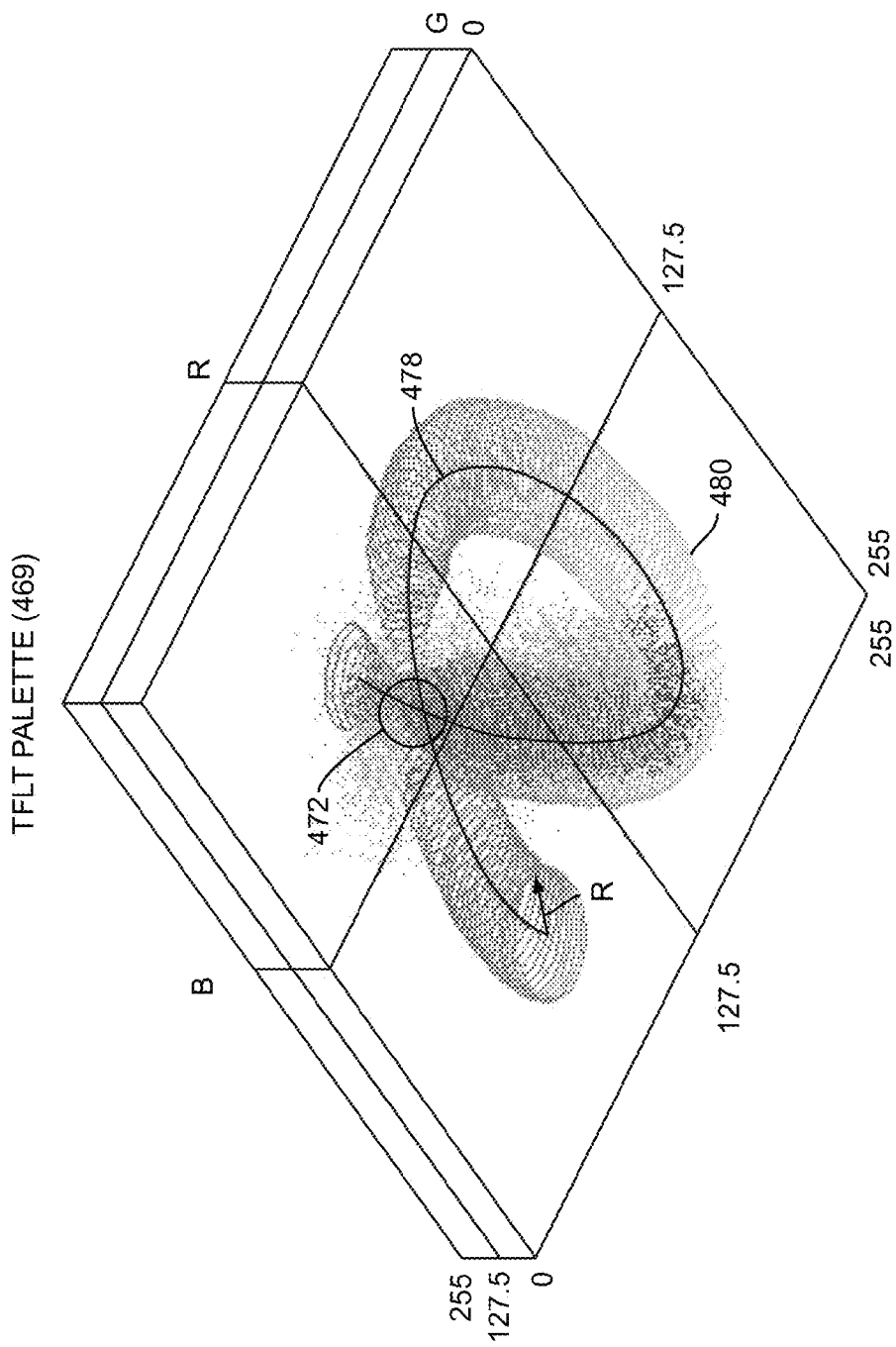
FIG. 38 illustrates the TFLT palette curve of FIG. 37 with an acceptable distance to palette (ADP) filter shown to discriminate tear film pixel values having RGB values that correspond to ambiguous LLTs.

In this regard, FIG. 38 illustrates the TFLT palette locus 478 in FIG. 37, but with a circle of radius R swept along the path of the TFLT palette locus 478 in a cylinder or pipe 480 of radius R. Radius R is the acceptable distance to palette (ADP), which can be configured in the control system 240. When visualized as a swept volume inside the cylinder or pipe 480, RGB values of tear film image pixels that fall within those intersecting volumes may be considered ambiguous and thus not used in calculating TFLT, including the average TFLT. The smaller the ADP is set, the more poorly matching tear film image pixels that may be excluded in TFLT measurement, but less pixels are available for use in calculation of TFLT. The larger the ADP is set, the less tear film image pixels that may be excluded in TFLT measurement, but it is more possible that incorrect LLTs are included in the TFLT measurement. The ADP can be set to any value desired. Thus, the ADP acts effectively to filter out RGB values for tear film images that are deemed a poor match and those that may be ambiguous according to the ADP setting. This filtering can be included in the post-processing system 262 in FIG. 28, as an example, and in step 346 therein, as an example.

Graphical User Interface (GUI)

Figure 39:
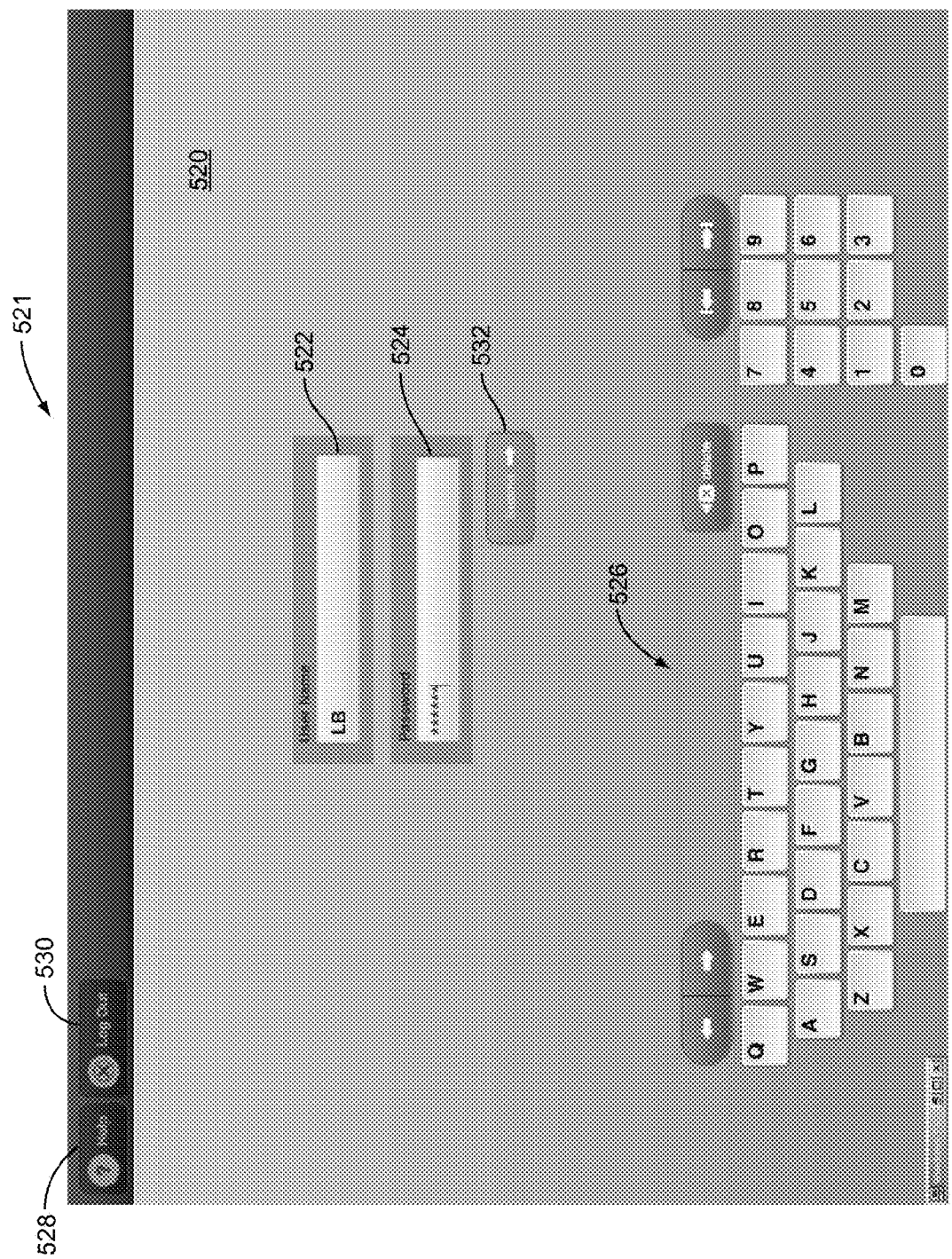
FIG. 39 is an exemplary login screen to a user interface system for controlling and accessing the OSI device of FIG. 9-11.

In order to operate the OSI device 170, a user interface program may be provided in the user interface system 278 (see FIG. 17A) that drives various graphical user interface (GUI) screens on the display 174 of the OSI device 170 in addition to the GUI utility 280 of FIG. 19 to allow access to the OSI device 170. Some examples of control and accesses have been previously described above. Examples of these GUI screens from this GUI are illustrated in FIGS. 39-45 and described below. The GUI screens allow access to the control system 240 in the OSI device 170 and to features provided therein. As illustrated in FIG. 39, a login GUI screen 520 is illustrated. The login GUI screen 520 may be provided in the form of a GUI window 521 that is initiated when a program is executed. The login GUI screen 520 allows a clinician or other user to log into the OSI device 170. The OSI device 170 may have protected access such that one must have an authorized user name and password to gain access. This may be provided to comply with medical records and privacy protection laws. As illustrated therein, a user can enter their user name in a user name text box 522 and a corresponding password in the password text box 524. A touch or virtual keyboard 526 may be provided to allow alphanumeric entry. To gain access to help or to log out, the user can select the help and log out tabs 528, 530, which may remain resident and available on any of the GUI screens. After the user is ready to login, the user can select the submit button 532. The user name and password entered in the user name text box 522 and the password text box 524 are verified against permissible users in a user database stored in the disk memory 268 in the OSI device 170 (see FIG. 17A).

Figure 40:
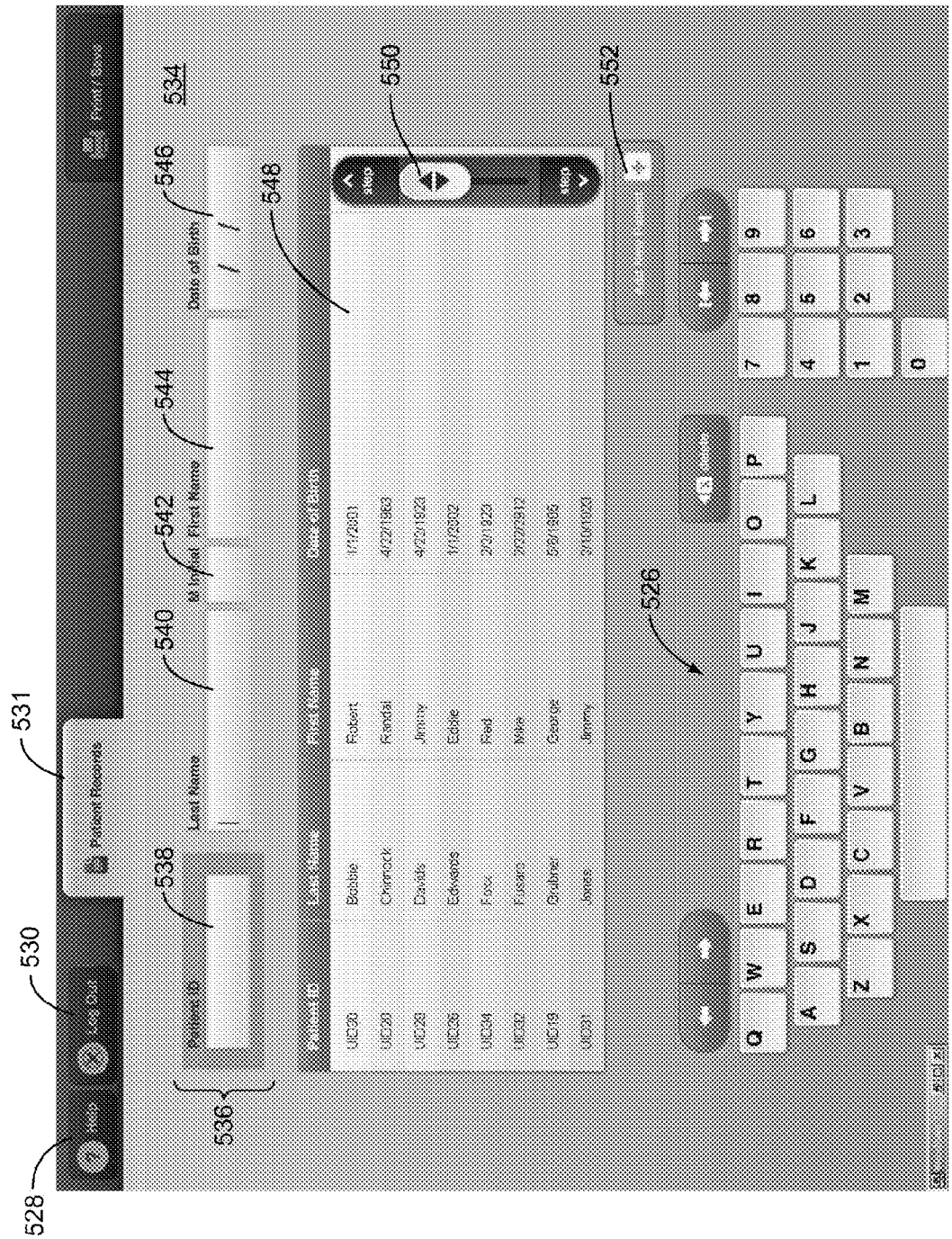
FIG. 40 illustrates an exemplary interface screen for accessing a patient database interface in the OSI device of FIG. 9-11.

If a user successfully logs into the OSI device 170, a patient GUI screen 534 appears on the display 174 with the patient records tab 531 selected, as illustrated in FIG. 40. The patient GUI screen 534 allows a user to either create a new patient or to access an existing patient. A new patient or patient search information can be entered into any of the various patient text boxes 536 that correspond to patient fields in a patient database. Again, the information can be entered through the virtual keyboard 526, facilitated with a mouse pointing device (not shown), a joystick, or with a touch screen covering on the display 174. These include a patient ID text box 538, patient last name text box 540, patient middle initial text box 542, a patient first name text box 544, and a date of birth text box 546. This data can be entered for a new patient, or used to search a patient database on the disk memory 268 (see FIG. 17A) to access an existing patient's records. The OSI device 170 may contain disk memory 268 with enough storage capability to store information and tear film images regarding a number of patients. Further, the OSI device 170 may be configured to store patient information outside of the OSI device 170 on a separate local memory storage device or remotely. If the patient data added in the patient text boxes 536 is for a new patient, the user can select the add new patient button 552 to add the new patient to the patient database. The patients in the patient database can also be reviewed in a scroll box 548. A scroll control 550 allows up and down scrolling of the patient database records. The patient database records are shown as being sorted by last name, but may be sortable by any of the patient fields in the patient database.

Figure 41:
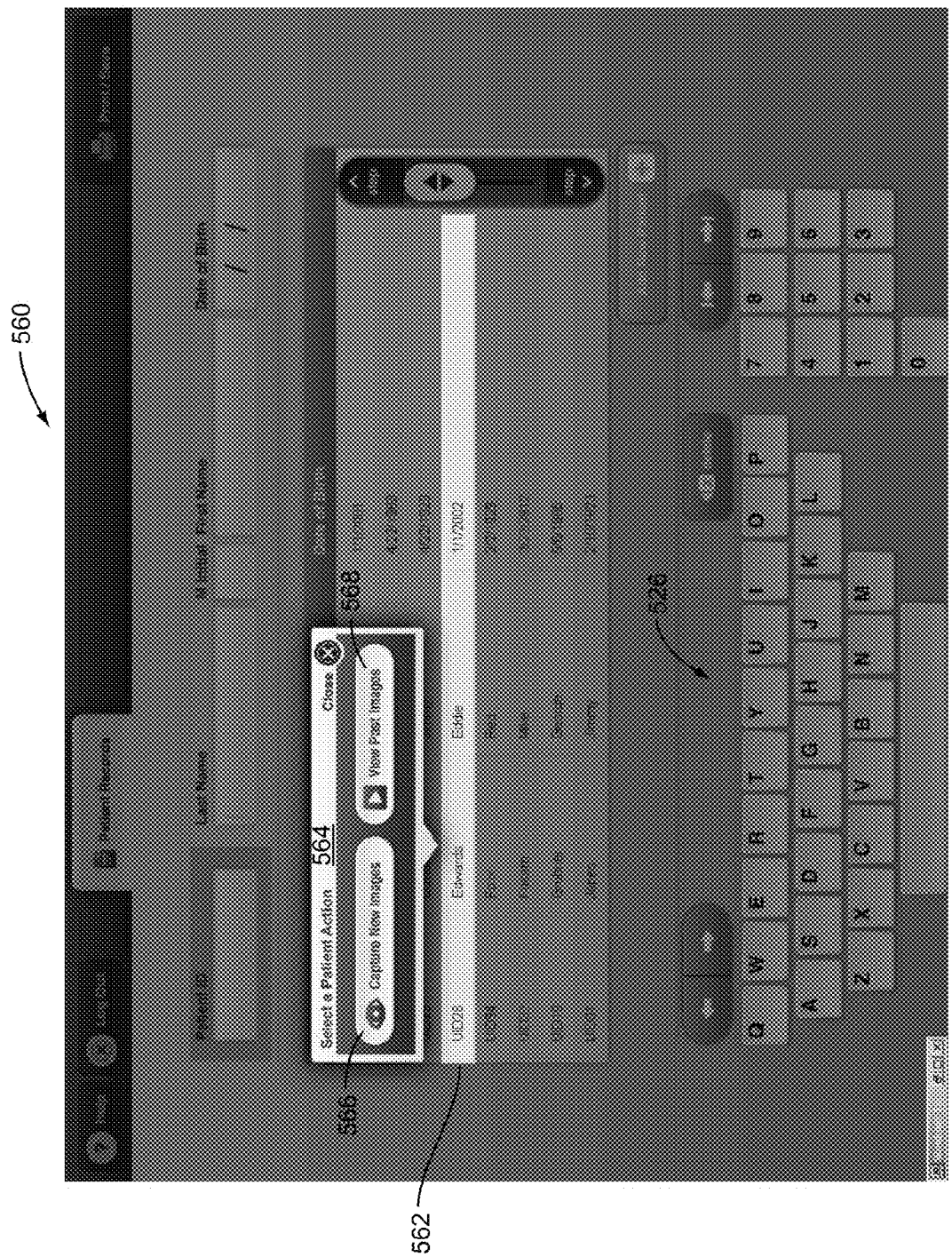
FIG. 41 illustrates a patient action control box for selecting to either capture new tear film images of a patient in the patient database or view past captured images of the patient from the OSI device of FIGS. 9-11.
Figure 42:
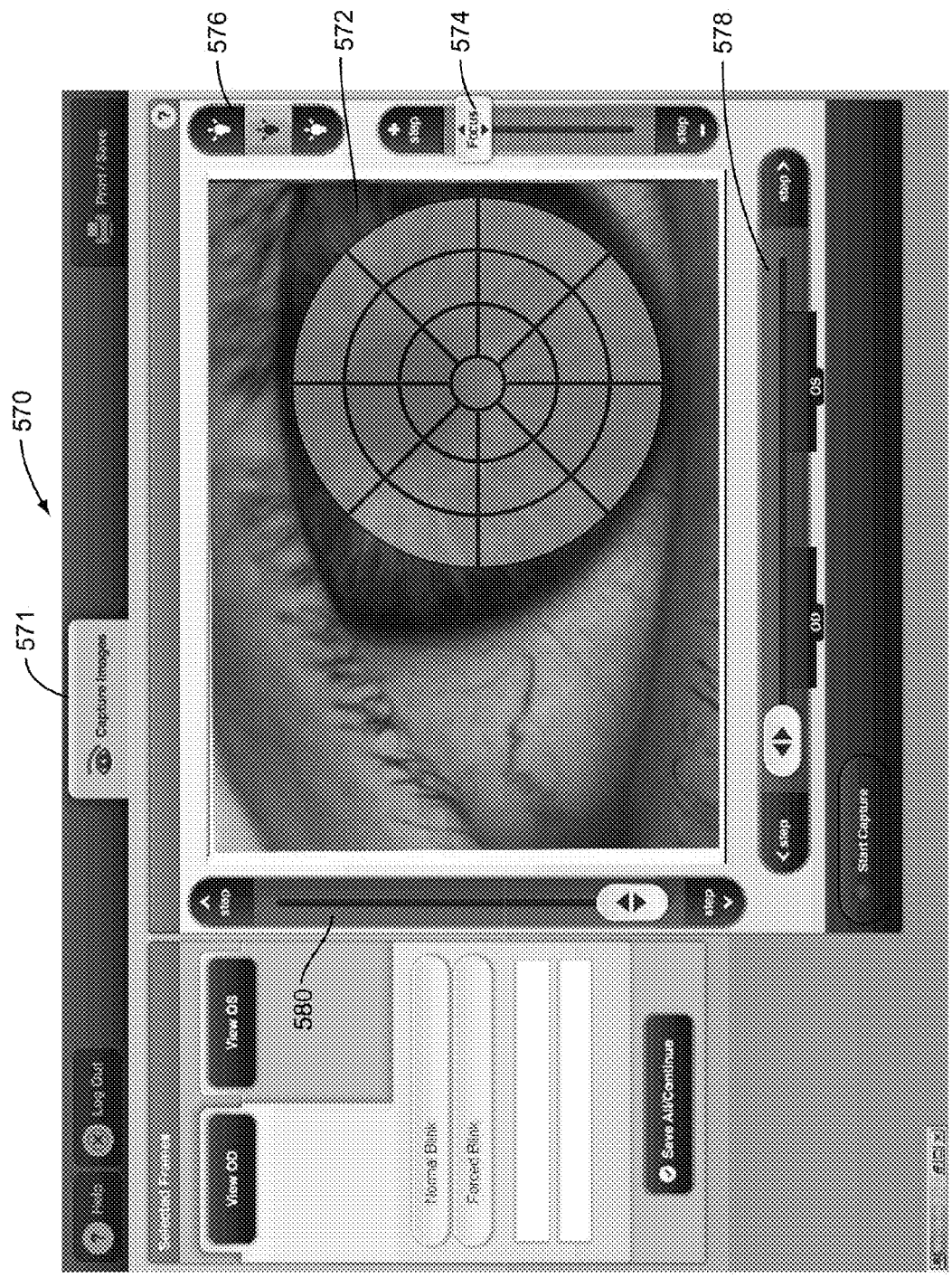
FIG. 42 illustrates a viewing interface for viewing a patient's tear film either captured in real-time or previously captured by the OSI device of FIGS. 9-11.

If a patient is selected in the scroll box 548, which may be an existing or just newly added patient, as illustrated in the GUI screen 560 in FIG. 41, the user is provided with an option to either capture new tear film images of the selected patient or to view past images, if past tear film images are stored for the selected patient on disk memory 268. In this regard, the selected patient is highlighted 562 in the patient scroll box 548, and a select patient action pop-up box 564 is displayed. The user can either select the capture new images button 566 or the view past images button 568. If the capture new images button 566 is selected, the capture images GUI 570 is displayed to the user under the capture images tab 571 on the display 174, which is illustrated in FIG. 42. As illustrated therein, a patient eye image viewing area 572 is provided, which is providing images of the patient's eye and tear film obtained by the video camera 198 in the OSI device 170. In this example, the image is of an overlay of the subtracted first and second tiled pattern images of the patient's tear film onto the raw image of the patient's eye and tear film, as previously discussed. The focus of the image can be adjusted via a focus control 574. The brightness level of the image in the viewing area 572 is controlled via a brightness control 576. The user can control the position of the video camera 198 to align the camera lens with the tear film of interest whether the lens is aligned with the patient's left or right eye via an eye selection control 578. Each frame of the patient's eye captured by the video camera 198 can be stepped via a stepping control 580. Optionally, or in addition, a joystick may be provided in the OSI device 170 to allow control of the video camera 198.

Figure 43:
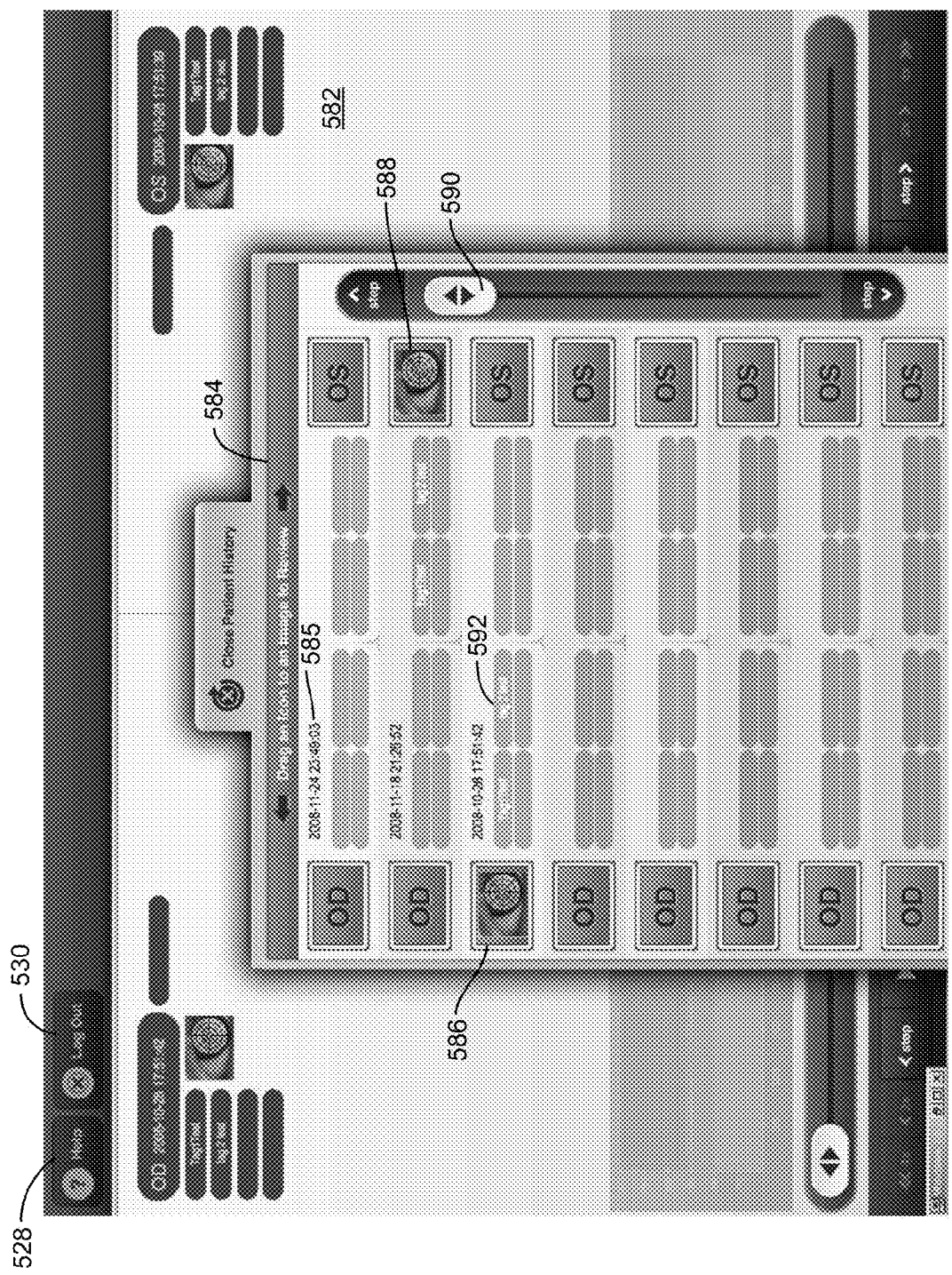
FIG. 43 illustrates a tear film image database for a patient.

The stored images of the patient's eye and tear film can also be accessed from a patient history database stored in disk memory 268. FIG. 43 illustrates a patient history GUI screen 582 that shows a pop-up window 584 showing historical entries for a given patient. For each tear film imaging, a time and date stamp 585 is provided. The images of a patient's left and right eye can be shown in thumbnail views 586, 588 for ease in selection by a user. The stored images can be scrolled up and down in the pop-up window 584 via a step scroll bar 590. Label names in tag boxes 592 can also be associated with the images. Once a desired image is selected for display, the user can select the image to display the image in larger view in the capture images GUI 570 in FIG. 42. Further, two tear film images of a patient can be simultaneously displayed from any current or prior examinations for a single patient, as illustrated in FIG. 44.

Figure 44:
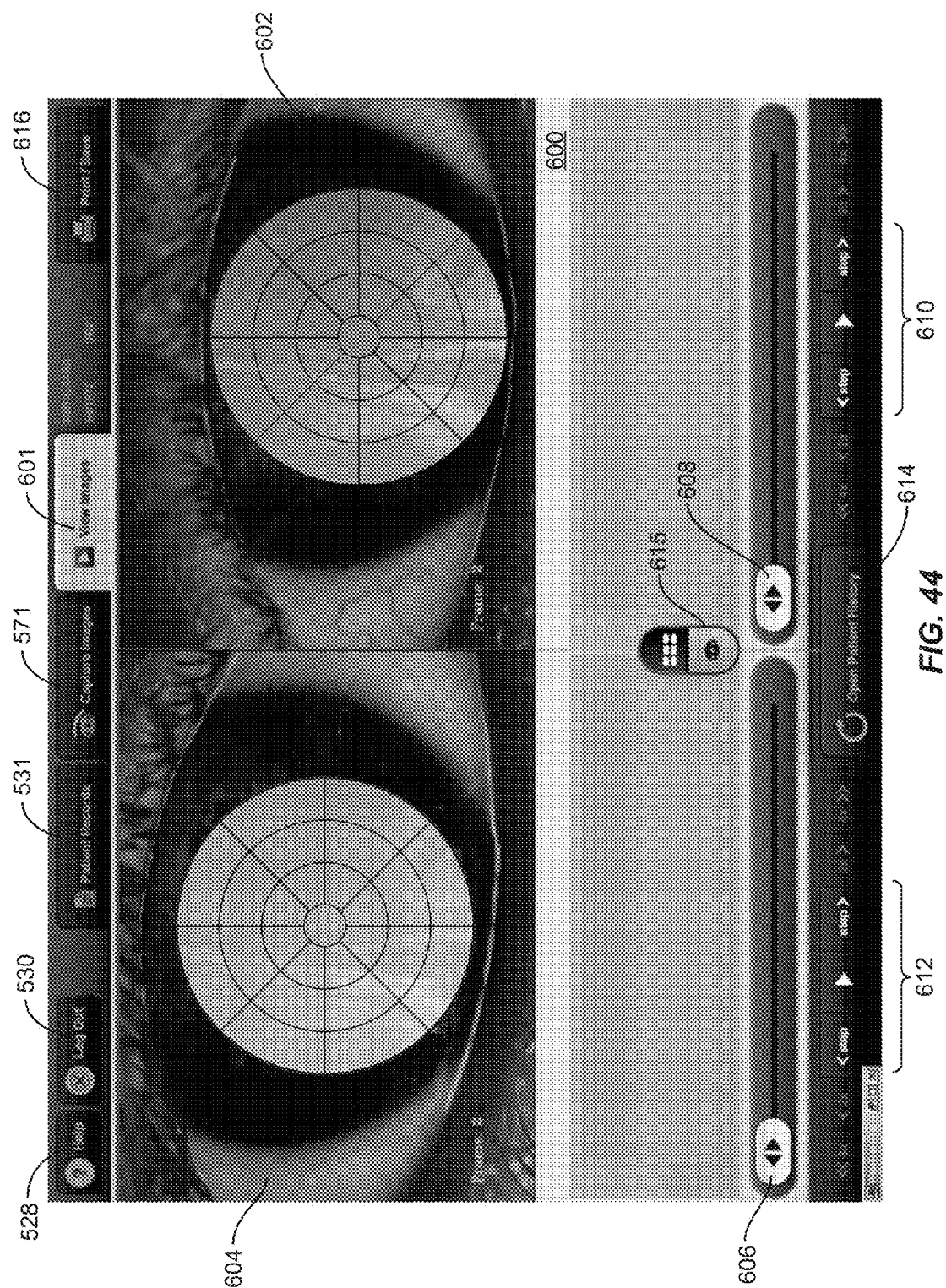
FIG. 44 illustrates a view images GUI screen showing an overlaid image of interference interactions of the interference signals from specularly reflected light from a patient's tear film overtop an image of the patient's eye for both the patient's left and right eyes side by side.
Figure 45:
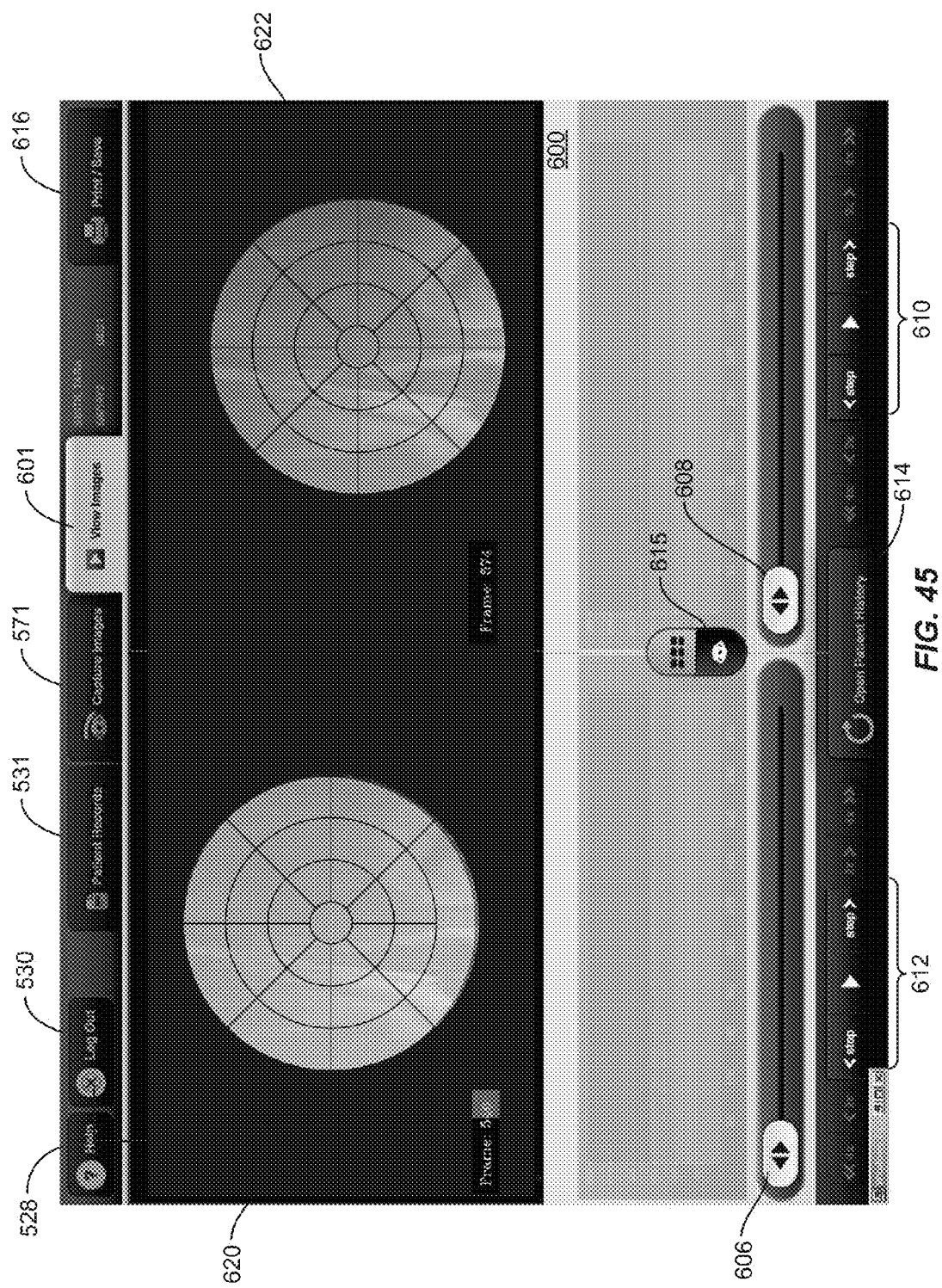
FIG. 45 illustrates the GUI screen of FIG. 44 with the images of the patient's eye toggled to show only the interference interactions of the interference signals from specularly reflected light from a patient's tear film.

As illustrated in FIG. 44, a view images GUI screen 600 is shown, wherein a user has selected a view images tab 601 to display images of a patient's ocular tear film. In this view images GUI screen 600, both images of the patient's left eye 602 and right eye 604 are illustrated side by side. In this example, the images 602, 604 are overlays of the subtracted first and second tiled pattern images of the patients tear film onto the raw image of the patient's eye and tear film, as previously discussed. Scroll buttons 606, 608 can be selected to move a desired image among the video of images of the patient's eye for display in the view images GUI screen 600. Further, step and play controls 610, 612 allow the user to control playing a stored video of the patient's tear film images and stepping through the patient's tear film images one at a time, if desired. The user can also select an open patient history tab 614 to review information stored regarding the patient's history, which may aid in analysis and determining whether the patient's tear film has improved or degraded. A toggle button 615 can be selected by the user to switch the images 602, 604 from the overlay view to just the images 620, 622, of the resulting tiled interference interactions of specularly reflected light from the patient's tear films, as illustrated in FIG. 45. As illustrated in FIG. 45, only the resulting interference interactions from the patient's tear film are illustrated. The user may select this option if it is desired to concentrate the visual examination of the patient's tear film solely to the interference interactions.

Many modifications and other embodiments of the disclosure set forth herein will come to mind to one skilled in the art to which the disclosure pertains having the benefit of the teachings presented in the foregoing descriptions and the associated drawings. These modifications include, but are not limited to, the type of light source or illuminator, the number of tiling groups and modes, the arrangement of tile groups, the type of imaging device, image device settings, the relationship between the illuminator and an imaging device, the control system, the type of tear film interference model, and the type of electronics or software employed therein, the display, the data storage associated with the OSI device for storing information, which may also be stored separately in a local or remotely located remote server or database from the OSI device, any input or output devices, settings, including pre-processing and post-processing settings. Note that subtracting the second image from the first image as disclosed herein includes combining the first and second images, wherein like signals present in the first and second images are cancelled when combined. Further, the present disclosure is not limited to illumination of any particular area on the patient's tear film or use of any particular color value representation scheme.

Therefore, it is to be understood that the disclosure is not to be limited to the specific embodiments disclosed and that modifications and other embodiments are intended to be included within the scope of the appended claims. It is intended that the present disclosure cover the modifications and variations of this disclosure provided they come within the scope of the appended claims and their equivalents. Although specific terms are employed herein, they are used in a generic and descriptive sense only and not for purposes of limitation.

What is claimed is:

1. An apparatus for imaging an eye, comprising:
 a multi-wavelength light source configured to emit light to an eye; and
 a control system configured to:
 (a) spatially modulate light from the multi-wavelength light source to project a first circular pattern onto the eye, such that at least one first portion of the eye receives emitted light from the multi-wavelength light source and at least one second portion of the eye does not receive the emitted light from the multi-wavelength light source;
 (b) receive at an imaging device, at least one first image containing at least one first signal associated with an ocular property of the eye comprising at least one of corneal shape and ocular tear film thickness, comprises the emitted light reflected from the at least one first portion of the eye and at least one background signal;
 (c) spatially modulate light from the multi-wavelength light source to project a second circular pattern onto the eye, such that the at least one first portion of the eye does not receive emitted light from the multi-wavelength light source and the at least one second portion on the eye receives the emitted light from the multi-wavelength light source;
 (d) receive at the imaging device, at least one second image containing at least one second signal comprising only the at least one background signal; and
 (e) subtract the at least one second image from the at least one first image to generate at least one resulting image containing a resultant signal that represents the ocular property of the eye.

2. The apparatus of claim 1, further including a light modulator system communicatively coupled to the control system to spatially modulate light from the multi-wavelength light source to alternately project the first circular pattern and the second circular pattern onto the eye to illuminate the ocular property thereby generating the at least one first signal and the at least one second signal of the ocular property.

3. The apparatus of claim 2, wherein the light modulator system includes a disk disposed between the imaging device and eye for sequentially projecting the first circular pattern and the second circular pattern onto the eye when the disk is illuminated, and wherein the disk includes a central aperture for the imaging device to receive light reflected from the eye.

4. The apparatus of claim 3, wherein the disk is patterned with a plurality of concentric circles having alternating opaque and translucent sections with edges that form radials.

5. The apparatus of claim 4, wherein the light modulator system further includes an electric motor and a drive mechanism for rotating the disk to alternately generate the first circular pattern while the imaging device captures at least one first image containing the at least one first signal of the ocular property and to generate the second circular pattern while the imaging device captures at least one second image containing the at least one second signal of the ocular property.

6. The apparatus of claim 3, wherein the disk is a frusto-conical shaped disk having an open major base that faces the eye and an open minor base that faces the imaging device.

7. The apparatus of claim 3, wherein the disk includes pixels that when illuminated by the multi-wavelength light source projects the first circular pattern in response to a first control signal and projects the second circular pattern in response to a second control signal.

8. The apparatus of claim 1, wherein the multi-wavelength light source is comprised of a multi-wavelength Lambertian light source configured to uniformly or substantially uniformly illuminate the eye.

9. The apparatus of claim 1, wherein the control system is further configured to display at least one of the at least one first image, the at least one second image, or the at least one resulting image on a visual display.

10. The apparatus of claim 9, wherein the control system is further configured to display the at least one resulting image overlaid onto at least one of the at least one first image and the at least one second image on the visual display.

11. The apparatus of claim 1, wherein the ocular property an ocular tear film thickness and the at least one first signal is optical wave interference of specularly reflected light from the ocular tear film combined with the at least one background signal.

12. The apparatus of claim 11, wherein the imaging device is configured to capture the at least one second image when the multi-wavelength light source is not illuminating the at least one second portion of the ocular tear film.

13. The apparatus of claim 11, wherein the imaging device is configured to capture the at least one second image when the multi-wavelength light source is illuminating the at least one second portion of the ocular tear film.

14. The apparatus of claim 11, wherein the control system is configured to receive the at least one first image by being configured to:
    capture a first circular tiled pattern of the specularly reflected light including the at least one background signal from the at least a first portion of the ocular tear film in the at least one first image by the imaging device; and
    capture a second circular tiled pattern of the specularly reflected light including the at least one background signal from the at least one second portion of the ocular tear film in the at least one second image by the imaging device.

15. The apparatus of claim 14, wherein the control system is configured to receive only the at least one second image containing the at least one background signal from the ocular tear film captured by the imaging device by being configured to:
    capture the at least one background signal from the at least one second portion in the first circular tiled pattern in the at least one first image; and
    capture the at least one background signal from the at least one first portion of the second circular tiled pattern in the at least one second image.

16. The apparatus of claim 15, wherein the control system is further configured to combine the at least one first image to the at least one second image to form the at least one resulting image in a circular pattern containing the optical wave interference of specularly reflected light from the ocular tear film with the at least one background signal removed or reduced.

17. The apparatus of claim 11, wherein the control system is further configured to:
    (f) convert at least a portion of the at least one resulting image representing the optical wave interference of the specularly reflected light from at least a portion of the ocular tear film into at least one color-based value;
    (g) compare the at least one color-based value to a tear film layer optical wave interference model; and
    (h) measure a tear film layer thickness (TFLT) of the at least a portion of the ocular tear film based on the comparison of the at least one color-based value to the tear film layer optical wave interference model.

18. The apparatus of claim 17, wherein the control system configured to measure the TFLT of the at least a portion of the ocular tear film based on the comparison of the at least one color-based value to the tear film layer optical wave interference model further comprises measuring at least one of a lipid layer thickness (LLT) and an aqueous layer thickness (ALT).

19. The apparatus of claim 11, wherein the at least one first signal and at least one second signal are also associated with the ocular property of the eye comprising corneal shape and ocular tear film thickness.

20. The apparatus of claim 19, wherein the first circular pattern and second circular pattern are generated by spatially modulating light with a disk comprised from the group consisting of a plurality of concentric circles having alternating opaque and translucent sections including edges that form radials.

21. The apparatus of claim 19, wherein the control system is further configured to subtract the at least one second image from the at least one first image to generate at least one resulting image is a Placido pattern that comprises concentric circles and radials.

22. The apparatus of claim 1, wherein the ocular property includes corneal shape and the at least one first signal is associated with at least one first portion of the eye, and the at least one second signal is associated with at least a second portion of the eye.

23. The apparatus of claim 22, wherein the first circular pattern and second circular pattern are generated by spatially modulating light with a disk comprised from the group consisting of a plurality of concentric circles having alternating opaque and translucent sections including edges that form radials.

24. The apparatus of claim 22, wherein the at least one first portion and the at least a second portion are comprised of equal or approximately equal areas.

25. The apparatus of claim 22, wherein the control system is further configured to subtract the at least one second image from the at least one first image to generate at least one resulting image is a Placido pattern that comprises concentric circles and radials.

26. The apparatus of claim 25, wherein the control system is further configured to display the at least one resulting image of the Placido pattern on a visual display.

27. A method for imaging an eye, comprising:
spatially modulating light from a multi-wavelength light source configured to emit light to an eye to project a first circular pattern onto the eye, such that at least one portion of the eye receives emitted light from the multi-wavelength light source and at least one second portion of the eye does not receive the emitted light from the multi-wavelength light source;
receiving at an imaging device, at least one first image containing at least one first signal associated with an ocular property of the eye comprising at least one of corneal shape and ocular tear film thickness, comprises the emitted light reflected from the at least one first portion of the eye and at least one background signal;
spatially modulating light from the multi-wavelength light source to project a second circular pattern onto the eye, such that the at least one first portion of the eye does not receive emitted light from the multi-wavelength light source and the at least one second portion of the eye receives the emitted light from the multi-wavelength light source;
receiving at the imaging device, at least one second image containing at least one second signal comprising only the at least one background signal; and
subtracting the at least one second image from the at least one first image to generate at least one resulting image containing a resultant signal that represents the ocular property of the eye.

* * * * *

UNITED STATES PATENT AND TRADEMARK OFFICE
CERTIFICATE OF CORRECTION

PATENT NO. : 8,888,286 B2
APPLICATION NO. : 14/137105
DATED : November 18, 2014
INVENTOR(S) : Stephen M. Grenon et al.

It is certified that error appears in the above-identified patent and that said Letters Patent is hereby corrected as shown below:

Claims

Claim 19, at column 44, line 39, change "11" to --1--.

Signed and Sealed this
Eighteenth Day of August, 2015

Michelle K. Lee
*Director of the United States Patent and Trademark Office*